(12) United States Patent
Timmer et al.

(10) Patent No.: US 12,331,126 B2
(45) Date of Patent: Jun. 17, 2025

(54) OX40-BINDING POLYPEPTIDES AND USES THEREOF

(71) Applicant: Inhibrx Biosciences, Inc., La Jolla, CA (US)

(72) Inventors: John C. Timmer, San Diego, CA (US); William Crago, San Diego, CA (US); Kyle Jones, San Marcos, CA (US); Katelyn Willis, San Diego, CA (US); Florian Sulzmaier, San Diego, CA (US); Bryan Becklund, San Diego, CA (US); Brendan P. Eckelman, Encinitas, CA (US)

(73) Assignee: Inhibrx Biosciences, Inc., La Jolla, CA (US)

( * ) Notice: Subject to any disclaimer, the term of this patent is extended or adjusted under 35 U.S.C. 154(b) by 0 days.

(21) Appl. No.: 18/658,421

(22) Filed: May 8, 2024

(65) Prior Publication Data

US 2024/0409651 A1     Dec. 12, 2024

Related U.S. Application Data

(62) Division of application No. 17/818,106, filed on Aug. 8, 2022, now Pat. No. 12,012,459, which is a division of application No. 16/538,216, filed on Aug. 12, 2019, now Pat. No. 11,447,556.

(60) Provisional application No. 62/718,106, filed on Aug. 13, 2018.

(51) Int. Cl.
| | |
|---|---|
| C07K 16/28 | (2006.01) |
| A61K 35/17 | (2025.01) |
| A61P 35/00 | (2006.01) |
| C12N 15/85 | (2006.01) |

(52) U.S. Cl.
CPC .......... *C07K 16/2875* (2013.01); *A61K 35/17* (2013.01); *A61P 35/00* (2018.01); *C12N 15/85* (2013.01); *C07K 2317/569* (2013.01); *C12N 2015/8518* (2013.01)

(58) Field of Classification Search
None
See application file for complete search history.

(56) References Cited

U.S. PATENT DOCUMENTS

| | | |
|---|---|---|
| 5,151,510 A | 9/1992 | Stec et al. |
| 7,959,925 B2 | 6/2011 | Weinberg et al. |
| 8,614,295 B2 | 12/2013 | Lawson et al. |
| 2003/0157108 A1 | 8/2003 | Presta |
| 2004/0029129 A1 | 2/2004 | Wang et al. |
| 2004/0123343 A1 | 6/2004 | La Rosa et al. |
| 2004/0214272 A1 | 10/2004 | La Rosa et al. |
| 2013/0018175 A1 | 1/2013 | Verdonck et al. |
| 2013/0224224 A1 | 8/2013 | Singh et al. |
| 2013/0330335 A1 | 12/2013 | Bremel et al. |
| 2013/0332133 A1 | 12/2013 | Horn et al. |
| 2014/0037621 A1 | 2/2014 | Tsurushita et al. |
| 2014/0377284 A1 | 12/2014 | Simons et al. |
| 2015/0190506 A1 | 7/2015 | Cheung et al. |
| 2015/0355184 A1 | 12/2015 | Pierce et al. |
| 2017/0290913 A1 | 10/2017 | Cheung et al. |

FOREIGN PATENT DOCUMENTS

| | | |
|---|---|---|
| EP | 2844289 A1 | 3/2015 |
| WO | 9222583 A2 | 12/1992 |
| WO | 2004041862 A2 | 5/2004 |
| WO | 2005003169 A2 | 1/2005 |
| WO | 2005003170 A2 | 1/2005 |
| WO | 2005003171 A2 | 1/2005 |
| WO | 2005113605 A1 | 12/2005 |
| WO | 2006121810 A2 | 11/2006 |
| WO | 2007024715 A2 | 3/2007 |
| WO | 2009040562 A1 | 4/2009 |
| WO | 2010077634 A1 | 7/2010 |
| WO | 2012027570 A2 | 3/2012 |
| WO | 2012023053 A3 | 5/2012 |
| WO | 2013165690 A1 | 11/2013 |
| WO | 2014100079 A1 | 6/2014 |
| WO | 2014121099 A1 | 8/2014 |
| WO | 2014144357 A1 | 9/2014 |
| WO | 2014148895 A1 | 9/2014 |
| WO | 2014209804 A1 | 12/2014 |
| WO | 2016118733 A1 | 7/2016 |
| WO | 2016149201 A2 | 9/2016 |
| WO | 2017123673 A2 | 7/2017 |
| WO | 2018115003 A2 | 6/2018 |

OTHER PUBLICATIONS

Moore et al., "Engineered Fc variant antibodies with enhanced ability to recruit complement and mediate effector function", mAbs, 2010, vol. 2, No. 2, p. 181-189.

Morris et al., "Development and Characterization of Recombinant Human Fc:OX40L fusion protein linked via a coiled-coil trimerization domain," Mol. Immunol. May 2007; 44 (12): p. 3112-21.

Muller et al. "Targeting Co-Stimulatory Receptors of the TNF Superfamily for Cancer Immunotherapy", BioDrugs (2023) 37: p. 21-33.

Muller S. et al., "Spliceosomal peptide P140 for immunotherapy of systemic lupus erythematosus: results of an early phase II clinical trial, Arthritis & Rheumatism:" Official Journal of the American College of Rheumatology, 2008, v. 58, n. 12, p. 3873-3883.

Muller, Dafne et al., "Recombinant bispecific antibodies for cellular cancer immunotherapy," Current opinion in Molecular Therapeu, Current Drugs, London GB, (9)(4), Aug. 1, 2007, p. 319-326.

(Continued)

*Primary Examiner* — Amy E Juedes
*Assistant Examiner* — Peter Johansen
(74) *Attorney, Agent, or Firm* — McNeill PLLC

(57) ABSTRACT

Provided herein are VHH-containing polypeptides that bind OX40. In some embodiments, VHH-containing polypeptides that bind and agonize OX40 are provided. Uses of the VHH-containing polypeptides are also provided.

47 Claims, 14 Drawing Sheets

Specification includes a Sequence Listing.

(56) References Cited

OTHER PUBLICATIONS

Müller, N., et al., (2008). "Activity of soluble OX40 ligand is enhanced by oligomerization and cell surface immobilization". The FEBS journal, 275(9), p. 2296-2304.
Natsume et al. "Engineered Antibodies of IgG 1/IgG 3 Mixed Isotype with Enhanced Cytotoxic Activities", Cancer Research, 2008, vol. 68, No. 10, p. 3863-3872.
Needleman and Wunsch "A General Method Applicable to the Search for Similarities in the Amino Acid Sequence of Two Proteins", J. Mol. Biol., 1970, vol. 48, p. 443-453.
Nelson et al., "The "Trojan Horse" Approach to Tumor Immunotherapy: Targeting the Tumor Microenvironment," J. Immunol. Res., 2014, N.789069, p. 1-14.
Pearson et al. "Improved tools for biological sequence comparison", 1988, Proc. Natl. A.cad. Sci. USA, vol. 85, p. 2444-2448.
Prokofieva L.V. et al., "Course of lectures on general pharmacology" teaching aid, Ulyanovsk: UlGU, 2017, 155; p. 65-77.
Pukac et al. "HGS-ETRI, a fully human TRAIL-receptor I monoclonal antibody, induces cell death in multiple tumour types in vitro and in vivo", British Journal of Cancer, 2005, vol. 92, p. 1430-1441.
Pullen et al., "High-Affinity Interactions of Tumor Necrosis Factor Receptor-Associated Factors (TRAFs) and CD40 Require TRAF Trimerization and CD40 Multimerization," Biochemistry. Aug. 3, 1999; 38 (31 ): p. 10168-77.
Rahbarizadeh et al., Nanobody, New Agent for Combating Against Breast Cancer Cells, Breast Cancer—Current and Alternative Therapeutic Modalities, p. 347-370 (2011).
Rizo et al. "Constrained Peptides: Models of Bioactive Peptides and Protein Substructures", Ann. Rev. Biochem., 1992, vol. 61, p. 387-418.
Rossi et al. "Hexavalent bispecific antibodies represent a new class of anticancer therapeutics: 1. Properties of anti-CD20/CD22 antibodies in lymphoma," Blood. Jun. 11, 2009; 113 (24): p. 6161-6171.
Saerens et al., "Identification of a Universal VHH Framework to Graft Non-canonical Antigen-binding Loops of Camel Single-domain Antibodies," J. Mol. Biol. Sep. 23, 2005; 352 (3): p. 597-607.
Safdari et al., "Antibody humanization methods—a review and update," Biotechnology and Genetic Engineering Reviews, 2013, V. 29, N. 2, p. 175-186.
Search Report issued in corresponding Singaporean application No. 11201805422W, dated Sep. 18, 2019, 4 pages.
Shields et al. "High-Resolution Mapping of the Binding Site on Human IgG 1 for FcyRI, FcyRII, FcyRIII, and FcRn and Design of IgG 1 Variants with Improved Binding to the FcyR", The Journal of Biological Chemistry, 2001, vol. 276, No. 9, p. 6591-6604.
Smith et al. "Comparison of Biosequences", 1981, Advances in Applied Mathematics, vol. 2, p. 482-489.
Spitler L.E., "Cancer vaccines: the interferon analogy", Cancer Biother., 1995, v. 10, n. 1, p. 1-3.
Stavenhagen et al. "Enhancing the potency of therapeutic monoclonal antibodies via Fc optimization", Advances in Enzyme Regulations, 2008, vol. 48, p. 152-164.
Stavenhagen et al. "Fc Optimization of Therapeutic Antibodies Enhances Their Ability to Kill Tumor Cells In vitro and Controls Tumor Expansion In vivo via Low-Affinity Activating Fey Receptors", Cancer Research, 2007, vol. 67, No. 18, p. 8882-8890.
Stec et al. "Automated Solid-Phase Synthesis, Separation, and Stereochemistry of Phosphorothioate Analogues of Oligodeoxyribonucleotides", J. Am. Chem. Soc., 1984, vol. 106, No. 20, p. 6077-6079.
Stein et al. "Physicochemical properties of phosphorothioate oligodeoxynucleotides", Nucl. Acids Res., 1988, vol. 16, No. 8, p. 3209-3221.
Teplyakov et al., "Antibody modeling assessment II Structures and models," Proteins: Structure, Function, and Bioinformatics, 2014, V. 82, N. 8, p. 1563-1582.
Thornton et al. "Prediction of progress at last", Nature, 1991, vol. 354, p. 105-106.
Uhlmann et al. "Antisense Oligonucleotides: A New Therapeutic Principle", Chemical Reviews, 1990, vol. 90, No. 4, p. 544-584.
Veber et al. "The design of metabolically-stable peptide analogs", TINS, Sep. 1985, p. 392-396.
Verma et al., "Antibody engineering: comparison of bacterial, yeast, insect and mammalian expression systems" J Immunol Methods Jul. 1, 1998;216(1-2): p. 165-81.
Vincke et al. "General Strategy to Humanize a Camelid Single-Domain Antibody and Identification of a Universal Humanzied Nanobody Scaffold," J. Biol. Chem. Jan. 30, 2009; 284 (5): p. 3273-84.
Vincke et al. "Generation of Single Domain Antibody Fragments Derived from Camelids and Generation of Manifold Constructs," Methods Mol. Biol. 2012; 907: p. 145-76.
Weinberg et al., "Science gone translational: the OX40 agonist story" Immunol Rev. 244(1): p. 218-231 (2011).
Wesolowski et al. "Single domain antibodies: promising experimental and therapeutic tools in in infection and immunity" Med. Microbiol. Immunol. 2009; 198 (3): p. 157-174.
Yada A. et al. "A novel humanized anti-human death receptor 5 antibody CS-1008 induces apoptosis in tumor cells without toxicity in hepatocytes", Annals of Oncology, 2008, vol. 19, p. 1060-1067.
Zalevsky et al. "Enhanced antibody half-life improves in vivo activity", Nature Biotechnology, 2010, vol. 28, No. 2, p. 157-159.
Zhang et al. "Lexatumumab (TRAIL-receptor 2 mAb) induces expression of DR5 and promotes apoptosis in primary and metastatic renal cell carcinoma in a mouse orthotopic model", Cancer Letters, 2007, vol. 251, p. 146-157.
Zon et al. "Phosphorothioate oligonucleotides: chemistry, purification, analysis, scale-up and future directions", Anti Cancer Drug Design, 1991, vol. 6, p. 539-568.
Zon et al., "Phosphorothioate oligonucleotides", in Oligonucleotides and Analogues: A Practical Approach, 1991, p. 87-108.
Adair et al., "Therapeutic Antibodies" Drug Design Reviews, vol. 2, No. 3, 2005, pp. 209-217(9).
Alegre et al. "Effect of a single amino acid mutation on the activating and immunosuppressive properties of a 'humanized' OKT3 monoclonal antibody", The Journal of immunology, 1992, vol. 148, p. 3461-3468.
Bannas et al. "Nanobodies and Nanobody-Based Human Heavy Chain Antibodies As Antitumor Therapeutics," Front. Immunol. Nov. 22, 2017; 8: 1603; pp. 1-13.
Barker et al., "Detecting Distant Relationships: Computer Methods and Results", in Dayhoff, M.O., Atlas of Protein Sequence and Structure, 1972, vol. 5, pp. 101-110.
Blanco-Toribio et al. "Generation and characterization of monospecific and bispecific hexavalent trimerbodies," MAbs. Jan.-Feb. 2013; 5 (1): pp. 70-79.
Bonifant et al., "Toxicity and management in CAR T-cell therapy", Mol Ther Oncolytics, 2016, v.20, n.3, p. 16011.
Borisov et al., "Tumor microenvironment as a target of malignant gliomas treatment," Malignant Tumours 2015; 4: pp. 14-23.
Bowie et al. "A Method to Identify Protein Sequences That Fold into a Known Three-Dimensional Structure", 1991, Science, vol. 253, p. 164-170.
Bulliard et al. "Activating Fc y receptors contribute to the antitumor activities of immunoregulatory receptor-targeting antibodies", J. Exp. Med., vol. 210, No. 9, p. 1685-1693.
Bulliard et al. "OX40 engagement depletes intratumoral Tregs via activating FcyRs, leading to antitumor efficacv", Immunologv and Cell Biology, 2014, vol. 92, p. 475-480.
Carter, "Bispecific human IgG by design", Journal of immunological Methods, 2001, vol. 248, p. 7-15.
Chen et al., "Fusion protein linkers: property, design and functionality," Advanced drug delivery reviews, 2013, V. 65, N. 10, p. 1357-1365.
Chothia et al. "Canonical Structures for the Hypervariable Regions of immunoglobulins", J. Mol. Biol., 1987, vol. 196, p. 901-917.
Chothia et al. "Conformations of immunoglobulin hypervariable regions", Nature, 1989, vol. 342, p. 878-883.
Colman, "Effects of amino acid sequence changes on antibody-antigen interactions, Research in Immunology," 1994, V. 145, N. 1, p. 33-36.

(56) References Cited

OTHER PUBLICATIONS

Cuesta et al., "Improved stability of multivalent antibodies containing the human collagen XV trimerization domain," MAbs. Mar.-Apr. 2012; 4 (2): p. 226-32.
Cuesta et al., "Multivalent antibodies: when design surpasses evolution," Cell Press Trends in Biotechnology (28), p. 355-362 (2010).
Dall' Acqua et al. "Properties of Human IgG Is Engineered for Enhanced Binding to the Neonatal Fe Receptor (FcRn)", The Journal of Biological Chemistry, 2006, vol. 281, No. 33, p. 23514-23524.
Davies et al. "Antibody-Antigen Complexes", Annual Rev Biochem, 1990, vol. 59, p. 439-473.
Dayhoff, M.O., "Survey of New Data and Computer Methods of Analysis", in Atlas of Protein Sequence and Structure, 1976, vol. 5, Supplement 2, p. 1-8.
Delia Nelson et al., "The "Trojan Horse" Approach to Tumor Immunotherapy: Targeting the Tumor Microenvironment", J. Immunol. Res., 2014, v.2014, art.789069, p. 1-14.
European Search Report issued in EP 17738885.7, dated Jul. 8, 2019, 8 pages.
Evans et al. "Design of Nonpeptidal Ligands for a Peptide Receptor: Cholecystokinin Antagonists", J. Med. Chem., 1987, vol. 30, p. 1229-1239.
Fauchere, "Elements for the Rational Design of Peptide Drugs", Advances in Drug Research, 1986, vol. 15, p. 29-69.
Fidler, IJ. "Biological heterogeneity of cancer", Human Vaccines & Immunotherapeutics 8:8, p. 1141-1142 (Year: 2012).
Gale, Robert, "Cellular and Molecular Basis of Cancer", Merck Manuals Online Medical Library, [online]. Whitehouse Station, NJ: Merck Research Laboratories, 2006-2007. [retrieved on Oct. 19, 2020]. < URL: https://www.merckmanuals.com/professional/hematology- and- oncology/overview-of-cancer/ cellular-and-molecular-basis-of-cancer> (Year: 2020); 8 pages.
Graves et al. "Apo2L/TRAIL and the Death Receptor 5 Agonist Antibody AMG 655 Cooperate to Promote Receptor Clustering and Antitumor Activity", Cancer Cell, 2014, vol. 26, p. 177-189.
Gura T., "Systems for identifying new drugs are often faulty", Science, 1997, v.278, n.5340, p. 1041-1042.
Haigh P.I. et al., "Vaccine therapy for patients with melanoma", Oncology, 1999, v.13, n. 11, abstract, 1 page.
Hino et al., "G-protein-coupled receptor inactivation by an allosteric inverse-agonist antibody" Nature 482 (2012); 5 pages.
Holliger et al., "Engineered antibody fragments and the rise of single domains," Nat. Biotechnol. Sep. 2005; 23 (9): p. 1126-36.
Huet et al., "Mulivalent nanobodies targeting death receptor 5 elicit superior tumor cell killing through efficient caspase induction," MAbs. 2014; 6 (6): p. 1560-70.

Ichikawa et al. "Tumoricidal activity of a novel anti-human DR5 monoclonal antibody without hepatocyte cytotoxicity", 2001, Nature Medicine, vol. 7, No. 8, p. 954-960.
Idusogie et al. "Engineered Antibodies with Increased Activity to Recruit Complement", The Journal of immunology, 2001, vol. 166, p. 2571-2575.
International Search Report and Written Opinion for PCT/US17/13070 dated Jun. 30, 2017; 26 pages.
International Search Report and Written Opinion issued in PCT/US2019/046156, dated Dec. 2, 2019, 12 pages.
Jain R.K., "Barriers to drug delivery in solid tumors", Sci. Am., 1994, v.271, n. 1, p. 58-65.
Kaneko et al. "Optimizing Therapeutic Antibody Function", Biodrugs, 2011, vol. 25, No. 1, p. 1-11.
Kjaergaard et al. "Augmentation Versus Inhibition: Effects of Conjunctional OX-40 Receptor Monoclonal Antibody and IL-2 Treatment on Adoptive Immunotherapy of Advanced Tumor." (J. Immunol. Dec. 1, 2001; 167 (11): p. 6669-77.
Kontermann et al., "Bispecific antibodies", Drug Discovery Today, 2015, V. 7, N. 20, p. 838-847.
LaPlanche et al. "Phosphorothioate-modified oligodeoxyribonucleotides. III. NMR and UV spectroscoptc studies of the Rp-Rp, Sp-Sp, and RrSP duplexes, [dCGGsAATTCC]2, derived from diastereomeric 0-ethyl phosphorothioates", Nucleic Acids Research, 1986, vol. 14, No. 22, p. 9081-9093.
Lazar et al. "Engineered antibody Fc variants with enhanced effector function", PNAS, 2006, vol. 103, No. 11, p. 4005-4010.
Lee K.H. et al., Increased vaccine-specific T cell frequency after peptide-based vaccination correlates with increased susceptibility to in vitro stimulation but does not lead to tumor regression, J. Immunol., 1999, v. 163, n. 11, p. 6292-6300.
Li et al. "Antibody-based cancer immunotherapy by targeting regulatory T cells," Frontiers in Oncology 13:1157345. (2023), pp. 1-13.
Li et al. "LBY135, a Novel Anti-DR5 Agonistic Antibody Induces Tumor Cell-Specific Cytotoxic Activity in Human Colon Tumor Cell Lines and Xenografts", Drug Development Research, 2008, vol. 69, p. 69-82.
Li J et al., Chimeric antigen receptor T cell (CAR-T) immunotherapy for solid tumors: lessons learned and strategies for moving forward, J Hematol Oncol., 2018, Feb. 13, 2018, v.11, n.1, p. 22-40.
Linch S. et al., "OX40 agonists and combination immunotherapy: putting the pedal to the metal," Frontiers in Oncology, Feb. 16, 2015, vol. 5, pp. 34: p. 1-14.
Locksley et al., "The TNF and TNF receptor superfamilies: integrating mammalian biology," Cell, 2001, V. 104, N. 4, p. 487-501.
Maeda et al., "Engineering of functional chimeric protein G-Vargula Luciferase," Analytical biochemistry, 1997, V. 249, N. 2, p. 147-152.
Malmqvist, M. "Biospecific interaction analysis using biosensor technology", Nature, 1993, vol. 361, p. 186-187.

OX40-BINDING POLYPEPTIDES AND USES THEREOF

CROSS-REFERENCE TO RELATED APPLICATIONS

This application is a divisional of U.S. patent application Ser. No. 17/818,106, filed Aug. 8, 2022, which is a divisional of U.S. patent application Ser. No. 16/538,216, filed Aug. 12, 2019, now issued as U.S. Pat. No. 11,447,556 on Sep. 20, 2022, which claims the benefit of priority of U.S. Provisional Application No. 62/718,106, filed Aug. 13, 2018, which is incorporated by reference herein in its entirety for any purpose.

SEQUENCE LISTING

This application includes a Sequence Listing submitted in electronic format entitled "2022-08-08_01202-0014-01US_sequence.xml" created Aug. 8, 2022, which is 46,051 bytes in size, and which is incorporated by reference in its entirety.

FIELD

The present invention relates to OX40-binding polypeptides, and methods of using OX40-binding polypeptides to modulate the biological activity of OX40. Such methods include, but are not limited to, methods of treating cancer. In some embodiments, the OX40-binding polypeptides are multivalent OX40-binding polypeptides.

BACKGROUND

The tumor necrosis factor receptor superfamily (TNFRSF) includes several structurally related cell surface receptors. Activation by multimeric ligands is a common feature of many of these receptors, and such activation has therapeutic utility in numerous pathologies if activated properly. Effective agonism of this receptor family may require higher order clustering than is achieved using traditional bivalent antibodies.

OX40 (TNFRSF4, CD134) is a member of the TNF receptor superfamily, and is expressed on the surface of T cells 24 to 72 hours following T cell activation. Antigen presenting cells in close proximity to activated T cells present OX40 ligand (OX40L) on their surface, which binds and clusters OX40 on T cells sending a co-stimulatory signal that increases T-cell expansion and enhances effector T-cell differentiation. Activation of OX40 therefore serves to maintain an immune response, e.g., by enhancing survival and function of T cells.

Therefore, there exists a therapeutic need for more potent agonists of OX40.

SUMMARY

Provided herein are polypeptides comprising at least one VHH domain that binds OX40, wherein the VHH domain comprises a CDR1 comprising the amino acid sequence of SEQ ID NO: 10, a CDR2 comprising the amino acid sequence of SEQ ID NO: 11, and a CDR3 comprising the amino acid sequence of SEQ ID NO: 12. In some embodiments, the VHH domain is humanized. In some embodiments, the VHH domain comprises a framework 2 (FR2) comprising the amino acid sequence of SEQ ID NO: 22. In some embodiments, the VHH domain comprises a FR2 comprising the amino acid sequence of SEQ ID NO: 22 and a FR3 comprising the amino acid sequence of SEQ ID NO: 23. In some embodiments, the VHH domain comprises the amino acid sequence of SEQ ID NO: 9.

In some embodiments, the polypeptide comprises two VHH domains. In some embodiments, the polypeptide comprises three VHH domains. In some embodiments, the polypeptide comprises four VHH domains. In some embodiments, the polypeptide comprises at least one binding domain that binds a second antigen other than OX40. In some such embodiments, the second antigen is selected from PD-1, PD-L1, and 41BB. In some embodiments, the at least one binding domain that binds a second antigen is an antagonist or an agonist. In some embodiments, the at least one binding domain that binds a second antigen is a VHH domain.

In some embodiments, each VHH domain binds OX40. In some embodiments, each VHH domain comprises a CDR1 comprising the amino acid sequence of SEQ ID NO: 10, a CDR2 comprising the amino acid sequence of SEQ ID NO: 11, and a CDR3 comprising the amino acid sequence of SEQ ID NO: 12. In some embodiments, each VHH domain comprises a framework 2 (FR2) comprising the amino acid sequence of SEQ ID NO: 22. In some embodiments, each VHH domain comprises a FR2 comprising the amino acid sequence of SEQ ID NO: 22 and a FR3 comprising the amino acid sequence of SEQ ID NO: 23. In some embodiments, each VHH domain comprises the amino acid sequence of SEQ ID NO: 9.

In some embodiments, the polypeptide comprises an Fc domain. In some embodiments, the Fc domain comprises an amino acid sequence selected from SEQ ID NOs: 25 and 26. In some embodiments, the polypeptide comprises the amino acid sequence of SEQ ID NO: 14. In some embodiments, the polypeptide comprises the amino acid sequence of SEQ ID NO: 15. In some embodiments, provided herein is a polypeptide that binds OX40 comprising the amino acid sequence of SEQ ID NO: 15. In some embodiments, provided herein is a polypeptide that binds OX40 consisting of the amino acid sequence of SEQ ID NO: 15.

In various embodiments, the polypeptide provided herein forms a dimer under physiological conditions. In some such embodiments, the polypeptide comprises an Fc domain.

In some embodiments, a polypeptide provided herein increases $CD4^+$ and/or $CD8^+$ T cell proliferation in vitro and/or in vivo. In some embodiments, the polypeptide increases $CD4^+$ and/or $CD8^+$ T cell proliferation in the presence of Treg cells. In some embodiments, the polypeptide increases $CD4^+$ and/or $CD8^+$ T cell proliferation in vitro by at least 1.5-fold or by at least 2-fold. In some embodiments, the polypeptide increases $CD4^+$ and/or $CD8^+$ T cell proliferation in vivo by at least 1.5-fold or by at least 2-fold.

In some embodiments, the polypeptide increases CD25 expression on $CD4^+$ and/or $CD8^+$ T cells in vitro and/or in vivo. In some embodiments, the polypeptide increases CD25 expression on $CD4^+$ and/or $CD8^+$ T cells in vitro by at least 1.5-fold or by at least 2-fold. In some embodiments, the polypeptide increases CD25 expression on $CD4^+$ and/or $CD8^+$ T cells in vivo by at least 1.5-fold or by at least 2-fold.

In some embodiments, the polypeptide increases CD71 expression on $CD4^+$ and/or $CD8^+$ T cells in vitro and/or in vivo. In some embodiments, the polypeptide increases CD71 expression on $CD4^+$ and/or $CD8^+$ T cells in vitro by at least 1.5-fold or by at least 2-fold. In some embodiments, the polypeptide increases CD71 expression on $CD4^+$ and/or $CD8^+$ T cells in vivo by at least 1.5-fold or by at least 2-fold.

In some embodiments, the polypeptide increases NFκB signaling in CD4+ and/or CD8+ T cells in vitro and/or in vivo. In some embodiments, the polypeptide increases NFκB signaling in CD4+ and/or CD8+ T cells in vitro by at least 1.5-fold, at least 2-fold, at least 3-fold, or by at least 5-fold. In some embodiments, the polypeptide increases NFκB signaling in CD4+ and/or CD8+ T cells in vivo by at least 1.5-fold, at least 2-fold, at least 3-fold, or by at least 5-fold.

In some embodiments, the polypeptide increases IFNγ expression in CD4+ and/or CD8+ T cells in vitro and/or in vivo. In some embodiments, the polypeptide increases IFNγ expression in CD4+ and/or CD8+ T cells in vitro by at least 1.5-fold, at least 2-fold, at least 3-fold, or by at least 5-fold. In some embodiments, the polypeptide increases IFNγ expression in CD4+ and/or CD8+ T cells in vivo by at least 1.5-fold, at least 2-fold, at least 3-fold, or by at least 5-fold.

In various embodiments, the polypeptide increases the expression of CD25, CD71, and/or IFNγ, and/or increases NFκB signaling in the presence of Treg cells. In various embodiments, the increase is determined as an average of results from T cells of at least five or at least ten different healthy human donors.

In various embodiments, the polypeptide comprising at least one VHH domain that binds OX40 provided herein is an agonist of OX40 biological activity. In some embodiments, the OX40 is human OX40. In some embodiments, the polypeptide binds human OX40 with an affinity ($K_D$) of less than 10 nM, less than 5 nM, less than 2 nM, or less than 1 nM. In some embodiments, the polypeptide binds cynomolgus monkey OX40 with an affinity ($K_D$) of less than 10 nM, less than 5 nM, less than 2 nM, or less than 1 nM.

In some embodiments, pharmaceutical compositions are provided, comprising a polypeptide comprising at least one VHH domain that binds OX40 provided herein and a pharmaceutically acceptable carrier.

In some embodiments, an isolated nucleic acid is provided that encodes a polypeptide comprising at least one VHH domain that binds OX40 provided herein. In some embodiments, a vector is provided that comprises the nucleic acid. In some embodiments, a host cell comprising the nucleic acid or vector is provided. In some embodiments, a host cell is provided that expresses a polypeptide comprising at least one VHH domain that binds OX40 provided herein. In some embodiments, the host cell secretes the OX40-binding polypeptide. In some embodiments, the host cell is a primary human cell. In some embodiments, the host cell is a T cell. In some embodiments, the host cell is a chimeric antigen receptor (CAR)-T cell.

In some embodiments, a method of producing the polypeptide comprising at least one VHH domain that binds OX40 is provided, comprising incubating the host cell under conditions suitable for expression of the polypeptide. In some embodiments, the method further comprises isolating the polypeptide.

In some embodiments, a method of increasing CD4+ and/or CD8+ T cell proliferation is provided, comprising contacting T cells with a polypeptide comprising at least one VHH domain that binds OX40. In some embodiments, a method of increasing CD25 expression on CD4+ and/or CD8+ T cells is provided, comprising contacting T cells with a polypeptide comprising at least one VHH domain that binds OX40. In some embodiments, a method of increasing CD71 expression on CD4+ and/or CD8+ T cells is provided, comprising contacting T cells with a polypeptide comprising at least one VHH domain that binds OX40. In some embodiments, a method of increasing IFNγ expression in CD4+ and/or CD8+ T cells is provided, comprising contacting T cells with a polypeptide comprising at least one VHH domain that binds OX40. In some embodiments, a method of increasing NFκB signaling in CD4+ and/or CD8+ T cells is provided, comprising contacting T cells with a polypeptide comprising at least one VHH domain that binds OX40. In various embodiments, the CD4+ and/or CD8+ T cells are in vitro. In various embodiments, the CD4+ and/or CD8+ T cells are in vivo. In various embodiments, the CD4+ and/or CD8+ T cells are in the presence of Treg cells. In various embodiments, the increase is at least 1.5-fold, at least 2-fold, at least 3-fold, or by at least 5-fold.

In some embodiments, methods of treating cancer are provided, comprising administering to a subject with cancer a pharmaceutically effective amount of a polypeptide comprising at least one VHH domain that binds OX40 provided herein. In some embodiments, methods of treating cancer are provided, comprising administering to a subject with cancer a pharmaceutically effective amount of a host cell that expresses the polypeptide comprising at least one VHH domain that binds OX40 provided herein. In some embodiments, the host cell secretes the OX40-binding polypeptide. In some embodiments, the host cell expresses the OX40-binding polypeptide on the surface. In some embodiments, the cancer is selected from basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer; gastrointestinal cancer; glioblastoma; hepatic carcinoma; hepatoma; intraepithelial neoplasm; kidney or renal cancer; larynx cancer; liver cancer; lung cancer; small-cell lung cancer; non-small cell lung cancer; adenocarcinoma of the lung; squamous carcinoma of the lung; melanoma; myeloma; neuroblastoma; oral cavity cancer; ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma; Hodgkin's lymphoma; non-Hodgkin's lymphoma; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; chronic lymphocytic leukemia (CLL); acute lymphoblastic leukemia (ALL); Hairy cell leukemia; and chronic myeloblastic leukemia.

In some embodiments, the method of treating cancer further comprises administering an additional therapeutic agent. In some embodiments, the additional therapeutic agent is an anti-cancer agent. In some embodiments, the anti-cancer agent is selected from a chemotherapeutic agent, an anti-cancer biologic, radiation therapy, CAR-T therapy, and an oncolytic virus. In some embodiments, the additional therapeutic agent is an anti-cancer biologic. In some embodiments, the anti-cancer biologic is an agent that inhibits PD-1 and/or PD-L1. In some embodiments, the anti-cancer biologic is selected from nivolumab, pidilizumab, pembrolizumab, durvalumab, atezolizumab, avelumab, AMP-224, BMS-936559, AMP-514, MDX-1105, TSR-042, STI-A1010, and STI-A1110. In some embodiments, the anti-cancer biologic is an agent that inhibits VISTA, gpNMB, B7H3, B7H4, HHLA2, CD73, CTLA4, or TIGIT. In some embodiments, the anti-cancer biologic is an antibody. In some embodiments, the anti-cancer biologic is a cytokine. In some embodiments, the anti-cancer agent is CAR-T therapy. In some embodiments, the anti-cancer agent is an oncolytic virus. In some embodiments, a method of treating cancer provided herein further comprises tumor resection and/or radiation therapy.

BRIEF DESCRIPTION OF THE FIGURES

FIG. 14A shows the combination of 10 nM pembrolizumab with varying concentrations of hexavalent 3x1D10v6-Fc. FIG. 14B shows the combination of 1 nM hexavalent 3x1D10v6-Fc with varying concentrations of pembrolizumab.

DETAILED DESCRIPTION

Figure 1:
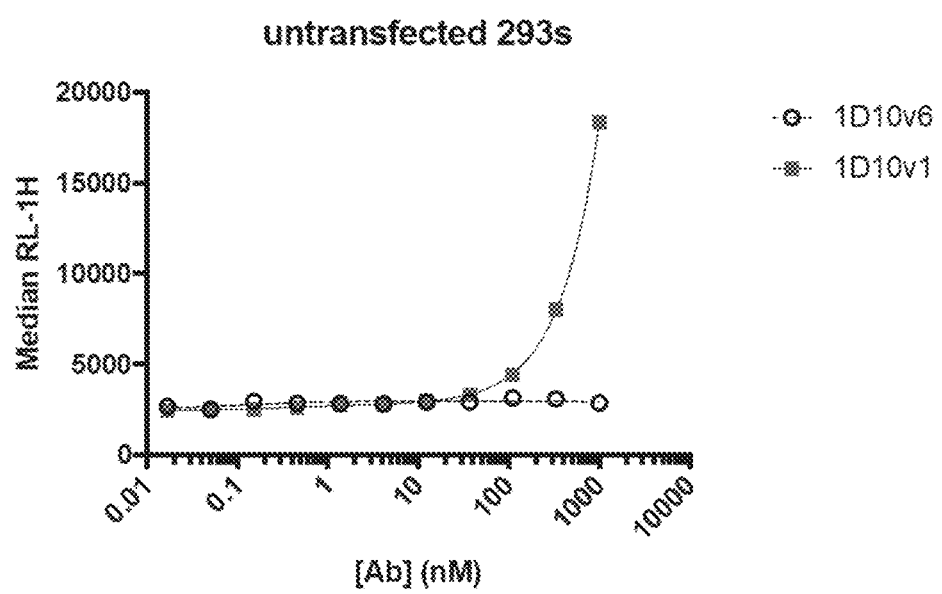
FIG. 1 shows nonspecific binding of 1D10v1-Fc and 1D10v6-Fc to untransfected HEK293 cells.

Embodiments provided herein relate to multivalent OX40-binding polypeptides that modulate the activity of OX40 and their use in various methods of treating cancer.

Definitions and Various Embodiments

The section headings used herein are for organizational purposes only and are not to be construed as limiting the subject matter described.

All references cited herein, including patent applications, patent publications, and Genbank Accession numbers are herein incorporated by reference, as if each individual reference were specifically and individually indicated to be incorporated by reference in its entirety.

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch. 1997); Antibodies: A Practical Approach (D. Catty., ed., IRL Press. 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J.B. Lippincott Company, 1993); and updated versions thereof.

Unless otherwise defined, scientific and technical terms used in connection with the present disclosure shall have the meanings that are commonly understood by those of ordinary skill in the art. Further, unless otherwise required by context or expressly indicated, singular terms shall include pluralities and plural terms shall include the singular. For any conflict in definitions between various sources or references, the definition provided herein will control.

In general, the numbering of the residues in an immunoglobulin heavy chain is that of the EU index as in Kabat et al., *Sequences of Proteins of Immunological Interest,* 5th Ed. Public Health Service, National Institutes of Health. Bethesda. Md. (1991). The "EU index as in Kabat" refers to the residue numbering of the human IgG1 EU antibody.

It is understood that embodiments of the invention described herein include "consisting" and/or "consisting essentially of" embodiments. As used herein, the singular form "a", "an", and "the" includes plural references unless indicated otherwise. Use of the term "or" herein is not meant to imply that alternatives are mutually exclusive.

In this application, the use of "or" means "and/or" unless expressly stated or understood by one skilled in the art. In the context of a multiple dependent claim, the use of "or" refers back to more than one preceding independent or dependent claim.

The phrase "reference sample", "reference cell", or "reference tissue", denote a sample with at least one known characteristic that can be used as a comparison to a sample with at least one unknown characteristic. In some embodiments, a reference sample can be used as a positive or negative indicator. A reference sample can be used to establish a level of protein and/or mRNA that is present in, for example, healthy tissue, in contrast to a level of protein and/or mRNA present in the sample with unknown characteristics. In some embodiments, the reference sample comes from the same subject, but is from a different part of the subject than that being tested. In some embodiments, the reference sample is from a tissue area surrounding or adjacent to the cancer. In some embodiments, the reference sample is not from the subject being tested, but is a sample from a subject known to have, or not to have, a disorder in question (for example, a particular cancer or OX40-related disorder). In some embodiments, the reference sample is from the same subject, but from a point in time before the subject developed cancer. In some embodiments, the reference sample is from a benign cancer sample, from the same or a different subject. When a negative reference sample is used for comparison, the level of expression or amount of the molecule in question in the negative reference sample will indicate a level at which one of skill in the art will appreciate, given the present disclosure, that there is no and/or a low level of the molecule. When a positive reference sample is used for comparison, the level of expression or amount of the molecule in question in the positive reference sample will indicate a level at which one of skill in the art will appreciate, given the present disclosure, that there is a level of the molecule.

The terms "benefit", "clinical benefit", "responsiveness", and "therapeutic responsiveness" as used herein in the context of benefiting from or responding to administration of a therapeutic agent, can be measured by assessing various endpoints, e.g., inhibition, to some extent, of disease progression, including slowing down and complete arrest; reduction in the number of disease episodes and/or symptoms; reduction in lesion size; inhibition (that is, reduction, slowing down or complete stopping) of disease cell infiltration into adjacent peripheral organs and/or tissues; inhibition (that is, reduction, slowing down or complete stopping) of disease spread, relief, to some extent, of one or more symptoms associated with the disorder: increase in the length of disease-free presentation following treatment, for example, progression-free survival; increased overall survival; higher response rate, and/or decreased mortality at a given point of time following treatment. A subject or cancer that is "non-responsive" or "fails to respond" is one that has failed to meet the above noted qualifications to be "responsive".

The terms "nucleic acid molecule", "nucleic acid" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides comprised in the nucleic acid molecule or polynucleotide.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present disclosure, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

"OX40" as used herein refers to any native, mature OX40 that results from processing of an OX40 precursor in a cell. The term includes OX40 from any vertebrate source, including mammals such as primates (e.g., humans and cynomolgus or rhesus monkeys) and rodents (e.g., mice and rats), unless otherwise indicated. The term also includes naturally-occurring variants of OX40, such as splice variants or allelic variants. A nonlimiting exemplary human OX40 amino acid sequence is shown, e.g., in GenBank Accession No. CAE11757.1. See SEQ ID NO. 1. A nonlimiting exemplary cynomolgus monkey OX40 amino acid sequence is shown, e.g., in NCBI Accession No. XP_005545179. See SEQ ID NO. 2.

The term "specifically binds" to an antigen or epitope is a term that is well understood in the art, and methods to determine such specific binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. A single-domain antibody (sdAb) or VHH-containing polypeptide "specifically binds" or "preferentially binds" to a target if it binds with greater affinity, avidity, more readily, and/or with greater duration than it binds to other substances. For example, a sdAb or VHH-containing polypeptide that specifically or preferentially binds to an OX40 epitope is a sdAb or VHH-containing polypeptide that binds this epitope with greater affinity, avidity, more readily, and/or with greater duration than it binds to other OX40 epitopes or non-OX40 epitopes. It is also understood by reading this definition that; for example, a sdAb or VHH-containing polypeptide that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding. "Specificity" refers to the ability of a binding protein to selectively bind an antigen.

As used herein, the term "modulate" with regard to the activity of OX40 refers to a change in the activity of OX40. In some embodiments, "modulate" refers to an increase in OX40 activity compared to OX40 in the absence of the modulator.

As used herein, the term "epitope" refers to a site on a target molecule (for example, an antigen, such as a protein, nucleic acid, carbohydrate or lipid) to which an antigen-binding molecule (for example, a sdAb or VHH-containing polypeptide) binds. Epitopes often include a chemically active surface grouping of molecules such as amino acids, polypeptides or sugar side chains and have specific three-dimensional structural characteristics as well as specific charge characteristics. Epitopes can be formed both from contiguous and/or juxtaposed noncontiguous residues (for example, amino acids, nucleotides, sugars, lipid moiety) of the target molecule. Epitopes formed from contiguous residues (for example, amino acids, nucleotides, sugars, lipid moiety) typically are retained on exposure to denaturing solvents whereas epitopes formed by tertiary folding typically are lost on treatment with denaturing solvents. An epitope may include but is not limited to at least 3, at least 5 or 8-10 residues (for example, amino acids or nucleotides). In some embodiments, an epitope is less than 20 residues (for example, amino acids or nucleotides) in length, less than 15 residues or less than 12 residues. Two antibodies may bind the same epitope within an antigen if they exhibit competitive binding for the antigen. In some embodiments, an epitope can be identified by a certain minimal distance to a CDR residue on the antigen-binding molecule. In some embodiments, an epitope can be identified by the above distance, and further limited to those residues involved in a bond (for example, a hydrogen bond) between a residue of the antigen-binding molecule and an antigen residue. An epitope can be identified by various scans as well, for example an alanine or arginine scan can indicate one or more residues that the antigen-binding molecule can interact with. Unless explicitly denoted, a set of residues as an epitope does not exclude other residues from being part of the epitope for a particular antigen-binding molecule. Rather, the presence of such a set designates a minimal series (or set of species) of epitopes. Thus, in some embodiments, a set of residues identified as an epitope designates a minimal epitope of relevance for the antigen, rather than an exclusive list of residues for an epitope on an antigen.

A "nonlinear epitope" or "conformational epitope" comprises noncontiguous polypeptides, amino acids and/or sugars within the antigenic protein to which an antigen-binding molecule specific to the epitope binds. In some embodiments, at least one of the residues will be noncontiguous with the other noted residues of the epitope; however, one or more of the residues can also be contiguous with the other residues.

A "linear epitope" comprises contiguous polypeptides, amino acids and/or sugars within the antigenic protein to which an antigen-binding molecule specific to the epitope binds. It is noted that, in some embodiments, not every one of the residues within the linear epitope need be directly bound (or involved in a bond) by the antigen-binding molecule. In some embodiments, linear epitopes can be from immunizations with a peptide that effectively consisted of the sequence of the linear epitope, or from structural sections of a protein that are relatively isolated from the remainder of the protein (such that the antigen-binding molecule can interact, at least primarily), just with that sequence section.

The terms "antibody" and "antigen-binding molecule" are used interchangeably in the broadest sense and encompass various polypeptides that comprise antibody-like antigen-binding domains, including but not limited to conventional antibodies (typically comprising at least one heavy chain and at least one light chain), single-domain antibodies (sdAbs, comprising just one chain, which is typically similar to a heavy chain), VHH-containing polypeptides (polypeptides comprising at least one heavy chain only antibody variable domain, or VHH), and fragments of any of the foregoing so long as they exhibit the desired antigen-binding activity. In some embodiments, an antibody comprises a dimerization domain. Such dimerization domains include, but are not limited to, heavy chain constant domains (comprising CH1, hinge, CH2, and CH3, where CH1 typically pairs with a light chain constant domain, CL, while the hinge mediates dimerization) and Fc domains (comprising hinge, CH2, and CH3, where the hinge mediates dimerization).

The term antibody also includes, but is not limited to, chimeric antibodies, humanized antibodies, and antibodies of various species such as camelid (including llama), shark, mouse, human, cynomolgus monkey, etc.

The terms "single domain antibody" and "sdAb" are used interchangeably herein to refer to an antibody having a single, monomeric domain, such as a pair of variable domains of heavy chains (or VHH), without a light chain.

The term "VHH" or "VHH domain" or "VHH antigen-binding domain" as used herein refers to the antigen-binding portion of a single-domain antibody, such as a camelid antibody or shark antibody. In some embodiments, a VHH comprises three CDRs and four framework regions, designated FR1, CDR1, FR2, CDR2, FR3, CDR3, and FR4. In some embodiments, a VHH may be truncated at the N-terminus or C-terminus such that it comprise only a partial FR1 and/or FR4, or lacks one or both of those framework regions, so long as the VHH substantially maintains antigen binding and specificity.

The term "VHH-containing polypeptide" refers to a polypeptide that comprises at least one VHH domain. In some embodiments, a VHH polypeptide comprises two, three, or four or more VHH domains, wherein each VHH domain may be the same or different. In some embodiments, a VHH-containing polypeptide comprises an Fc domain. In some such embodiments, the VHH polypeptide may form a dimer. Nonlimiting structures of VHH-containing polypeptides include $VHH_1$-Fc, $VHH_1$-$VHH_2$-Fc, and $VHH_1$-$VHH_2$-$VHH_3$-Fc, wherein $VHH_1$, $VHH_2$, and $VHH_3$ may be the same or different. In some embodiments of such structures, one VHH may be connected to another VHH by a linker, or one VHH may be connected to the Fc by a linker. In some such embodiments, the linker comprises 1-20 amino acids, preferably 1-20 amino acids predominantly composed of glycine and, optionally, serine. In some embodiments, when a VHH-containing polypeptide comprises an Fc, it forms a dimer. Thus, the structure $VHH_1$-$VHH_2$-Fc, if it forms a dimer, is considered to be tetravalent (i.e., the dimer has four VHH domains). Similarly, the structure $VHH_1$-$VHH_2$-$VHH_3$-Fc, if it forms a dimer, is considered to be hexavalent (i.e., the dimer has six VHH domains).

The term "monoclonal antibody" refers to an antibody (including an sdAb or VHH-containing polypeptide) of a substantially homogeneous population of antibodies, that is, the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. Thus, a sample of monoclonal antibodies can bind to the same epitope on the antigen. The modifier "monoclonal" indicates the character of the antibody as being obtained from a substantially homogeneous population of antibodies, and is not to be construed as requiring production of the antibody by any particular method. For example, the monoclonal antibodies may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example.

The term "CDR" denotes a complementarity determining region as defined by at least one manner of identification to one of skill in the art. In some embodiments, CDRs can be defined in accordance with any of the Chothia numbering schemes, the Kabat numbering scheme, a combination of Kabat and Chothia, the AbM definition, and/or the contact definition. A VHH comprises three CDRs, designated CDR1, CDR2, and CDR3.

The term "heavy chain constant region" as used herein refers to a region comprising at least three heavy chain constant domains, $C_H1$, hinge, $C_H2$, and $C_H3$. Of course, non-function-altering deletions and alterations within the domains are encompassed within the scope of the term "heavy chain constant region," unless designated otherwise. Nonlimiting exemplary heavy chain constant regions include γ, δ, and α. Nonlimiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, and an antibody comprising an α constant region is an IgA antibody. Further, an antibody comprising a μ constant region is an IgM antibody, and an antibody comprising an & constant region is an IgE antibody. Certain isotypes can be further subdivided into subclasses. For example, IgG antibodies include, but are not limited to, IgG1 (comprising a $γ_1$ constant region), IgG2 (comprising a $γ_2$ constant region), IgG3 (comprising a $γ_3$ constant region), and IgG4 (comprising a $γ_4$ constant region) antibodies; IgA antibodies include, but are not limited to, IgA1 (comprising an $α_1$ constant region) and IgA2 (comprising an $α_2$ constant region) antibodies; and IgM antibodies include, but are not limited to, IgM1 and IgM2.

A "Fc region" as used herein refers to a portion of a heavy chain constant region comprising CH2 and CH3. In some embodiments, an Fc region comprises a hinge, CH2, and CH3. In various embodiments, when an Fc region comprises a hinge, the hinge mediates dimerization between two Fc-containing polypeptides. An Fc region may be of any antibody heavy chain constant region isotype discussed herein. In some embodiments, an Fc region is an IgG1, IgG2, IgG3, or IgG4.

An "acceptor human framework" as used herein is a framework comprising the amino acid sequence of a heavy chain variable domain ($V_H$) framework derived from a human immunoglobulin framework or a human consensus framework, as discussed herein. An acceptor human framework derived from a human immunoglobulin framework or a human consensus framework can comprise the same amino acid sequence thereof, or it can contain amino acid sequence changes. In some embodiments, the number of amino acid changes are fewer than 10, or fewer than 9, or fewer than 8, or fewer than 7, or fewer than 6, or fewer than 5, or fewer than 4, or fewer than 3, across all of the human frameworks in a single antigen binding domain, such as a VHH.

"Affinity" refers to the strength of the sum total of noncovalent interactions between a single binding site of a molecule (for example, an antibody or VHH-containing polypeptide) and its binding partner (for example, an antigen). The affinity or the apparent affinity of a molecule X for its partner Y can generally be represented by the dissociation constant ($K_D$) or the $K_{D\text{-}apparent}$, respectively. Affinity can be measured by common methods known in the art (such as, for example, ELISA $K_D$, KinExA, flow cytometry, and/or surface plasmon resonance devices), including those described herein. Such methods include, but are not limited to, methods involving BIAcore®, Octet®, or flow cytometry.

The term "$K_D$", as used herein, refers to the equilibrium dissociation constant of an antigen-binding molecule/antigen interaction. When the term "$K_D$" is used herein, it includes $K_D$ and $K_{D\text{-}apparent}$.

In some embodiments, the $K_D$ of the antigen-binding molecule is measured by flow cytometry using an antigen-expressing cell line and fitting the mean fluorescence measured at each antibody concentration to a non-linear one-site binding equation (Prism Software graphpad). In some such embodiments, the $K_D$ is $K_{D\text{-}apparent}$.

The term "biological activity" refers to any one or more biological properties of a molecule (whether present naturally as found in vivo, or provided or enabled by recombinant means). Biological properties include, but are not limited to, binding a ligand, inducing or increasing cell proliferation (such as T cell proliferation), and inducing or increasing expression of cytokines=.

The term "OX40 activity" or "biological activity" of OX40, as used herein, includes any biological effect or at least one of the biologically relevant functions of the OX40 protein. In some embodiments, OX40) activity includes the ability of OX40 to interact or bind to OX40) ligand (OX40L). Nonlimiting exemplary OX40 activities include increasing NFκB signaling, increasing proliferation of CD4$^+$ and/or CD8$^+$ T cells, increasing IFNγ expression in T cells, increasing CD25 and/or CD71 expression on T cells, and reducing the suppressive activity of Treg cells on effector T cell activation and proliferation.

An "agonist" or "activating" antibody (such as a sdAb or VHH-containing polypeptide) is one that increases and/or activates a biological activity of the target antigen. In some embodiments, the agonist antibody binds to an antigen and increases its biologically activity by at least about 20%, 40%, 60%, 80%, 85% or more.

An "antagonist", a "blocking" or "neutralizing" antibody is one that decreases and/or inactivates a biological activity of the target antigen. In some embodiments, the neutralizing antibody binds to an antigen and reduces its biologically activity by at least about 20%, 40%, 60%, 80%, 85% 90%, 95%, 99% or more.

An "affinity matured" VHH-containing polypeptide refers to a VHH-containing polypeptide with one or more alterations in one or more CDRs compared to a parent VHH-containing polypeptide that does not possess such alterations, such alterations resulting in an improvement in the affinity of the VHH-containing polypeptide for antigen.

A "humanized VHH" as used herein refers to a VHH in which one or more framework regions have been substantially replaced with human framework regions. In some instances, certain framework region (FR) residues of the human immunoglobulin are replaced by corresponding non-human residues. Furthermore, the humanized VHH can comprise residues that are found neither in the original VHH nor in the human framework sequences, but are included to further refine and optimize VHH or VHH-containing polypeptide performance. In some embodiments, a humanized VHH-containing polypeptide comprises a human Fc region. As will be appreciated, a humanized sequence can be identified by its primary sequence and does not necessarily denote the process by which the antibody was created.

A "functional Fc region" possesses an "effector function" of a native sequence Fc region. Exemplary "effector functions" include Fc receptor binding; Clq binding and complement dependent cytotoxicity (CDC); Fc receptor binding: antibody-dependent cell-mediated cytotoxicity (ADCC); phagocytosis; down regulation of cell surface receptors (for example B-cell receptor); and B-cell activation, etc. Such effector functions generally require the Fc region to be combined with a binding domain (for example, an antibody variable domain) and can be assessed using various assays.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification. In some embodiments, a "variant Fc region" comprises an amino acid sequence which differs from that of a native sequence Fc region by virtue of at least one amino acid modification, yet retains at least one effector function of the native sequence Fc region. In some embodiments, the variant Fc region has at least one amino acid substitution compared to a native sequence Fc region or to the Fc region of a parent polypeptide, for example, from about one to about ten amino acid substitutions, and preferably, from about one to about five amino acid substitutions in a native sequence Fc region or in the Fc region of the parent polypeptide. In some embodiments, the variant Fc region herein will possess at least about 80% sequence identity with a native sequence Fc region and/or with an Fc region of a parent polypeptide, at least about 90% sequence identity therewith, at least about 95%, at least about 96%, at least about 97%, at least about 98%, or at least about 99% sequence identity therewith.

"Fc receptor" or "FcR" describes a receptor that binds to the Fc region of an antibody. In some embodiments, an FcγR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain, (See, for example, Daeron, Annu. Rev. Immunol. 15:203-234 (1997)). FcRs are reviewed, for example, in Ravetch and Kinet. *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. For example, the term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, for example, Ghetie and Ward, *Immunol. Today* 18(12):592-598 (1997); Ghetie et al., *Nature Biotechnology,* 15(7):637-640) (1997); Hinton et al., *J. Biol. Chem.* 279(8):6213-6216 (2004); WO 2004/92219 (Hinton et al.).

The term "substantially similar" or "substantially the same." as used herein, denotes a sufficiently high degree of similarity between two or more numeric values such that one of skill in the art would consider the difference between the two or more values to be of little or no biological and/or statistical significance within the context of the biological characteristic measured by said value. In some embodiments the two or more substantially similar values differ by no more than about any one of 5%, 10%, 15%, 20%, 25%, or 50%.

A polypeptide "variant" means a biologically active polypeptide having at least about 80% amino acid sequence identity with the native sequence polypeptide after aligning the sequences and introducing gaps, if necessary, to achieve the maximum percent sequence identity, and not considering any conservative substitutions as part of the sequence identity. Such variants include, for instance, polypeptides wherein one or more amino acid residues are added, or deleted, at the N- or C-terminus of the polypeptide. In some embodiments, a variant will have at least about 80% amino acid sequence identity. In some embodiments, a variant will have at least about 90% amino acid sequence identity. In some embodiments, a variant will have at least about 95% amino acid sequence identity with the native sequence polypeptide.

As used herein, "percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

An amino acid substitution may include but are not limited to the replacement of one amino acid in a polypeptide with another amino acid. Exemplary substitutions are shown in Table 1. Amino acid substitutions may be introduced into an antibody of interest and the products screened for a desired activity, for example, retained/improved antigen binding, decreased immunogenicity, or improved ADCC or CDC.

TABLE 1

| Original Residue | Exemplary Substitutions |
|---|---|
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "vector" is used to describe a polynucleotide that can be engineered to contain a cloned polynucleotide or polynucleotides that can be propagated in a host cell. A vector can include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that can be used in colorimetric assays, for example, β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NSO cells, PER.C6® cells (Crucell), and 293 and CHO cells, and their derivatives, such as 293-6E, CHO-DG44, CHO-K1, CHO-S, and CHO-DS cells. Host cells include progeny of a single host cell, and the progeny may not necessarily be completely identical (in morphology or in genomic DNA complement) to the original parent cell due to natural, accidental, or deliberate mutation. Host cells also include primary cells, such as primary human immune cells.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, for example, in the case of an RNA polynucleotide. Thus, a DNA polynucleotide that is contained in a vector inside a host cell may be referred to as "isolated".

The terms "individual" and "subject" are used interchangeably herein to refer to an animal; for example a mammal. In some embodiments, methods of treating mammals, including, but not limited to, humans, rodents, simians, felines, canines, equines, bovines, porcines, ovines, caprines, mammalian laboratory animals, mammalian farm animals, mammalian sport animals, and mammalian pets, are provided. In some examples, an "individual" or "subject" refers to an individual or subject in need of treatment for a disease or disorder. In some embodiments, the subject to receive the treatment can be a patient, designating the fact that the subject has been identified as having a disorder of relevance to the treatment, or being at adequate risk of contracting the disorder.

A "disease" or "disorder" as used herein refers to a condition where treatment is needed and/or desired.

The term "tumor cell", "cancer cell", "cancer", "tumor", and/or "neoplasm", unless otherwise designated, are used herein interchangeably and refer to a cell (or cells) exhibiting an uncontrolled growth and/or abnormal increased cell survival and/or inhibition of apoptosis which interferes with the normal functioning of bodily organs and systems. Included in this definition are benign and malignant cancers, polyps, hyperplasia, as well as dormant tumors or micrometastases.

The terms "cancer" and "tumor" encompass solid and hematological/lymphatic cancers and also encompass malignant, pre-malignant, and benign growth, such as dysplasia. Also, included in this definition are cells having abnormal proliferation that is not impeded (e.g. immune evasion and immune escape mechanisms) by the immune system (e.g. virus infected cells). Exemplary cancers include, but are not limited to: basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intraepithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL: high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

The term "non-tumor cell" as used herein refers to a normal cells or tissue. Exemplary non-tumor cells include, but are not limited to: T-cells, B-cells, natural killer (NK) cells, natural killer T (NKT) cells, dendritic cells, monocytes, macrophages, epithelial cells, fibroblasts, hepatocytes, interstitial kidney cells, fibroblast-like synoviocytes, osteoblasts, and cells located in the breast, skeletal muscle, pancreas, stomach, ovary, small intestines, placenta, uterus, testis, kidney, lung, heart, brain, liver, prostate, colon, lymphoid organs, bone, and bone-derived mesenchymal stem cells. The term "a cell or tissue located in the periphery" as used herein refers to non-tumor cells not located near tumor cells and/or within the tumor microenvironment.

The term "cells or tissue within the tumor microenvironment" as used herein refers to the cells, molecules, extracellular matrix and/or blood vessels that surround and/or feed a tumor cell. Exemplary cells or tissue within the tumor microenvironment include, but are not limited to: tumor vasculature; tumor-infiltrating lymphocytes; fibroblast reticular cells; endothelial progenitor cells (EPC); cancer-associated fibroblasts; pericytes; other stromal cells; components of the extracellular matrix (ECM); dendritic cells; antigen presenting cells; T-cells; regulatory T-cells (Treg cells); macrophages; neutrophils; myeloid-derived suppressor cells (MDSCs) and other immune cells located proximal to a tumor. Methods for identifying tumor cells, and/or cells/tissues located within the tumor microenvironment are well known in the art, as described herein, below.

In some embodiments, an "increase" or "decrease" refers to a statistically significant increase or decrease, respectively. As will be clear to the skilled person, "modulating" can also involve effecting a change (which can either be an increase or a decrease) in affinity, avidity, specificity and/or selectivity of a target or antigen, for one or more of its ligands, binding partners, partners for association into a homomultimeric or heteromultimeric form, or substrates; effecting a change (which can either be an increase or a decrease) in the sensitivity of the target or antigen for one or more conditions in the medium or surroundings in which the target or antigen is present (such as pH, ion strength, the presence of co-factors, etc.); and/or cellular proliferation or cytokine production, compared to the same conditions but without the presence of a test agent. This can be determined in any suitable manner and/or using any suitable assay known per se or described herein, depending on the target involved.

As used herein, "an immune response" is meant to encompass cellular and/or humoral immune responses that are sufficient to inhibit or prevent onset or ameliorate the symptoms of disease (for example, cancer or cancer metastasis). "An immune response" can encompass aspects of both the innate and adaptive immune systems.

As used herein. "treatment" is an approach for obtaining beneficial or desired clinical results. "Treatment" as used herein, covers any administration or application of a therapeutic for disease in a mammal, including a human. For purposes of this disclosure, beneficial or desired clinical results include, but are not limited to, any one or more of: alleviation of one or more symptoms, diminishment of extent of disease, preventing or delaying spread (for example, metastasis, for example metastasis to the lung or to the lymph node) of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods provided herein contemplate any one or more of these aspects of treatment. In-line with the above, the term treatment does not require one-hundred percent removal of all aspects of the disorder.

"Ameliorating" means a lessening or improvement of one or more symptoms as compared to not administering a therapeutic agent. "Ameliorating" also includes shortening or reduction in duration of a symptom.

The term "anti-cancer agent" is used herein in its broadest sense to refer to agents that are used in the treatment of one or more cancers. Exemplary classes of such agents in include, but are not limited to, chemotherapeutic agents, anti-cancer biologics (such as cytokines, receptor extracellular domain-Fc fusions, and antibodies), radiation therapy, CAR-T therapy, therapeutic oligonucleotides (such as antisense oligonucleotides and siRNAs) and oncolytic viruses.

The term "biological sample" means a quantity of a substance from a living thing or formerly living thing. Such substances include, but are not limited to, blood, (for example, whole blood), plasma, serum, urine, amniotic fluid, synovial fluid, endothelial cells, leukocytes, monocytes, other cells, organs, tissues, bone marrow, lymph nodes and spleen.

The term "control" or "reference" refers to a composition known to not contain an analyte ("negative control") or to contain an analyte ("positive control"). A positive control can comprise a known concentration of analyte.

The terms "inhibition" or "inhibit" refer to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to a reference. In some embodiments, by "reduce" or "inhibit" is meant the ability to cause an overall decrease of 10% or greater. In some embodiments, by "reduce" or "inhibit" is meant the ability to cause an overall decrease of 50% or greater. In some embodiments, by "reduce" or "inhibit" is meant the ability to cause an overall decrease of 75%, 85%, 90%, 95%, or greater. In some embodiments, the amount noted above is inhibited or decreased over a period of time, relative to a control over the same period of time.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. Unless otherwise specified, the terms "reduce", "inhibit", or "prevent" do not denote or require complete prevention over all time, but just over the time period being measured.

A "therapeutically effective amount" of a substance/molecule, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A therapeutically effective amount may be delivered in one or more administrations. A therapeutically effective amount refers to an amount effective, at dosages and for periods of time necessary, to achieve the desired therapeutic and/or prophylactic result.

The terms "pharmaceutical formulation" and "pharmaceutical composition" refer to a preparation which is in such form as to permit the biological activity of the active ingredient(s) to be effective, and which contains no additional components which are unacceptably toxic to a subject to which the formulation would be administered. Such formulations may be sterile.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and are compatible with other ingredients of the formulation. The pharmaceutically acceptable carrier is appropriate for the formulation employed.

Administration "in combination with" one or more further therapeutic agents includes simultaneous (concurrent) and sequential administration in any order.

The term "concurrently" is used herein to refer to administration of two or more therapeutic agents, where at least part of the administration overlaps in time, or where the administration of one therapeutic agent falls within a short period of time relative to administration of the other therapeutic agent, or wherein the therapeutic effect of both agents overlap for at least a period of time.

The term "sequentially" is used herein to refer to administration of two or more therapeutic agents that does not overlap in time, or wherein the therapeutic effects of the agents do not overlap.

As used herein, "in conjunction with" refers to administration of one treatment modality in addition to another treatment modality. As such, "in conjunction with" refers to administration of one treatment modality before, during, or after administration of the other treatment modality to the individual.

The term "package insert" is used to refer to instructions customarily included in commercial packages of therapeutic products, that contain information about the indications, usage, dosage, administration, combination therapy, contraindications and/or warnings concerning the use of such therapeutic products.

An "article of manufacture" is any manufacture (for example, a package or container) or kit comprising at least one reagent, for example, a medicament for treatment of a disease or disorder (for example, cancer), or a probe for specifically detecting a biomarker described herein. In some embodiments, the manufacture or kit is promoted, distributed, or sold as a unit for performing the methods described herein.

The terms "label" and "detectable label" mean a moiety attached, for example, to an antibody or antigen to render a reaction (for example, binding) between the members of the specific binding pair, detectable. The labeled member of the specific binding pair is referred to as "detectably labeled." Thus, the term "labeled binding protein" refers to a protein with a label incorporated that provides for the identification of the binding protein. In some embodiments, the label is a detectable marker that can produce a signal that is detectable by visual or instrumental means, for example, incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Examples of labels for polypeptides include, but are not limited to, the following: radioisotopes or radionuclides (for example, $^{3}$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm); chromogens, fluorescent labels (for example, FITC, rhodamine, lanthanide phosphors), enzymatic labels (for example, horseradish peroxidase, luciferase, alkaline phosphatase); chemiluminescent markers; biotinyl groups; predetermined polypeptide epitopes recognized by a secondary reporter (for example, leucine zipper pair sequences, binding sites for secondary antibodies, metal binding domains, epitope tags), and magnetic agents, such as gadolinium chelates. Representative examples of labels commonly employed for immunoassays include moieties that produce light, for example, acridinium compounds, and moieties that produce fluorescence, for example, fluorescein. In this regard, the moiety itself may not be detectably labeled but may become detectable upon reaction with yet another moiety.

Exemplary OX40-Binding Polypeptides

Agonist OX40-binding polypeptides are provided herein. In various embodiments, the agonist OX40-binding polypeptides comprise at least one VHH domain that binds OX40. In some embodiments, an agonist OX40-binding polypeptide provided herein comprises one, two, three, four, five, six, seven, or eight VHH domains that bind OX40. In some embodiments, an agonist OX40-binding polypeptide provided herein comprises one, two, three, or four VHH domains that bind OX40. Such OX40-binding polypeptides may comprise one or more additional VHH domains that bind one or more target proteins other than OX40.

In some embodiments, an agonist OX40-binding polypeptide comprises at least one VHH domain that binds OX40 and an Fc domain. In some embodiments, an agonist OX40-binding polypeptide provided herein comprises one, two, three, or four VHH domains that bind OX40) and an Fc domain. In some embodiments, an Fc domain mediates dimerization of the OX40-binding polypeptide at physiological conditions such that a dimer is formed that doubles the number of OX40 binding sites. For example, an OX40-binding polypeptide comprising three VHH domains that bind OX40 and an Fc region is trivalent as a monomer, but at physiological conditions, the Fc region may mediate dimerization, such that the OX40-binding polypeptide exists as a hexavalent dimer under such conditions. Nonlimiting exemplary hexavalent OX-40 binding polypeptides include 3x1D10v1-Fc and 3x1D10v6-Fc, which are also referred to as Hex-1D10v1 and Hex-1D10v6, respectively. Without intending to be bound by any particular theory, it is thought that co-stimulation through OX40 is improved by clustering OX40, meaning that multivalent OX40-binding polypeptides (such as tetravalent or hexavalent) are more effective than monovalent or bivalent OX40-binding polypeptides.

In various embodiments, a VHH domain that binds OX40 comprises a CDR1 comprising the amino acid sequence of SEQ ID NO: 10, a CDR2 comprising the amino acid sequence of SEQ ID NO: 11, and a CDR3 comprising the amino acid sequence of SEQ ID NO: 12. In some embodiments, the VHH domain is humanized.

In some embodiments, a VHH domain that binds OX40 may be humanized. Humanized antibodies (such as VHH-containing polypeptides) are useful as therapeutic molecules because humanized antibodies reduce or eliminate the human immune response to non-human antibodies, which can result in an immune response to an antibody therapeutic, and decreased effectiveness of the therapeutic. Generally, a humanized antibody comprises one or more variable domains in which CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (for example, the antibody from which the CDR residues are derived), for example, to restore or improve antibody specificity or affinity.

Humanized antibodies and methods of making them are reviewed, for example, in Almagro and Fransson. (2008) *Front. Biosci.* 13:1619-1633, and are further described, for example, in Riechmann et al., (1988) *Nature* 332:323-329; Queen et al., (1989) *Proc. Natl Acad. Sci. USA* 86:10029-10033; U.S. Pat. Nos. 5,821,337, 7,527,791, 6,982,321, and 7,087,409; Kashmiri et al., (2005) *Methods* 36:25-34; Padlan, (1991) *Mol. Immunol.* 28:489-498 (describing "resurfacing"); Dall'Acqua et al., (2005) *Methods* 36:43-60 (describing "FR shuffling"); and Osbourn et al., (2005) *Methods* 36:61-68 and Klimka et al., (2000) *Br. J. Cancer,* 83:252-260) (describing the "guided selection" approach to FR shuffling).

Human framework regions that can be used for humanization include but are not limited to: framework regions selected using the "best-fit" method (see, for example, Sims et al. (1993) *J. Immunol.* 151:2296); framework regions derived from the consensus sequence of human antibodies of a particular subgroup of heavy chain variable regions (see, for example, Carter et al. (1992) *Proc. Natl. Acad. Sci. USA.* 89:4285: and Presta et al. (1993) *J. Immunol.* 151:2623); human mature (somatically mutated) framework regions or human germline framework regions (see, for example, Almagro and Fransson. (2008) *Front. Biosci.* 13:1619-1633); and framework regions derived from screening FR libraries (see, for example, Baca et al., (1997) *J. Biol. Chem.* 272:10678-10684 and Rosok et al., (1996) *J. Biol. Chem.* 271:22611-22618). Typically, the FR regions of a VHH are replaced with human FR regions to make a humanized VHH. In some embodiments, certain FR residues of the human FR are replaced in order to improve one or more properties of the humanized VHH. VHH domains with such replaced residues are still referred to herein as "humanized."

In some embodiments, a VHH domain that binds OX40 comprises a CDR1 comprising the amino acid sequence of SEQ ID NO: 10, a CDR2 comprising the amino acid sequence of SEQ ID NO: 11, and a CDR3 comprising the amino acid sequence of SEQ ID NO: 12; and a framework 2 (FR2) comprising the amino acid sequence of SEQ ID NO: 22. In some embodiments, the VHH domain further comprises a FR3 comprising the amino acid sequence of SEQ ID NO: 23.

In some embodiments, an OX40-binding polypeptide comprises at least one VHH domain comprising the amino acid sequence of SEQ ID NO: 9. In some embodiments, an OX40-binding polypeptide comprises one, two, three, or four VHH domains comprising the amino acid sequence of SEQ ID NO: 9.

In some embodiments, an OX40-binding polypeptide comprises three VHH domains that bind OX40 and an Fc domain. In some such embodiments, each VHH domain comprises a CDR1 comprising the amino acid sequence of SEQ ID NO: 10, a CDR2 comprising the amino acid sequence of SEQ ID NO: 11, and a CDR3 comprising the amino acid sequence of SEQ ID NO: 12. In some embodiments, each VHH domain comprises a CDR1 comprising the amino acid sequence of SEQ ID NO: 10, a CDR2 comprising the amino acid sequence of SEQ ID NO: 11, and a CDR3 comprising the amino acid sequence of SEQ ID NO: 12: and a framework 2 (FR2) comprising the amino acid sequence of SEQ ID NO: 22. In some embodiments, each VHH domain further comprises a FR3 comprising the amino acid sequence of SEQ ID NO: 23. In some embodiments, each VHH domain comprises the amino acid sequence of SEQ ID NO: 9.

In various embodiments, an Fc domain included in an OX40-binding polypeptide is a human Fc domain, or is derived from a human Fc domain.

In some embodiments, an Fc domain included in an OX40-binding polypeptide is derived from a human Fc domain, and comprises a three amino acid deletion in the lower hinge corresponding to IgG1 E233, L234, and L235, herein referred to as "Fc xELL." Fc xELL polypeptides do not engage FcγRs and thus are referred to as "effector silent" or "effector null", however in some embodiments, xELL Fc domains bind FcRn and therefore have extended half-life and transcytosis associated with FcRn mediated recycling.

In some embodiments, the Fc domain included in an OX40-binding polypeptide is derived from a human Fc domain and comprises mutations M252Y and M428V, herein referred to as "Fc-YV". In some embodiments, such mutations enhance binding to FcRn at the acidic pH of the endosome (near 6.5), while losing detectable binding at neutral pH (about 7.2), allowing for enhanced FcRn mediated recycling and extended half-life.

In some embodiments, the Fc domain included in an OX40-binding polypeptide is derived from a human Fc domain and comprises mutations designed for heterodimerization, herein referred to as "knob" and "hole". In some embodiments, the "knob" Fc domain comprises the mutation T366W. In some embodiments, the "hole" Fc domain comprises mutations T366S, L368A, and Y407V. In some embodiments, Fc domains used for heterodimerization comprise additional mutations, such as the mutation S354C on a first member of a heterodimeric Fc pair that forms an asymmetric disulfide with a corresponding mutation Y349C on the second member of a heterodimeric Fc pair. In some embodiments, one member of a heterodimeric Fc pair comprises the modification H435R or H435K to prevent protein A binding while maintaining FcRn binding. In some embodiments, one member of a heterodimeric Fc pair comprises the modification H435R or H435K, while the second member of the heterodimeric Fc pair is not modified at H435. In various embodiments, the hold Fc domain comprises the modification H435R or H435K (referred to as "hole-R" in some instances when the modification is H435R), while the knob Fc domain does not. In some instances, the hole-R mutation improves purification of the heterodimer over homodimeric hole Fc domains that may be present.

Nonlimiting exemplary Fc domains that may be used in an OX40-binding polypeptide include Fc domains comprising the amino acid sequences of SEQ ID NOs: 25 and 26.

In some embodiments, an OX40-binding polypeptide that comprises three VHH domains and an Fc domain comprise the amino acid sequence of SEQ ID NO: 14 and an Fc domain fused to the C-terminus of that amino acid sequence. In some embodiments, an OX40-binding polypeptide that comprises three VHH domains and an Fc domain comprise the amino acid sequence of SEQ ID NO: 15. In some embodiments, the OX40-binding polypeptide consists of the amino acid sequence of SEQ ID NO: 15.

Exemplary Activities of OX40-Binding Polypeptides

In various embodiments, the OX40-binding polypeptides provided herein are agonists of OX40 activity. Agonist activity may be determined, in some embodiments, using the methods provided in the Examples herein, such as using Jurkat/OX40 reporter cells or similar cells.

In some embodiments, the OX40-binding polypeptides provided herein increase proliferation of $CD4^+$ and/or $CD8^+$ T cells in vitro and/or in vivo. In some embodiments, an OX40-binding polypeptide provided herein increases $CD4^+$ and/or $CD8^+$ T cells proliferation in vitro. In some embodiments, the OX40-binding polypeptide increases $CD4^+$ and/or $CD8^+$ T cells proliferation by at least 1.5-fold or at least 2-fold. The increase in proliferation of $CD4^+$ and/or $CD8^+$ T cells may be determined by any method in the art, such as for example, the methods provided in the Examples herein. A nonlimiting exemplary assay is as follows. $CD4^+$ and/or $CD8^+$ T cells may be isolated from one or more healthy human donors and stained with CellTrace Violet (CTV). The T cells are then co-stimulated with anti-CD3 antibody and an OX40-binding polypeptide, and then analyzed by FACS. Loss of CTV staining indicates proliferation. In some embodiments, an increase in $CD4^+$ and/or $CD8^+$ T cell proliferation is determined as an average from a set of experiments or from pooled T cells, such as by measuring proliferation of $CD4^+$ and/or $CD8^+$ T cells isolated from different healthy human donors. In some embodiments, an increase in $CD4^+$ and/or $CD8^+$ T cell proliferation is determined as an average from experiments carried out using T cells from at least five or at least ten different healthy donors, or from a pool of T cells from at least five or at least ten different healthy donors. In some embodiments, the OX40-binding polypeptides provided herein increase proliferation of $CD4^+$ and/or $CD8^+$ T cells even in the presence of Treg cells.

In some embodiments, the OX40-binding polypeptides provided herein increase CD25 expression on $CD4^+$ and/or $CD8^+$ T cells in vitro and/or in vivo. CD25 expression indicates T cell activation. In some embodiments, an OX40-binding polypeptide provided herein increases CD25 expression on $CD4^+$ and/or $CD8^+$ T cells in vitro. In some embodiments, the OX40-binding polypeptide increases CD25 expression on $CD4^+$ and/or $CD8^+$ T cells by at least 1.5-fold or at least 2-fold. The increase in CD25 expression on $CD4^+$ and/or $CD8^+$ T cells may be determined by any method in the art, such as for example, the methods provided in the Examples herein. A nonlimiting exemplary assay is as follows. $CD4^+$ and/or $CD8^+$ T cells may be isolated from one or more healthy human donors and co-stimulated with anti-CD3 antibody and an OX40-binding polypeptide, and then analyzed by FACS for CD25 expression. In some embodiments, an increase in CD25 expression on $CD4^+$ and/or $CD8^+$ T cell proliferation is determined as an average from a set of experiments or from pooled T cells, such as by measuring CD25 expression on $CD4^+$ and/or $CD8^+$ T cells isolated from different healthy human donors. In some embodiments, an increase in CD25 expression on $CD4^+$ and/or $CD8^+$ T cells is determined as an average from experiments carried out using T cells from at least five or at least ten different healthy donors, or from a pool of T cells from at least five or at least ten different healthy donors. In some embodiments, the OX40-binding polypeptides provided herein increase CD25 expression on $CD4^+$ and/or $CD8^+$ T cells even in the presence of Treg cells.

In some embodiments, the OX40-binding polypeptides provided herein increase CD71 expression on $CD4^+$ and/or $CD8^+$ T cells in vitro and/or in vivo. CD71 expression indicates T cell activation. In some embodiments, an OX40-binding polypeptide provided herein increases CD71 expression on $CD4^+$ and/or $CD8^+$ T cells in vitro. In some embodiments, the OX40-binding polypeptide increases CD71 expression on $CD4^+$ and/or $CD8^+$ T cells by at least 1.5-fold or at least 2-fold. The increase in CD71 expression on $CD4^+$ and/or $CD8^+$ T cells may be determined by any method in the art, such as for example, the methods provided in the Examples herein. A nonlimiting exemplary assay is as follows. $CD4^+$ and/or $CD8^+$ T cells may be isolated from one or more healthy human donors and co-stimulated with anti-CD3 antibody and an OX40-binding polypeptide, and then analyzed by FACS for CD71 expression. In some embodiments, an increase in CD71 expression on $CD4^+$ and/or $CD8^+$ T cell proliferation is determined as an average from a set of experiments or from pooled T cells, such as by measuring CD71 expression on $CD4^+$ and/or $CD8^+$ T cells isolated from different healthy human donors. In some embodiments, an increase in CD71 expression on $CD4^+$ and/or $CD8^+$ T cells is determined as an average from experiments carried out using T cells from at least five or at least ten different healthy donors, or from a pool of T cells from at least five or at least ten different healthy donors. In some embodiments, the OX40-binding polypeptides provided herein increase CD71 expression on $CD4^+$ and/or $CD8^+$ T cells even in the presence of Treg cells.

In some embodiments, the OX40-binding polypeptides provided herein increase IFNγ expression in $CD4^+$ and/or $CD8^+$ T cells in vitro and/or in vivo. IFNγ expression indicates T cell activation. In some embodiments, an OX40-binding polypeptide provided herein increases IFNγ expression in $CD4^+$ and/or $CD8^+$ T cells in vitro. In some embodiments, the OX40-binding polypeptide increases IFNγ expression on $CD4^+$ and/or $CD8^+$ T cells by at least 1.5-fold, at least 2-fold, at least 3-fold, or by at least 5-fold. The increase in IFNγ expression in $CD4^+$ and/or $CD8^+$ T cells may be determined by any method in the art, such as for example, the methods provided in the Examples herein. A nonlimiting exemplary assay is as follows. $CD4^+$ and/or $CD8^+$ T cells may be isolated from one or more healthy human donors and co-stimulated with anti-CD3 antibody and an OX40-binding polypeptide. To determine intracellular IFNγ expression, cells are pelleted and surface-labeled with detectable anti-$CD4^+$ and anti-CD8 antibodies. Cells are then fixed and permeablized, and then stained with detectable anti-IFNγ antibody. IFNγ $CD4^+$ or IFNγ $CD8^+$ cells are then detected by FACS. In some embodiments, an increase in IFNγ expression on CD4+ and/or CD8+ T cell proliferation is determined as an average from a set of experiments or from pooled T cells, such as by measuring IFNγ expression in CD4+ and/or CD8+ T cells isolated from different healthy human donors. In some embodiments, an increase in IFNγ expression in CD4+ and/or CD8+ T cells is determined as an average from experiments carried out using T cells from at least five or at least ten different healthy donors, or from a pool of T cells from at least five or at least ten different healthy donors. In some embodiments, the OX40)-binding polypeptides provided herein increase IFNγ expression in CD4+ and/or CD8+ T cells even in the presence of Treg cells.

In some embodiments, the OX40-binding polypeptides provided herein reduce or attenuate suppressive activity of regulatory T-cells (Tregs). In some embodiments, the OX40-binding polypeptide reduce Treg suppressive activity on CD4+ and/or CD8+ T cells by at least 10%, at least 20%, at least 30%, or by at least 50%. The decrease in Treg suppressive activity on conventional CD4+ and/or CD8+ T cells may be determined by any method in the art, such as for example, the methods provided in the Examples herein. A nonlimiting exemplary assay is as follows. Tregs and CD4+ T-cells are differentially labeled with fluorescent proliferative cellular dyes following isolation from healthy human donor PBMCs. CD4+ T-cells are stimulated with anti-CD3 antibody, while Treg cells are incubated in the presence of an OX40-binding polypeptides provided herein. The two T-cell populations are co-cultured for 3 days and proliferation and activation of CD4+ T-cells is monitored by flow cytometry. In some embodiments, the OX40-binding polypeptides provided herein increases CD4+ and/or CD8+ T-cell activation and proliferation in the presence of Treg cells, for example, compared to CD4+ and/or CD8+ T-cell activation and proliferation in the presence of Treg cells but the absence of an OX40-binding polypeptide provided herein.

In some embodiments, the OX40-binding polypeptide is multivalent, comprising more than one OX40 binding domain. In various embodiments, the OX40-binding polypeptide comprises two, three, four, five, six, seven, or eight OX40 binding domains. In some such embodiments, at least one, or all of the OX40 binding domains are the same. In some such embodiments, all of the OX40 binding domains comprise CDR1, CDR2, and CDR3 of 1D10v6 (SEQ ID NOs: 10, 11, and 12, respectively). In some embodiments, at least one, or all of the OX40 binding domains comprise the 1D10v6 VHH (SEQ ID NO: 9). In some embodiments, at least one OX40 binding domains comprises the CDRs or VHH of 1D10v6 and at least one OX40 binding domain does not comprise the CDRs or VHH of 1D10v6. In some embodiments, an OX40-binding polypeptide is multispecific, comprising at least one domain that binds OX40 and at least one domain that binds another antigen. In some embodiments, the second antigen is selected from PD1, PDL1, CTLA4, TIGIT, LAG3, VISTA, gpNMB, B7H3, B7H4, HHLA2, CD73, CD39, 41BB, GITR, CD28, ICOS, HVEM, 5T4, Alpha-4 integrin, Alpha-V integrin, alpha4beta1 integrin, alpha4beta7 integrin, AGR2, Anti-Lewis-Y, Apelin J receptor, APRIL, B7-H3, B7-H4, B7-H6, BAFF, BTLA, C5 complement, C-242, CA9, CA19-9, (Lewis a), Carbonic anhydrase 9, CD2, CD3, CD6, CD9, CD11a, CD19, CD20, CD22, CD24, CD25, CD27, CD28, CD30, CD33, CD38, CD40, CD40L, CD41, CD44, CD44v6, CD47, CD51, CD52, CD56, CD64, CD70, CD71, CD74, CD80, CD81, CD86, CD95, CD117, CD123, CD125, CD132, (IL-2RG), CD133, CD138, CD166, CD172A, CD248, CDH6, CEACAM5 (CEA), CEACAM6 (NCA-90), CLAUDIN-3, CLAUDIN-4, cMet, Collagen, Cripto, CSFR, CSFR-1, CTLA-4, CTGF, CXCL10, CXCL13, CXCR1, CXCR2, CXCR4, CYR61, DL44, DLK1, DLL3, DLL4, DPP-4, DSG1, EDA, EDB, EGFR, EGFRviii, Endothelin B receptor (ETBR), ENPP3, EpCAM, EPHA2, EPHB2, ERBB3, F protein of RSV, FAP, FGF-2, FGF8, FGFR1, FGFR2, FGFR3, FGFR4, Fibronectin extra-domain B (EDB), FLT-3, Folate receptor alpha (FRα), GAL3ST1, G-CSF, G-CSFR, GD2, GITR, GLUT1, GLUT4, GM-CSF, GM-CSFR, GP IIb/IIIa receptors, Gp130, GPIIB/IIIA, GPNMB, GRP78, HER2/neu, HER3, HER4, HGF, hGH, HVEM, Hyaluronidase, IFNalpha, IFNbeta, IFNgamma, IgE, IgE Receptor (FceRI), IGF, IGF1R, IL1B, IL1R, IL2, IL11, IL 12, IL 12p40, IL-12R, IL-12Rbeta1, IL13, IL13R, IL15, IL17, IL18, IL21, IL23, IL23R, IL27/IL27R (wsx1), IL29, IL-31R, IL31/IL31R, IL2R, IL4, IL4R, IL6, IL6R, Insulin Receptor, Jagged Ligands, Jagged 1, Jagged 2, KISS1-R, LAG-3, LIF-R, Lewis X, LIGHT, LRP4, LRRC26, Ly6G6D, LyPD1, MCSP, Mesothelin, MRP4, MUC1, Mucin-16 (MUC16, CA-125), Na/K ATPase, NGF, NEctin 4, Nicastrin, Notch Receptors, Notch 1, Notch 2, Notch 3, Notch 4, NOV, OSM-R, OX-40, PAR2, PDGF-AA, PDGF-BB, PDGFRalpha, PDGFRbeta, PD-1, PD-L1, PD-L2, Phosphatidyl-serine, P1GF, PSCA, PSMA, PSGR, RAAG12, RAGE, SLC44A4, Sphingosine 1 Phosphate, STEAP1, STEAP2, TAG-72, TAPA1, TEM-8, TGFbeta, TIGIT, TIM-3, TLR2, TLR4, TLR6, TLR7, TLR8, TLR9, TMEM31, TNFalpha, TNFR, TNFRS12A, TRAIL-R1, TRAIL-R2, Transferrin, Transferrin receptor, TRK-A, TRK-B, uPAR, VAP1, VCAM-1, VEGF, VEGF-A, VEGF-B, VEGF-C, VEGF-D, VEGFR1, VEGFR2, VEGFR3, VISTA, WISP-1, WISP-2, and WISP-3. In some embodiments, the at least one binding domain that binds a second antigen is an antagonist or an agonist. In some embodiments, the at least one binding domain that binds a second antigen is a VHH domain.

Provided herein are engineered cells that express an OX40-binding polypeptide provided herein. In some embodiments, the OX40-binding polypeptide is secreted from the cell. In some embodiments, the OX40-binding polypeptide comprises a signal peptide, e.g., an antibody signal peptide or other signal sequence that causes the polypeptide to be secreted by a cell. The signal peptide, or a portion of the signal peptide, may be cleaved from the polypeptide when it is secreted. In some embodiments, an OX40-binding polypeptide may be encoded by a nucleic acid in a cell, and then expressed and secreted by the cell. The nucleic acid typically contains suitable regulatory sequences (such as, for example, promoters and/or enhancers) for expression under desired conditions. The nucleic acid may be incorporated into the genome of the cell, or may be present as extra-genomic nucleic acid. In some embodiments, the cell is an immune cell, such as, for example, a primary immune cell.

In some embodiments, the OX40-binding polypeptide is a chimeric antigen receptor (CAR). CARs are synthetic receptors typically containing an extracellular targeting or binding moiety, such as an antigen binding domain, a transmembrane domain, and one or more signaling domains in a fusion molecule that is expressed on the surface of a cell, such as a T cell. Thus, CARs combine antigen-specificity and T cell activating properties in a single molecule. First generation CARs typically include the cytoplasmic region of the CD3zeta or Fc 1 receptor γ chain as their signaling domain. First generation CARs have been tested in phase I clinical studies in patients with ovarian cancer, renal cancer, lymphoma, and neuroblastoma, where they have induced modest responses (reviewed in Sadelain et al., Curr Opin Immunol, 21 (2): 215-223, 2009). Second generation CARs, which contain the signaling domains of a costimulatory molecule, such as CD28, and CD3zeta, provide dual signaling to direct combined activating and co-stimulatory signals. Third generation CARs are more complex with three or more signaling domains (reviewed in Sadelain et al., Cancer Discovery (3), 388-398, 2013 and Dotti et al. Immuno. Rev, 257 (1), 1-36, 2014).

In some embodiments, the extracellular binding moiety of a CAR comprises one or more binding domains, such as VHH domains, that bind OX40. In some embodiments, the extracellular binding moiety is multivalent, comprising more than one binding domain that binds OX40. In various embodiments, the extracellular binding moiety comprises two, three, four, five, six, seven, or eight OX40-binding domains. In some such embodiments, at least one, or all of the OX40-binding domains are the same. In some such embodiments, all of the OX40-binding domains comprise CDR1, CDR2, and CDR3 of 1D10v6 (SEQ ID NOs: 10, 11, and 12, respectively). In some embodiments, at least one, or all of the OX40-binding domains comprise the 1D10v6 VHH (SEQ ID NO: 9). In some embodiments, at least one OX40-binding domain comprises the CDRs or VHH of 1D10v6 and at least one OX40-binding domain does not comprise the CDRs or VHH of 1D10v6. In some embodiments, the extracellular binding moiety is multispecific, comprising at least one domain that binds OX40 and at least one domain that binds another antigen. In some embodiments, the second antigen is selected from PD1, PDL1, CTLA4, TIGIT, LAG3, VISTA, gpNMB., B7H3, B7H4, HHLA2, CD73, CD39, 41BB, GITR, CD28, ICOS, HVEM, 5T4, Alpha-4 integrin, Alpha-V integrin, alpha4beta1 integrin, alpha4beta7 integrin, AGR2, Anti-Lewis-Y, Apelin J receptor, APRIL, B7-H3, B7-H4, B7-H6, BAFF, BTLA, C5 complement, C-242, CA9, CA19-9, (Lewis a), Carbonic anhydrase 9, CD2, CD3, CD6, CD9, CD11a, CD19, CD20, CD22, CD24, CD25, CD27, CD28, CD30, CD33, CD38, CD40, CD40L, CD41, CD44, CD44v6, CD47, CD51, CD52, CD56, CD64, CD70, CD71, CD74, CD80, CD81, CD86, CD95, CD117, CD123, CD125, CD132, (IL-2RG), CD133, CD138, CD166, CD172A, CD248, CDH6, CEACAM5 (CEA), CEACAM6 (NCA-90), CLAUDIN-3, CLAUDIN-4, cMet, Collagen, Cripto, CSFR, CSFR-1, CTLA-4, CTGF, CXCL10, CXCL13, CXCR1, CXCR2, CXCR4, CYR61, DL44, DLK1, DLL3, DLL4, DPP-4, DSG1, EDA, EDB, EGFR, EGFRviii, Endothelin B receptor (ETBR), ENPP3, EpCAM, EPHA2, EPHB2, ERBB3, F protein of RSV, FAP, FGF-2, FGF8, FGFR1, FGFR2, FGFR3, FGFR4, Fibronectin extra-domain B (EDB), FLT-3, Folate receptor alpha (FRα), GAL3ST1, G-CSF, G-CSFR, GD2, GITR, GLUT1, GLUT4, GM-CSF, GM-CSFR, GP IIb/IIIa receptors. Gp130, GPIIB/IIIA, GPNMB, GRP78, HER2/neu, HER3, HER4, HGF, hGH, HVEM, Hyaluronidase. IFNalpha, IFNbeta, IFNgamma, IgE, IgE Receptor (FceRI), IGF, IGF1R, IL1B, IL1R, IL2, IL11, IL12, IL 12p40, IL-12R, IL-12Rbeta1, IL13, IL13R, IL15, IL17, IL18, IL21, IL23, IL23R, IL27/IL27R (wsx1), IL29, IL-31R, IL31/IL31R, IL2R, IL4, IL4R, IL6, IL6R, Insulin Receptor, Jagged Ligands, Jagged 1, Jagged 2, KISS1-R, LAG-3, LIF-R, Lewis X, LIGHT, LRP4, LRRC26, Ly6G6D, LyPD1, MCSP, Mesothelin, MRP4, MUC1, Mucin-16 (MUC16, CA-125), Na/K ATPase, NGF, NEctin 4, Nicastrin, Notch Receptors, Notch 1, Notch 2, Notch 3, Notch 4, NOV, OSM-R, OX-40, PAR2, PDGF-AA, PDGF-BB, PDGFRalpha, PDGFRbeta, PD-1, PD-L1, PD-L2, Phosphatidyl-serine, P1GF, PSCA, PSMA, PSGR, RAAG12, RAGE, SLC44A4, Sphingosine 1 Phosphate, STEAP1, STEAP2, TAG-72, TAPA1, TEM-8, TGFbeta, TIGIT, TIM-3, TLR2, TLR4, TLR6, TLR7, TLR8, TLR9, TMEM31, TNFalpha, TNFR, TNFRS12A, TRAIL-R1, TRAIL-R2, Transferrin, Transferrin receptor, TRK-A, TRK-B, uPAR, VAP1, VCAM-1, VEGF, VEGF-A, VEGF-B, VEGF-C, VEGF-D, VEGFR1, VEGFR2, VEGFR3, VISTA, WISP-1, WISP-2, and WISP-3. In some embodiments, one or more antigen-binding domains of the extracellular binding moiety is an scFv or a VHH. In some embodiments, the extracellular binding moiety binds or is capable of binding a target antigen with sufficient affinity such that the CAR is useful in therapy, for example, it is useful for targeting a cell or tissue expressing the target antigen.

The transmembrane domain of a CAR is a domain that typically crosses or is capable of crossing or spanning the plasma membrane and is connected, directly or indirectly (e.g. via a spacer, such as an immunoglobulin hinge sequence) to the extracellular antigen-binding domain and the endoplasmic portion containing the intracellular signaling domain. In some embodiments, the transmembrane domain of the CAR is a transmembrane region of a transmembrane protein (for example Type I transmembrane proteins), an artificial hydrophobic sequence or a combination thereof. In some embodiments, the transmembrane domain comprises the CD3zeta domain or CD28 transmembrane domain. Other transmembrane domains will be apparent to those of skill in the art and may be used in connection with embodiments of a CAR provided herein.

The intracellular signaling region of a CAR provided herein contains one or more intracellular signaling domain that transmits a signal to a T cell upon engagement of the antigen binding domain of the CAR, such as upon binding antigen. In some embodiments, the intracellular region contains an intracellular signaling domain that is or contains an ITAM signaling domain. Exemplary intracellular signaling domains include, for example, a signaling domain derived from ζ chain of the T-cell receptor complex or any of its homologs (e.g., η chain, FcsRIy and β chains, MB 1 (Iga) chain, B29 (Ig) chain, etc.), human CD3zeta chain, CD3 polypeptides (Δ, δ and ε), syk family tyrosine kinases (Syk. ZAP 70, etc.), src family tyrosine kinases (Lck, Fyn, Lyn, etc.) and other molecules involved in T-cell transduction, such as CD2, CD5, OX40 and CD28. In particular embodiments, the intracellular signaling region contains an intracellular signaling domain derived from the human CD3 zeta chain.

In some embodiments, the endodomain comprises at CD3-zeta signaling domain. In some embodiments, the CD3-zeta signaling domain comprises the sequence of amino acids set forth in SEQ ID NO: 27 or a sequence of amino acids that exhibits at least 85%, 86%, 87%, 88%, 89%, 90%, 91%, 92%, 93%, 94%, 95%, 96%, 97%, 98% or 99% or more sequence identity to SEQ ID NO: 27 and retains the activity of T cell signaling.

In some embodiments, the intracellular signaling region of a CAR can further contain an intracellular signaling domain derived from a costimulatory molecule. In such examples, such a signaling domain may enhance CAR-T cell activity, such as via enhancement of proliferation, survival and/or development of memory cells, after antigen specific engagement, for example, compared to a CAR that only contains an ITAM containing signaling domain, e.g. CD3 zeta. In some embodiments, the co-stimulatory domain is a functional signaling domain obtained from a protein selected from: CD28, CD137 (4-IBB), CD134 (OX40), DapIO, CD27, CD2, CD5, ICAM-1, LFA-1 (CD11a/CD18), Lck, TNFR-I, TNFR-II, Fas, CD30, CD40 or combinations thereof. In particular embodiments, the costimulatory signaling domain is derived or obtained from a human protein. In some aspects, the costimulatory signaling domain is derived or obtained from human CD28 or human CD137 (4-IBB).

In some embodiments, the costimulatory signaling domain is a derived from CD28 or 4-1BB and comprises the sequence of amino acids set forth in any of SEQ ID NOS: 28-31 or a sequence of amino acids that exhibits at least 85%, 86%, 87%, 88%, 89%, 90%, 91%, 92%, 93%, 94%, 95%, 96%, 97%, 98% or 99% or more sequence identity to SEQ ID NO: 28-31 and retains the activity of T cell costimulatory signaling.

In some embodiments, the CAR further comprises a hinge or spacer region that connects the extracellular antigen binding domain and the transmembrane domain. This hinge or spacer region can be used to achieve different lengths and flexibility of the resulting CAR. Examples of the hinge or spacer region that can be used include, but are not limited to, Fc fragments of antibodies or fragments or derivatives thereof, hinge regions of antibodies, or fragments or derivatives thereof, $C_H2$ regions of antibodies, $C_H3$ regions of antibodies, artificial spacer sequences, for example peptide sequences, or combinations thereof. Other hinge or spacer region will be apparent to those of skill in the art and may be used. In one embodiment, the hinge is an IgG4 hinge or a CD8A hinge.

In some embodiments, the spacer and transmembrane domain are the hinge and transmembrane domain derived from CD8, such as having an exemplary sequence set forth in SEQ ID NO: 32-34 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 32-34.

Also provided herein are isolated nucleic acids comprising a polynucleotide encoding a CAR comprising an OX40-binding polypeptide provided herein. In some embodiments, a first nucleic acid encoding the CAR is separated from a second nucleic acid encoding the OX40-binding polypeptide by a biscistronic element, such as an IRES or a ribosome skip sequence (e.g. T2A or P2A). In some aspects, the construct is an expression vector for expression of the OX40-binding polypeptide and/or CAR in a cell. The expression vector may be a viral vector. Viral vector technology is well known in the art and is described, for example, in Sambrook et al. (Molecular Cloning: A Laboratory Manual. Cold Spring Harbor Laboratory, New York, 2013). A number of viral based systems have been developed for gene transfer into mammalian cells. For example, retroviruses such as, adenovirus vectors are used. In one embodiment, a lentivirus vector is used.

In a further aspect, also provided is an isolated cell or cell population comprising one or more nucleic acid construct as described above. Also provided is an isolated cell or cell population that has been genetically modified to express an OX40-binding polypeptide and/or CAR provided herein. Thus, provided herein are genetically engineered cells which comprise, any may stably express, a CAR provided herein. In one embodiment, the cell is selected from a T cell, a Natural Killer (NK) cell, a cytotoxic T lymphocyte (CTL), a regulatory T cell, hematopoietic stem cell, and/or pluripotent embryonic/induced stem cell. In some cases, the cell is a T cell, such as a CD4+ and/or CD8+ T cell. In some embodiments, the cells are autologous to the subject. For example, in some embodiments, T cells may be isolated from a patient (also called primary T cells) for engineering, e.g. transfecting or transducing, with a CAR nucleic acid construct.

In an exemplary method, primary T cells can be purified ex vivo (CD4+ cells or CD8+ cells or both) and stimulated with a TCR/CD28 agonists, such as anti-CD3/anti-CD28 coated beads. After a 2 or 3 day activation process, a recombinant expression vector encoding the CAR can be stably introduced into the primary T cells through standard lentiviral or retroviral transduction protocols or plasmid electroporation strategies. Cells can be monitored for secretion of an OX40-binding polypeptide and/or CAR expression by, for example, flow cytometry using anti-epitope tag or antibodies that cross-react with native parental molecule. T cells that express the CAR can be enriched through sorting with anti-epitope tag antibodies or enriched for high or low expression depending on the application.

The OX40-binding polypeptides and/or CAR engineered T cells can be assayed for appropriate function by a variety of means. In some cases, in vitro cytotoxicity, proliferation, OX40 reporter assays, or cytokine assays (e.g., IFN-gamma, IL-2, TNFα expression) can be used to assess the function of engineered T-cells. Exemplary standard endpoints are percent lysis of a tumor line, proliferation of the engineered T-cell, or IFN-gamma protein expression in culture supernatant. In some cases, the ability to stimulate activation of T cells upon stimulation of the CAR, e.g. via antigen, can be assessed, such as by monitoring expression of activation markers such as CD69, CD44, or CD62L, proliferation and/or cytokine production.

Also provided herein are methods for the prevention and/or treatment of a disease or condition in a subject, such as a cancer, that includes administering to a subject engineered cells provided herein. Generally, the subject is in need of treatment for the disease or condition, pharmaceutically active amount of a cell and/or of a pharmaceutical composition of the invention. In some embodiments, cells that express and secrete an OX40 binding polypeptide provided herein are used in treatment. In some embodiments, CAR engineered T cells that express an OX40 binding polypeptide provided herein are used for treatment.

Polypeptide Expression and Production

Nucleic acid molecules comprising polynucleotides that encode an OX40-binding polypeptide are provided. Thus, in various embodiments, nucleic acid molecules are provided that encode a VHH domain that binds OX40 comprises a CDR1 comprising the amino acid sequence of SEQ ID NO: 10, a CDR2 comprising the amino acid sequence of SEQ ID NO: 11, and a CDR3 comprising the amino acid sequence of SEQ ID NO: 12. In some embodiments, nucleic acid molecules are provided that encode a VHH domain that binds OX40 comprises a CDR1 comprising the amino acid sequence of SEQ ID NO: 10, a CDR2 comprising the amino acid sequence of SEQ ID NO: 11, and a CDR3 comprising the amino acid sequence of SEQ ID NO: 12; and a framework 2 (FR2) comprising the amino acid sequence of SEQ ID NO: 22. In some embodiments, the nucleic acid molecule further encodes a FR3 comprising the amino acid sequence of SEQ ID NO: 23. In some embodiments, nucleic acid molecules are provided that encode an OX40-binding polypeptide that comprises at least one, such as one, two, three, or four VHH domain comprising the amino acid sequence of SEQ ID NO: 9. In various embodiments, the nucleic acid molecule further encodes an Fc domain, such as an Fc domain of SEQ ID NO: 25 or 26. In some embodiments, a nucleic acid molecule is provided that encodes an OX40-binding polypeptide that comprises three VHH domains and an Fc domain comprise the amino acid sequence of SEQ ID NO: 14 and an Fc domain fused to the C-terminus of that amino acid sequence. In some embodiments, a nucleic acid molecule is provided that encodes an OX40-binding polypeptide comprising or consisting of the amino acid sequence of SEQ ID NO: 15. In any of the foregoing embodiments, the nucleic acid molecule may also encode a leader sequence that directs secretion of the OX40-binding polypeptide, which leader sequence is typically cleaved such that it is not present in the secreted polypeptide. The leader sequence may be a native heavy chain (or VHH) leader sequence, or may be another heterologous leader sequence.

Nucleic acid molecules can be constructed using recombinant DNA techniques conventional in the art. In some embodiments, a nucleic acid molecule is an expression vector that is suitable for expression in a selected host cell.

Vectors comprising nucleic acids that encode the OX40-binding polypeptides described herein are provided. Such vectors include, but are not limited to, DNA vectors, phage vectors, viral vectors, retroviral vectors, etc. In some embodiments, a vector is selected that is optimized for expression of polypeptides in a desired cell type, such as CHO or CHO-derived cells, or in NSO cells. Exemplary such vectors are described, for example, in Running Deer et al., *Biotechnol. Prog.* 20:880-889 (2004).

In some embodiments, an OX40-binding polypeptide=may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S, DG44, Lec13 CHO cells, and FUT8 CHO cells; PER.C6® cells (Crucell); and NSO cells. In some embodiments, the OX40-binding polypeptides may be expressed in yeast. See, e.g., U.S. Publication No. US 2006/0270045 A1. In some embodiments, a particular eukaryotic host cell is selected based on its ability to make desired post-translational modifications to the polypeptide. For example, in some embodiments, CHO cells produce polypeptides that have a higher level of sialylation than the same polypeptide produced in 293 cells.

Introduction of one or more nucleic acids (such as vectors) into a desired host cell may be accomplished by any method, including but not limited to, calcium phosphate transfection. DEAE-dextran mediated transfection, cationic lipid-mediated transfection, electroporation, transduction, infection, etc. Nonlimiting exemplary methods are described, for example, in Sambrook et al., Molecular Cloning, A Laboratory Manual, 3$^{rd}$ ed. Cold Spring Harbor Laboratory Press (2001). Nucleic acids may be transiently or stably transfected in the desired host cells, according to any suitable method.

Host cells comprising any of the nucleic acids or vectors described herein are also provided. In some embodiments, a host cell that expresses an OX40-binding polypeptide described herein is provided. The OX40-binding polypeptides expressed in host cells can be purified by any suitable method. Such methods include, but are not limited to, the use of affinity matrices or hydrophobic interaction chromatography. Suitable affinity ligands include the ROR1 ECD and agents that bind Fc regions. For example, a Protein A, Protein G, Protein A/G, or an antibody affinity column may be used to bind the Fc region and to purify an OX40-binding polypeptide that comprises an Fc region. Hydrophobic interactive chromatography, for example, a butyl or phenyl column, may also suitable for purifying some polypeptides such as antibodies. Ion exchange chromatography (for example anion exchange chromatography and/or cation exchange chromatography) may also suitable for purifying some polypeptides such as antibodies. Mixed-mode chromatography (for example reversed phase/anion exchange, reversed phase/cation exchange, hydrophilic interaction/anion exchange, hydrophilic interaction/cation exchange, etc.) may also suitable for purifying some polypeptides such as antibodies. Many methods of purifying polypeptides are known in the art.

In some embodiments, the OX40-binding polypeptide is produced in a cell-free system. Nonlimiting exemplary cell-free systems are described, for example, in Sitaraman et al., *Methods Mol. Biol.* 498:229-44 (2009); Spirin. *Trends Biotechnol.* 22:538-45 (2004); Endo et al., *Biotechnol. Adv.* 21:695-713 (2003).

In some embodiments, OX40-binding polypeptides prepared by the methods described above are provided. In some embodiments, the OX40-binding polypeptide is prepared in a host cell. In some embodiments, the OX40-binding polypeptide is prepared in a cell-free system. In some embodiments, the OX40-binding polypeptide is purified. In some embodiments, a cell culture media comprising an OX40-binding polypeptide is provided.

In some embodiments, compositions comprising antibodies prepared by the methods described above are provided. In some embodiments, the composition comprises an OX40-binding polypeptide prepared in a host cell. In some embodiments, the composition comprises an OX40-binding polypeptide prepared in a cell-free system. In some embodiments, the composition comprises a purified OX40-binding polypeptide.

Exemplary Methods of Treating Diseases Using OX40-Binding Polypeptides

In some embodiments, methods of treating disease in an individual comprising administering an OX40-binding polypeptide are provided. Such diseases include any disease that would benefit from increase proliferation and activation of $CD4^+$ and/or $CD8^+$ T cells. In some embodiments, methods for treating cancer in an individual are provided. The method comprises administering to the individual an effective amount of an OX40-binding polypeptide provided herein. Such methods of treatment may be in humans or animals. In some embodiments, methods of treating humans are provided. Nonlimiting exemplary cancers that may be treated with OX40-binding polypeptides provided herein include basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer; gastrointestinal cancer; glioblastoma; hepatic carcinoma; hepatoma; intra-epithelial neoplasm; kidney or renal cancer; larynx cancer; liver cancer; lung cancer; small-cell lung cancer; non-small cell lung cancer; adenocarcinoma of the lung; squamous carcinoma of the lung; melanoma; myeloma; neuroblastoma; oral cavity cancer; ovarian cancer; pancreatic cancer; prostate cancer; retinoblastoma; rhabdomyosarcoma; rectal cancer; cancer of the respiratory system; salivary gland carcinoma; sarcoma; skin cancer;

squamous cell cancer; stomach cancer; testicular cancer; thyroid cancer; uterine or endometrial cancer; cancer of the urinary system; and vulval cancer; lymphoma; Hodgkin's lymphoma; non-Hodgkin's lymphoma; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; chronic lymphocytic leukemia (CLL); acute lymphoblastic leukemia (ALL); Hairy cell leukemia; and chronic myeloblastic leukemia.

The OX40-binding polypeptides can be administered as needed to subjects. Determination of the frequency of administration can be made by persons skilled in the art, such as an attending physician based on considerations of the condition being treated, age of the subject being treated, severity of the condition being treated, general state of health of the subject being treated and the like. In some embodiments, an effective dose of an OX40-binding polypeptides is administered to a subject one or more times. In some embodiments, an effective dose of an OX40-binding polypeptides is administered to the subject daily, semi-weekly, weekly, every two weeks, once a month, etc. An effective dose of an OX40-binding polypeptides is administered to the subject at least once. In some embodiments, the effective dose of an OX40-binding polypeptides may be administered multiple times, including multiple times over the course of at least a month, at least six months, or at least a year.

In some embodiments, pharmaceutical compositions are administered in an amount effective for treating (including prophylaxis of) cancer and/or increasing T-cell proliferation. The therapeutically effective amount is typically dependent on the weight of the subject being treated, his or her physical or health condition, the extensiveness of the condition to be treated, or the age of the subject being treated. In general, antibodies may be administered in an amount in the range of about 0.05 mg/kg body weight to about 100 mg/kg body weight per dose. In some embodiments, antibodies may be administered in an amount in the range of about 10 µg/kg body weight to about 100 mg/kg body weight per dose. In some embodiments, antibodies may be administered in an amount in the range of about 50 µg/kg body weight to about 5 mg/kg body weight per dose. In some embodiments, antibodies may be administered in an amount in the range of about 100 µg/kg body weight to about 10 mg/kg body weight per dose. In some embodiments, antibodies may be administered in an amount in the range of about 100 µg/kg body weight to about 20 mg/kg body weight per dose. In some embodiments, antibodies may be administered in an amount in the range of about 0.5 mg/kg body weight to about 20 mg/kg body weight per dose. In some embodiments, antibodies may be administered in an amount in the range of about 0.5 mg/kg body weight to about 10 mg/kg body weight per dose. In some embodiments, antibodies may be administered in an amount in the range of about 0.05 mg/kg body weight to about 20 mg/kg body weight per dose. In some embodiments, antibodies may be administered in an amount in the range of about 0.05 mg/kg body weight to about 10 mg/kg body weight per dose. In some embodiments, antibodies may be administered in an amount in the range of about 5 mg/kg body weight or lower, for example less than 4, less than 3, less than 2, or less than 1 mg/kg of the antibody.

In some embodiments, OX40-binding polypeptides can be administered in vivo by various routes, including, but not limited to, intravenous, intra-arterial, parenteral, intraperitoneal or subcutaneous. The appropriate formulation and route of administration may be selected according to the intended application.

In some embodiments, a therapeutic treatment using an OX40-binding polypeptide is achieved by increasing T-cell proliferation and/or activation. In some embodiments, increasing T-cell proliferation and/or activation inhibits growth of cancer.

Pharmaceutical Compositions

In some embodiments, compositions comprising OX40-binding polypeptides are provided in formulations with a wide variety of pharmaceutically acceptable carriers (see, for example, Gennaro, Remington: The Science and Practice of Pharmacy with Facts and Comparisons: Drugfacts Plus, 20th ed. (2003); Ansel et al., Pharmaceutical Dosage Forms and Drug Delivery Systems, $7^{th}$ ed., Lippencott Williams and Wilkins (2004); Kibbe et al., Handbook of Pharmaceutical Excipients, $3^{rd}$ ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available. Non-limiting exemplary carriers include saline, buffered saline, dextrose, water, glycerol, ethanol, and combinations thereof.

In some embodiments, a pharmaceutical composition comprises an OX40-binding polypeptide at a concentration of at least 10 mg/mL, 20 mg/mL, 30 mg/mL, 40 mg/mL, 50 mg/mL, 60 mg/mL, 70 mg/mL, 80 mg/mL, 90 mg/mL, 100 mg/mL, 125 mg/mL, 150 mg/mL, 175 mg/mL, 200 mg/mL, 225 mg/mL, or 250 mg/mL.

Combination Therapy

OX40-binding polypeptides can be administered alone or in combination with other modes of treatment, such as other anti-cancer agents. They can be provided before, substantially contemporaneous with, or after other modes of treatment (i.e., concurrently or sequentially). In some embodiments, the method of treatment described herein can further include administering: radiation therapy, chemotherapy, vaccination, targeted tumor therapy, CAR-T therapy, oncolytic virus therapy, cancer immunotherapy, cytokine therapy, surgical resection, chromatin modification, ablation, cryotherapy, an antisense agent against a tumor target, a siRNA agent against a tumor target, a microRNA agent against a tumor target or an anti-cancer/tumor agent, or a biologic, such as an antibody, cytokine, or receptor extracellular domain-Fc fusion.

In some embodiments, an OX40-binding polypeptide provided herein is given concurrently with a second therapeutic agent, for example, a PD-1 therapy. Examples of PD-1/PD-L1 therapy include nivolumab (BMS); pidilizumab (CureTech, CT-011), pembrolizumab (Merck); durvalumab (Medimmune/AstraZeneca); atezolizumab (Genentech/Roche); avelumab (Pfizer); AMP-224 (Amplimmune); BMS-936559; AMP-514 (Amplimmune); MDX-1105 (Merck); TSR-042 (Tesaro/AnaptysBio, ANB-011); STI-A1010 (Sorrento Therapeutics); STI-A1110 (Sorrento Therapeutics); and other agents that are directed against programmed death-1 (PD-1) or programmed death ligand 1 (PD-L1).

In some embodiments, an OX40-binding polypeptide provided herein is given concurrently with CAR-T (chimeric antigen receptor T-cell) therapy, oncolytic virus therapy, cytokine therapy, and/or agents that target other checkpoint molecules, such as VISTA, gpNMB, B7H3, B7H4, HHLA2, CD73, CTLA4, TIGIT, etc.

Nonlimiting Exemplary Methods of Diagnosis and Treatment

In some embodiments, the methods described herein are useful for evaluating a subject and/or a specimen from a subject (e.g. a cancer patient). In some embodiments, evaluation is one or more of diagnosis, prognosis, and/or response to treatment.

In some embodiments, the methods described herein comprise evaluating a presence, absence, or level of a protein. In some embodiments, the methods described herein comprise evaluating a presence, absence, or level of expression of a nucleic acid. The compositions described herein may be used for these measurements. For example, in some embodiments, the methods described herein comprise contacting a specimen of the tumor or cells cultured from the tumor with a therapeutic agent as described herein.

In some embodiments, the evaluation may direct treatment (including treatment with the antibodies described herein). In some embodiments, the evaluation may direct the use or withholding of adjuvant therapy after resection. Adjuvant therapy, also called adjuvant care, is treatment that is given in addition to the primary, main or initial treatment. By way of non-limiting example, adjuvant therapy may be an additional treatment usually given after surgery where all detectable disease has been removed, but where there remains a statistical risk of relapse due to occult disease. In some embodiments, the antibodies are used as an adjuvant therapy in the treatment of a cancer. In some embodiments, the antibodies are used as the sole adjuvant therapy in the treatment of a cancer. In some embodiments, the antibodies described herein are withheld as an adjuvant therapy in the treatment of a cancer. For example, if a patient is unlikely to respond to an antibody described herein or will have a minimal response, treatment may not be administered in the interest of quality of life and to avoid unnecessary toxicity from ineffective chemotherapies. In such cases, palliative care may be used.

In some embodiments the molecules are administered as a neoadjuvant therapy prior to resection. In some embodiments, neoadjuvant therapy refers to therapy to shrink and/or downgrade the tumor prior to any surgery. In some embodiments, neoadjuvant therapy means chemotherapy administered to cancer patients prior to surgery. In some embodiments, neoadjuvant therapy means an antibody is administered to cancer patients prior to surgery. Types of cancers for which neoadjuvant chemotherapy is commonly considered include, for example, breast, colorectal, ovarian, cervical, bladder, and lung. In some embodiments, the antibodies are used as a neoadjuvant therapy in the treatment of a cancer. In some embodiments, the use is prior to resection.

In some embodiments, the tumor microenvironment contemplated in the methods described herein is one or more of: tumor vasculature; tumor-infiltrating lymphocytes; fibroblast reticular cells; endothelial progenitor cells (EPC); cancer-associated fibroblasts; pericytes; other stromal cells; components of the extracellular matrix (ECM); dendritic cells; antigen presenting cells; T-cells; regulatory T-cells; macrophages; neutrophils; and other immune cells located proximal to a tumor.

Kits

Also provided are articles of manufacture and kits that include any of OX40-binding polypeptides as described herein, and suitable packaging. In some embodiments, the invention includes a kit with (i) an OX40-binding polypeptide, and (ii) instructions for using the kit to administer the OX40-binding polypeptide to an individual.

Suitable packaging for compositions described herein are known in the art, and include, for example, vials (e.g., sealed vials), vessels, ampules, bottles, jars, flexible packaging (e.g., sealed Mylar or plastic bags), and the like. These articles of manufacture may further be sterilized and/or sealed. Also provided are unit dosage forms comprising the compositions described herein. These unit dosage forms can be stored in a suitable packaging in single or multiple unit dosages and may also be further sterilized and sealed. Instructions supplied in the kits of the invention are typically written instructions on a label or package insert (e.g., a paper sheet included in the kit), but machine-readable instructions (e.g., instructions carried on a magnetic or optical storage disk) are also acceptable. The instructions relating to the use of the antibodies generally include information as to dosage, dosing schedule, and route of administration for the intended treatment or industrial use. The kit may further comprise a description of selecting an individual suitable or treatment.

The containers may be unit doses, bulk packages (e.g., multi-dose packages) or sub-unit doses. For example, kits may also be provided that contain sufficient dosages of molecules disclosed herein to provide effective treatment for an individual for an extended period, such as about any of a week, 2 weeks, 3 weeks, 4 weeks, 6 weeks, 8 weeks, 3 months, 4 months, 5 months, 6 months, 7 months, 8 months, 9) months, or more. Kits may also include multiple unit doses of molecules and instructions for use and packaged in quantities sufficient for storage and use in pharmacies, for example, hospital pharmacies and compounding pharmacies. In some embodiments, the kit includes a dry (e.g., lyophilized) composition that can be reconstituted, resuspended, or rehydrated to form generally a stable aqueous suspension of antibody.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: 1D10v6-Fc has Reduced Non-Specific Binding Compared to 1D10v1-Fc

Single domain antibodies (sdAbs) comprising VHH domains that bind OX40 were previously developed. See PCT Publication No. WO 2017/123673 A2. SdAb 1D10 was selected for humanization, resulting in 1D10v1. See id, and SEQ ID NO: 3.

1D10v1 was optimized to reduce nonspecific binding. That optimization resulted in a substitution of one amino acid in CDR3 of the VHH domain of the sdAb and two amino acids in framework region 2 (FR2), giving 1D10v6 (SEQ ID NO: 9). CDR3 of 1D10v6 (SEQ ID NO: 12) has a G to A substitution relative to CDR3 of 1D10v1 (SEQ ID NO: 6), and FR2 of 1D10v6 has a GL to ER substitution (SEQ ID NO: 22). Surprisingly, those substitutions reduced nonspecific binding of the sdAb, while affinity for human and cynomolgus monkey OX40 was retained, as described below.

Nonspecific binding of bivalent sdAbs was determined by flow cytometry following high temperature stress. Purified 1D10v1-Fc and 1D10v6-Fc were buffer exchanged into 20 mM Tris pH 8.0, 150 mM NaCl, 2% trehalose, 0.2% TWEEN-20, and stressed by incubating at 50° C. for 7 days. The antibodies were then filtered using a 0.2 μm Acrodisc syringe filter, and quantitated by A280 measurement. HEK293 cells do not express measurable OX40 on the cell surface, and thus were used as a control cell line for non-specific binding. 30,000 cells per well were incubated with a dilution series of temperature-stressed 1D10v1-Fc or 1D10v6-Fc. Following incubation with the primary antibodies, a secondary anti-human Fc Alexa Fluor 647 was used at 1/2000 dilution, then bound antibody was measured by flow cytometry in an Intellicyte iQue Plus, and fluorescence was plotted as median fluorescence intensity. As shown in FIG. 1, 1D10v1-Fc exhibited nonspecific binding to the untransfected HEK293 cells starting at about 33 nM sdAb, which binding dramatically increased as the sdAb concentration increased. In contrast, 1D10v6-Fc exhibited no detectable binding to the untransfected HEK293 cells up to 1000 nM sdAb.

Figure 2A:
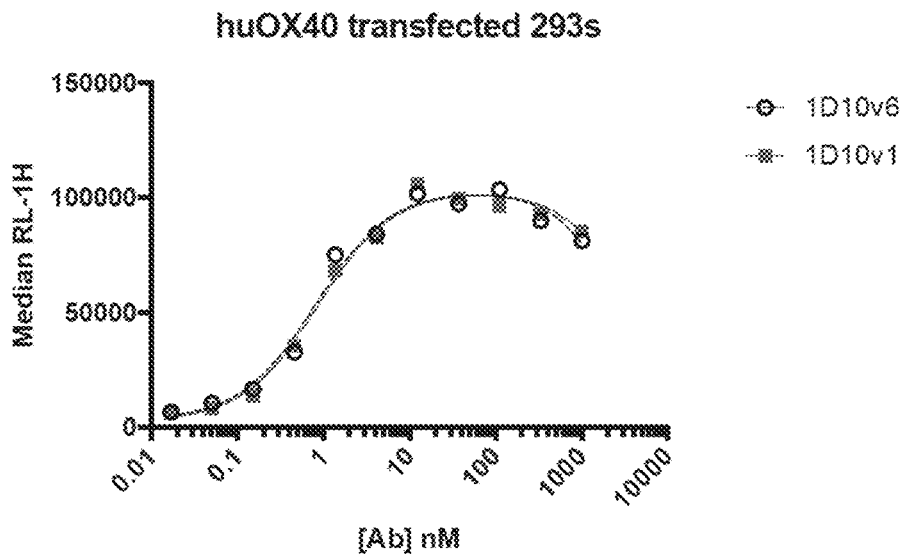
FIG. 2A-2B show binding of 1D10v1-Fc and 1D10v6-Fc to CHO cells that express human OX40 (A) and cynomolgus monkey OX40 (B).
Figure 2B:
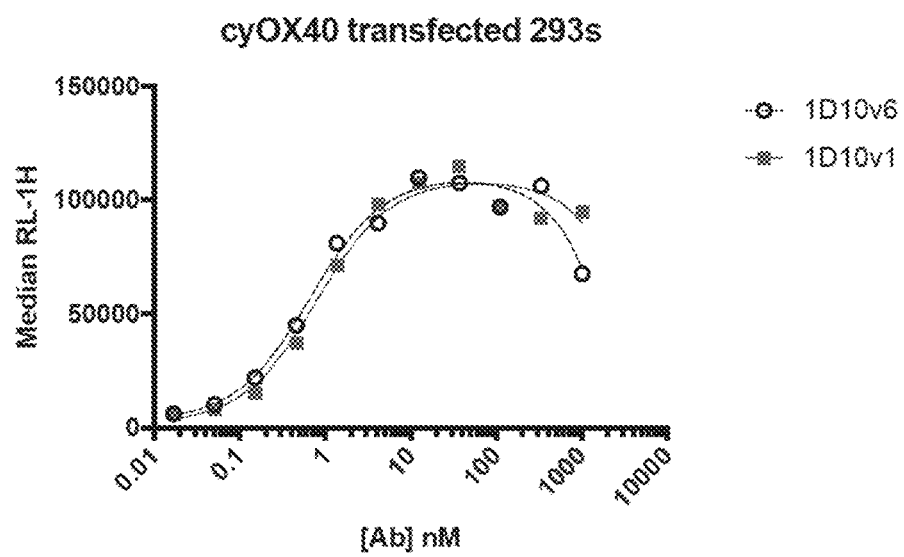

Binding of the sdAbs to human and cynomolgus monkey OX40 was determined as follows. Stably transfected CHO cells that express full length human OX40 or cynomolgus monkey OX40 were plated at 50,000 cells/well. Antibodies were titrated serially diluted 1:3 starting at 400 nM, and detected with anti-human Fc 488 secondary antibody. Flow cytometric analysis was performed on an Intellicyte iQue analyzer and fluorescence was plotted as mean fluorescence intensity. As shown in FIG. 2, 1D10v6-Fc showed comparable binding to human OX40 (FIG. 2A) and cynomolgus monkey OX40 (FIG. 2B) as 1D10v1-Fc. The affinity ($K_D$) of 1D10v6-Fc for human and cynomolgus monkey OX40 was 0.81 nM and 0.66 nM, respectively. The affinity ($K_D$) of 1D10v1-Fc for human and cynomolgus monkey OX40 was 0.86 nM and 0.79 nM, respectively.

Example 2: Hexavalent 3x1D10v6-Fc has Reduced Non-Specific Binding Compared to Hexavalent 3x1D10v1-Fc Hexavalent anti-OX40 sdAbs were made by joining three VHH domains to an Fc, which polypeptide forms a hexavalent dimer. Nonspecific binding of hexavalent 3x1D10v1-Fc (SEQ ID NO: 8: also referred to as Hex-1D10v1) and hexavalent 3x1D10v6-Fc (SEQ ID NO: 14: also referred to as Hex-1D10v6) was determined as follows. 3x1D10v1-Fc and 3x1D10v6-Fc were incubated for 48 hours at room temperature in a buffer of 20 mM His, 150 mM NaCl, 0.02% TWEEN-20, pH 9, with untransfected HEK293 freestyle cells or with transiently transfected HEK293 freestyle cells expressing the full length OX40. A fluorescent anti-Fc specific secondary antibody was used to detect bound 3x1D10v1-Fc and 3x1D10v6-Fc, and measured by flow cytometry using an Intellicyte iQue analyzer. Mean fluorescence intensity was plotted for each concentration of antibody.

Figure 3A:
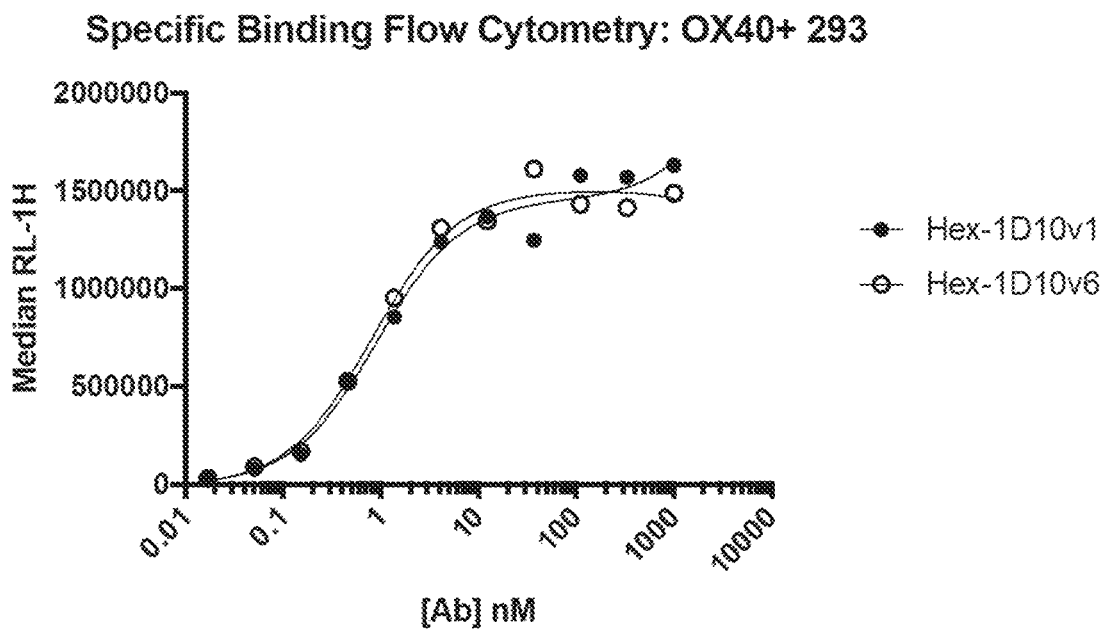
FIG. 3A-3B show binding of hexavalent 3x1D10v1-Fc and hexavalent 3x1D10v6-Fc (also referred to as Hex-1D10v1 and Hex-1D10v6, respectively) to HEK293 cells that express human OX40 (A) and to untransfected HEK293 cells (B).
Figure 3B:
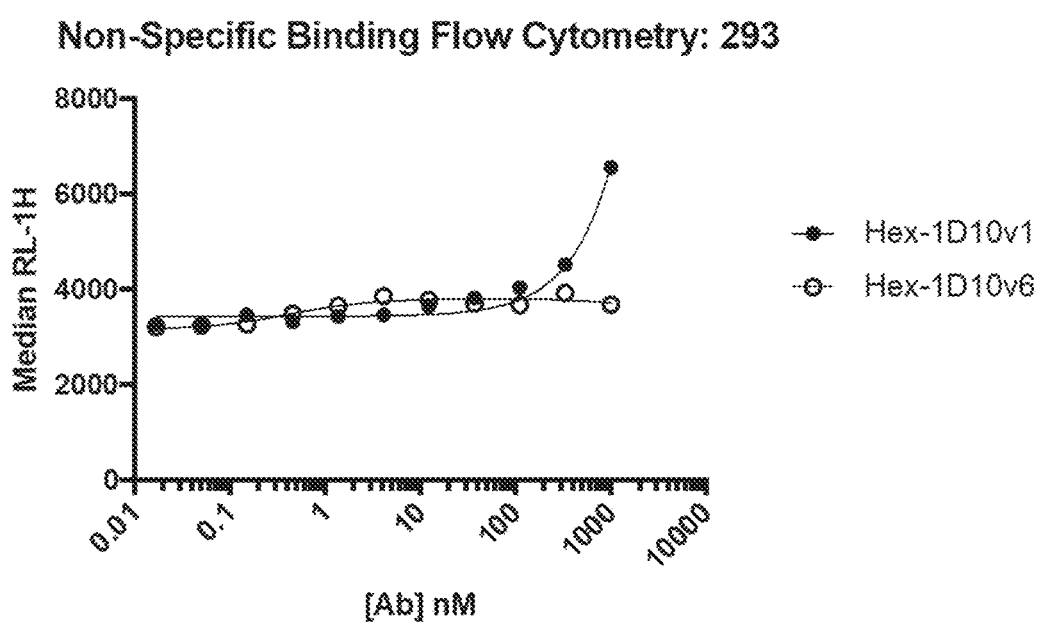

As shown in FIG. 3. 3x1D10v1-Fc and 3x1D10v6-Fc showed comparable specific binding under these conditions, with apparent $K_D$ of 0.82 nM and 0.90 nM, respectively (FIG. 3A). 3x1D10v1-Fc exhibited non-specific binding to untransfected HEK293 cells, however, while 3x1D10v6-Fc did not (FIG. 3B).

Example 3: Hexavalent 3x1D10v6-Fc Retains OX40 Agonist Activity

As described above, 3x1D10v6-Fc had reduced nonspecific binding to HEK293 cells, while retaining OX40 binding affinity. Agonist activity of 3x1D10v6-Fc was confirmed as follows.

Thaw-and-Use Jurkat/OX40 reporter cells (Promega) passage 5 were removed from liquid nitrogen and thawed in 37° C. water bath. The cells stably express OX40 and contain a luciferase reporter downstream of an NFκB response element. Cells were gently mixed and transferred to 9 mL of pre-warmed culture media (RPMI+10% FBS). Cells were centrifuged at 400×g for 5 minutes, and resuspended in 5 mL of assay media (RPMI+10% FBS). Cell density and viability were determined using Trypan Blue and a TC20 Automated Cell Counter. In inner 60-wells of assay plates, cells plated at $6\times10^4$ cells/well in 50 μL/well assay media. 100 μL/well of assay media was added to outer wells. 2.5 mLs of assay media was added to each corner reservoir of assay plate.

3x1D10v1-Fc and 3x1D10v6-Fc were diluted in assay media so that the concentration was 2× desired highest final concentration. A 9-point serial dilution was made (5-fold, 5-fold, 2-fold, 2-fold, 2-fold, 2-fold, 5-fold, 5-fold), with highest concentration being 50 nM and lowest being 0.005 nM. Thus final assay concentration would be highest 25 nM and lowest 0.0025 nM. Antibody dilutions were performed in a 96-well dilution plate. 50 μL/well of 2× antibody dilutions were added to assay plates. Final assay volume per well was 100 μL. Assay plates were covered with plate lids and placed in CO2 incubator at 37° C. for 6 hours.

After 6-hour incubation, assay plates were removed from incubator and placed at room temperature for 10 minutes. 100 μL of reconstituted Bio-Glo Luciferase reagent (Promega) was added to each well containing cells in assay plates. Assay plates were incubated for 10 minutes at room temperature. 100 μL/well of assay plate transferred to white 96-well plate to measure relative luminescence units (RLU). Plates were read on Molecular Devices SpectraMax L plate reader and SoftMax Pro v5.4 according to settings defined in table of reagents (PMT-MaxRange. Target Wave-470 nm).

Figure 4:
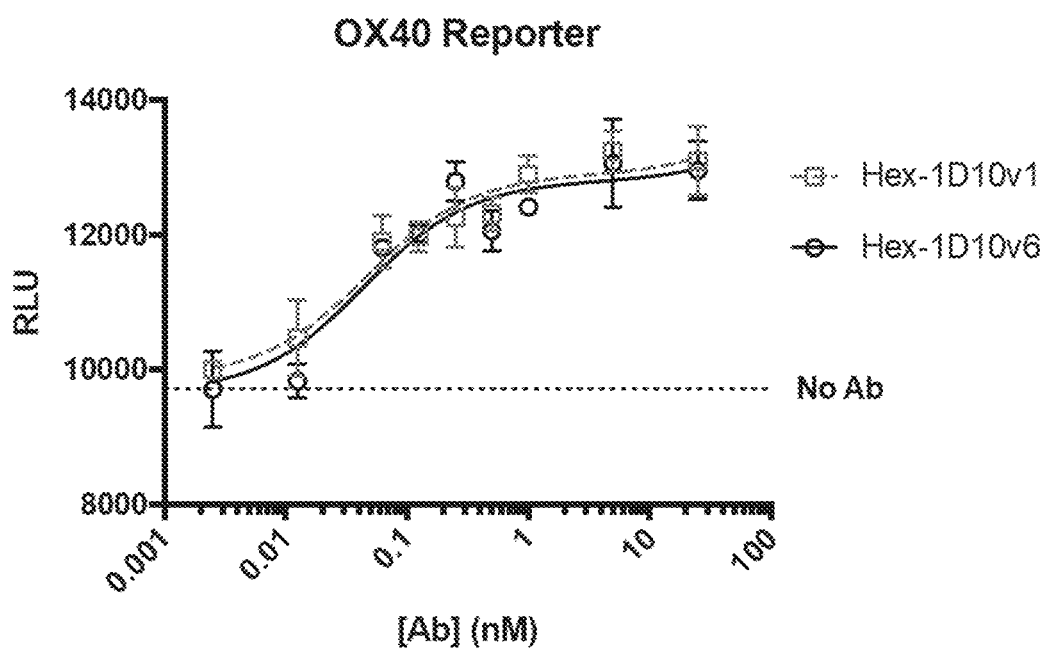
FIG. 4 shows activation of luciferase expression by hexavalent 3x1D10v1-Fc and hexavalent 3x1D10v6-Fc in Jurkat cells that express OX40 and which comprise a luciferase gene downstream of an OX40 response element.

The results of that experiment are shown in FIG. 4. Maximal binding (Bmax) and enzyme concentration at 50% response ($K_D$) show that 3x1D10v6-Fc has comparable activity in an OX40 luciferase reporter assay as 3x1D10v1-Fc.

Example 4: Hexavalent 3x1D10v6-Fc has Superior OX40 Agonist Activity

To demonstration that hexavalent 3x1D10v6-Fc is a superior OX40 agonist compared to bivalent and tetravalent versions (SEQ ID NOs: 13 and 16, respectively), the OX40 luciferase reporter assay substantially as described in Example 3 was used.

Figure 5:
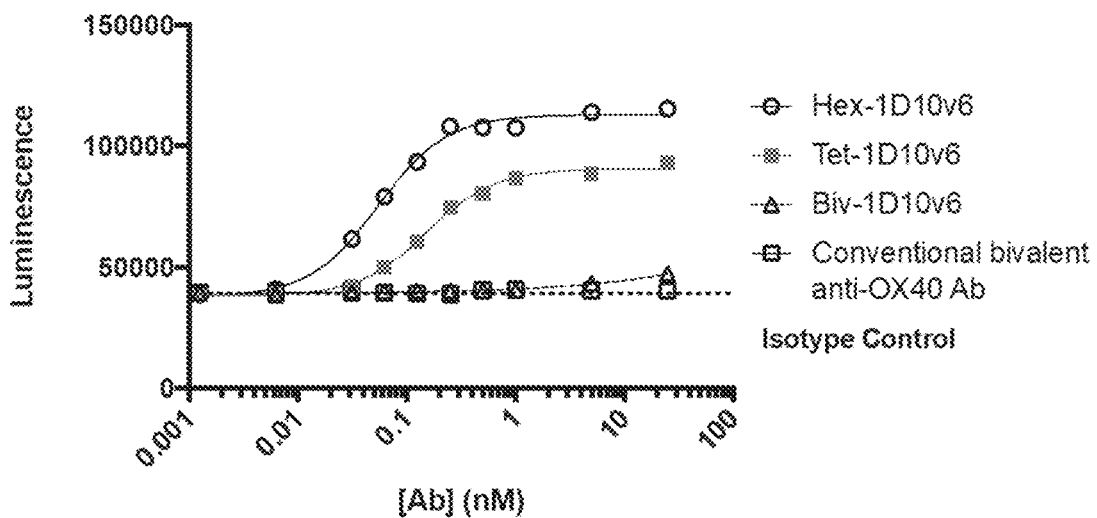
FIG. 5 shows luciferase expression in Jurkat cells that express OX40 and which comprise a luciferase gene downstream of an OX40 response element contacted with hexavalent 3x1D10v6-Fc, tetravalent 2x1D10v6-Fc, and bivalent 1D10v6-Fc.

The results of that experiment are shown in FIG. 5. Hexavalent 3x1D10v6-Fc was superior to tetravalent 2x1D10v6-Fc in this assay, indicating that 3x1D10v6-Fc is a superior agonist. Bivalent 1D10v6-Fc showed minimal activity in this assay.

Example 5: Hexavalent 3x1D10v6-Fc Increases T Cell Proliferation

PBMC isolation: PBMC were isolated from normal human donor leukapheresis or whole blood samples using density gradient centrifugation, as follows. Blood samples were diluted with PBS/2% FBS (1:2) and 30 ml of diluted blood was layered onto 15 ml Lymphoprep (Stemcell Technologies) density gradient medium. After centrifugation at 800×g for 30 minutes, the PBMC layer at the interphase of plasma and lymphoprep was removed and remaining red blood cells were lysed using red blood cell lysis buffer (BioLegend) for 5 minutes at room temperature. Cells were washed in PBS and then frozen fresh in Cryostor CS10 (Stemcell Technologies) at $100 \times 10^6$ cells per ml.

T cell enrichment: Non-T cell populations were labeled with biotinylated anti-lineage marker antibodies against CD14, CD16, CD19, CD20, CD36, CD56, CD123, TCRγ/δ (BioLegend) for 20 minutes at room temperature. Non-T cell populations were then depleted by incubating for 20 minutes at room temperature with magnetic streptavidin particles (500 μl bead slurry plus 500 μl cell suspension per $100 \times 10^6$, 2×8 minutes incubation on the magnet). The unbound cell supernatant contains T cells. Alternatively, T cells were enriched from PBMC samples using the Easy Sep Human T cell Enrichment Kit (Stemcell Technologies) according to the manufacturer's recommendations. To yield enriched $CD4^+$ T cells, enriched T cells were incubated with a biotinylated anti-CD8 antibody and depleted using magnetic streptavidin particles substantially as described above.

Coating of M-450 tosylactivated beads: Stimulator beads for the T cell activation assay were coated with 200 μg mouse anti-human CD3 antibody (clone OKT3; eBioscience) per $4 \times 10^8$ beads according to the manufacturer's recommended coating procedure. In brief, beads were washed once in buffer 1 (0.1 M sodium phosphate buffer, pH 7.4-8.0) and then incubated in a tube rotator for 18 hours at room temperature in buffer 1 containing 200 μg anti-human CD3 antibody. Beads were then washed 4 times with buffer 2 (PBS, 0.1% BSA, 2 mM EDTA pH 7.4). Free tosyl groups were deactivated by incubation of beads for 4 hours at 37° C. in buffer 3 (0.2 M Tris, 0.1% BSA, pH 8.5). Beads were then washed once in buffer 2 and resuspended to a concentration of $400 \times 10^6$ beads/ml.

Co-stimulation assay: Enriched $CD4^+$ T cells (from four different donors) were labeled with CellTrace Violet (CTV; Invitrogen) at a dilution of 1:1000. Cells were then plated in triplicate at 200,000 cells per well in round bottom 96-well plates and combined with 100,000 anti-human CD3 antibody-coated beads. Cultures were incubated with a titration of 3x1D10v6-Fc or bivalent 1D10v6-Fc starting at a final concentration of 50 nM and titrating across the plate 1:5. The final culture volume was 200 μl per well and cells were incubated at 37° C./5% $CO_2$ for 4 days.

FACS staining: On day 4 of the T cell culture, cells were washed once in 150 μL of FACS buffer and cell pellets were resuspended in 50 μl of a surface marker staining solution (containing antibodies to CD4, CD25, and CD71 and propidium iodide). Cells were incubated for 20 min at room temperature before the final wash and analysis on the SONY Analyzer flow cytometer. FlowJo software was used for analysis of the T cell populations. Raw mean fluorescence intensities for different activation markers were then exported and analyzed using Excel and GraphPad PRISM. Values were graphed and titration curves were fitted to assess a dose-response relationship using the [Agonist] vs response—Variable slope (four parameters) nonlinear curve fit. This fit was also used to determine effective concentration (EC50) for each donor.

FACS gating strategy: To assess the level of T cell proliferation and level of activation marker expression on T cell subpopulations, the following gating strategy was used: cellular debris was excluded by FSC/SSC size exclusion, and dead cells were excluded based on their positive propidium iodide signal. Single cells were selected using FSC-A/FSC-H doublet and aggregate exclusion. The remaining cell population was confirmed to be $CD4^+$. Loss of CellTrace Violet ($CTV^+$) staining compared to a T cell only control was a sign of cell proliferation. Increasing MFI levels of activation markers CD25 and CD71 were indications of T cell activation.

IFNγ ELISA and data analysis: On day 4 cell culture supernatant samples were taken and stored at −80° C. Levels of IFNγ in the cell culture supernatants were measured using an IFNγ ELISA kit according to the manufacturer's protocol. In brief, ELISA plates were coated with an anti-IFNγ capture antibody over night at 4° C. The next day, plates were blocked for 1 hour in assay buffer before incubating the cell supernatants for 2 hours. Samples were diluted 1:25 in assay buffer. Antigen binding was detected by incubating the plates for 1 hour with a biotinylated detection antibody and subsequent incubation with a horseradish peroxidase-conjugated streptavidin reagent. HRP activity was measured after addition of a substrate solution and incubation for 15 minutes. After adding a stop solution plates were analyzed on the Emax precision microplate reader at a wavelength of 450 nm.

Raw values from the Emax precision microplate reader were analyzed using the microplate reader's Softmax Pro analysis software. Sample IFNγ levels in pg/ml were calculated using the absorbance values of a standard curve and four parameter logistic regression. Analyzed values were exported into Excel (Microsoft, Version 15.27) for further data analysis. Values were graphed using PRISM (GraphPad Software Inc., Version 7.0c) and titration curves were fitted to assess a dose-response relationship using the [Agonist] vs response—Variable slope (four parameters) nonlinear curve fit.

Figure 6:
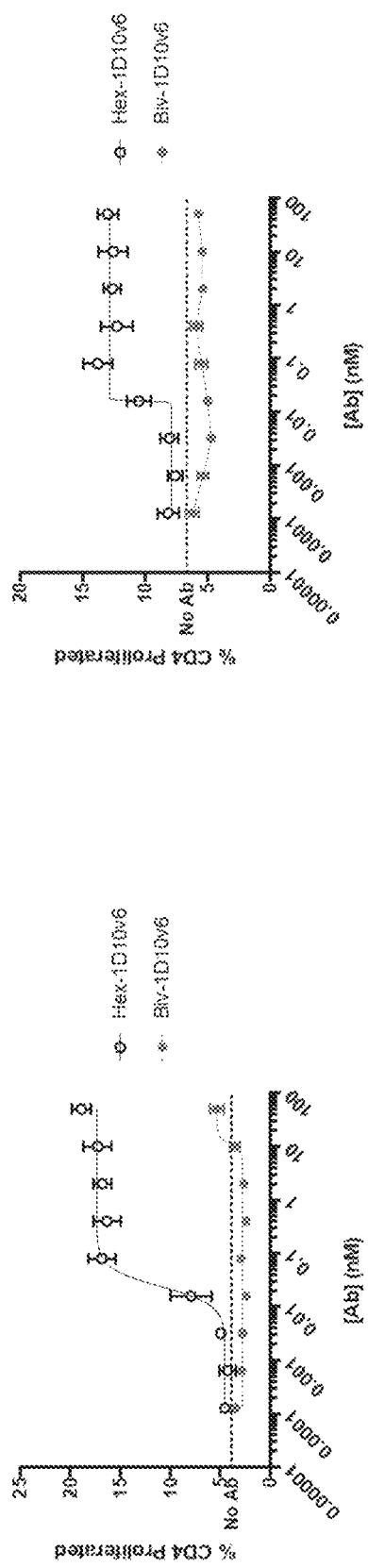
FIG. 6 shows dose-dependent proliferation of $CD4^+$ T cells from four different donors (L556, Leuko 20, Leuko 22, and Leuko 9) co-stimulated with hexavalent 3x1D10v6-Fc and bivalent 1D10v6-Fc.
Figure 6:
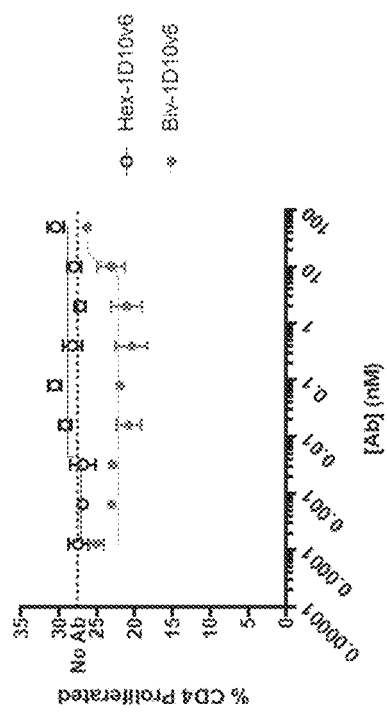
Figure 6:
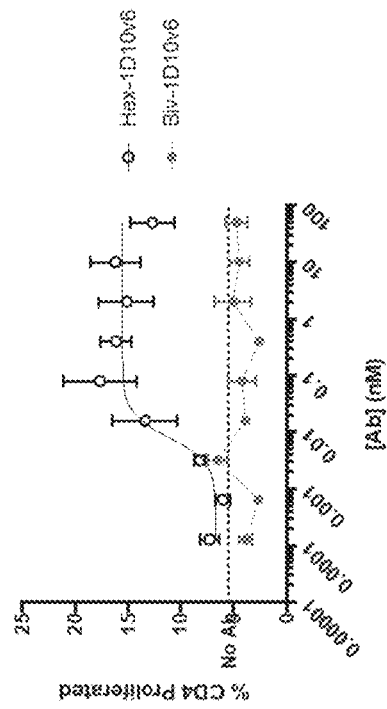
Figure 7:
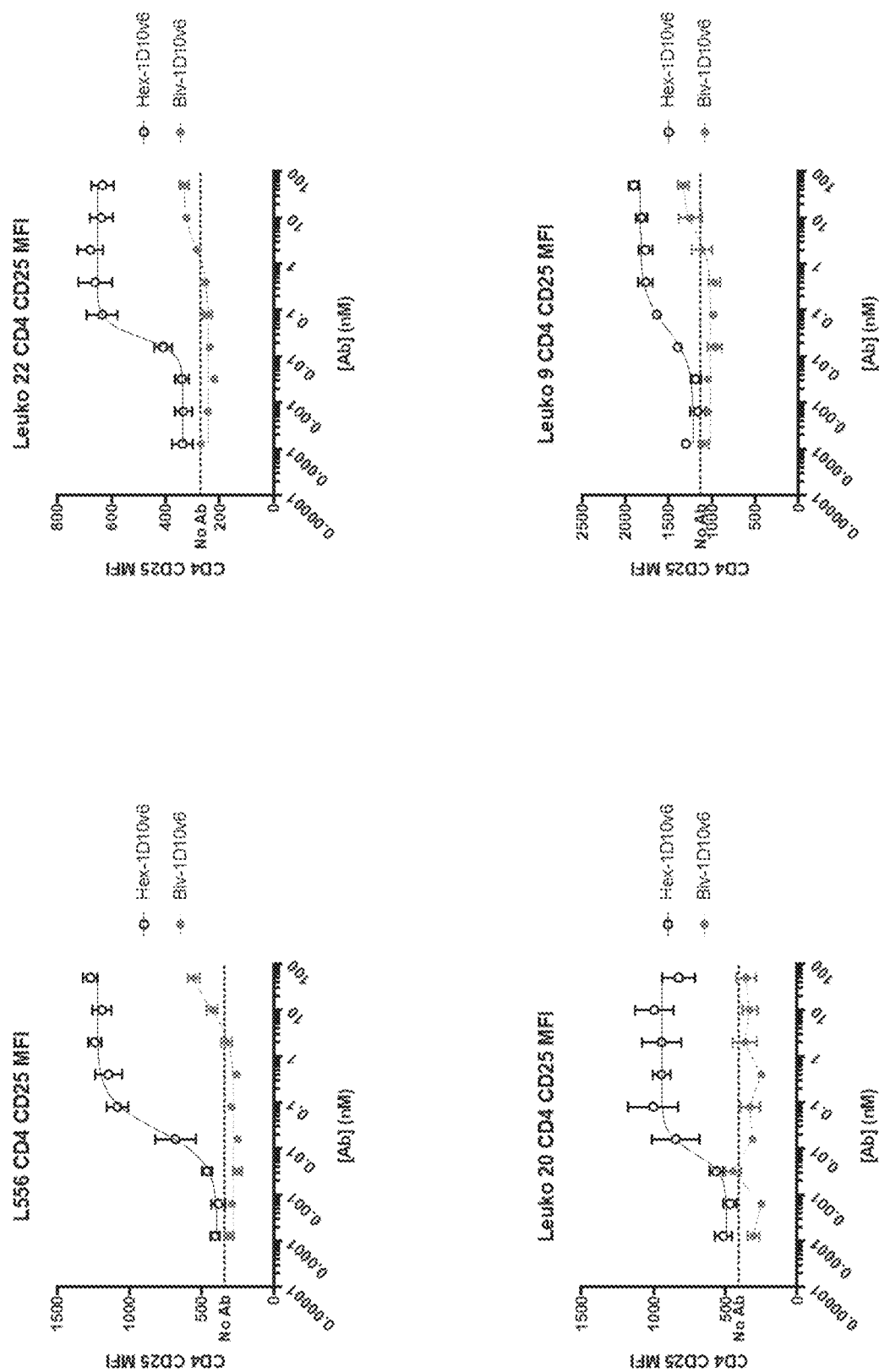
FIG. 7 shows dose-dependent increase of $CD25^+$ expression on $CD4^+$ T cells from four different donors (L556, Leuko 20, Leuko 22, and Leuko 9) co-stimulated with hexavalent 3x1D10v6-Fc and bivalent 1D10v6-Fc.
Figure 8:
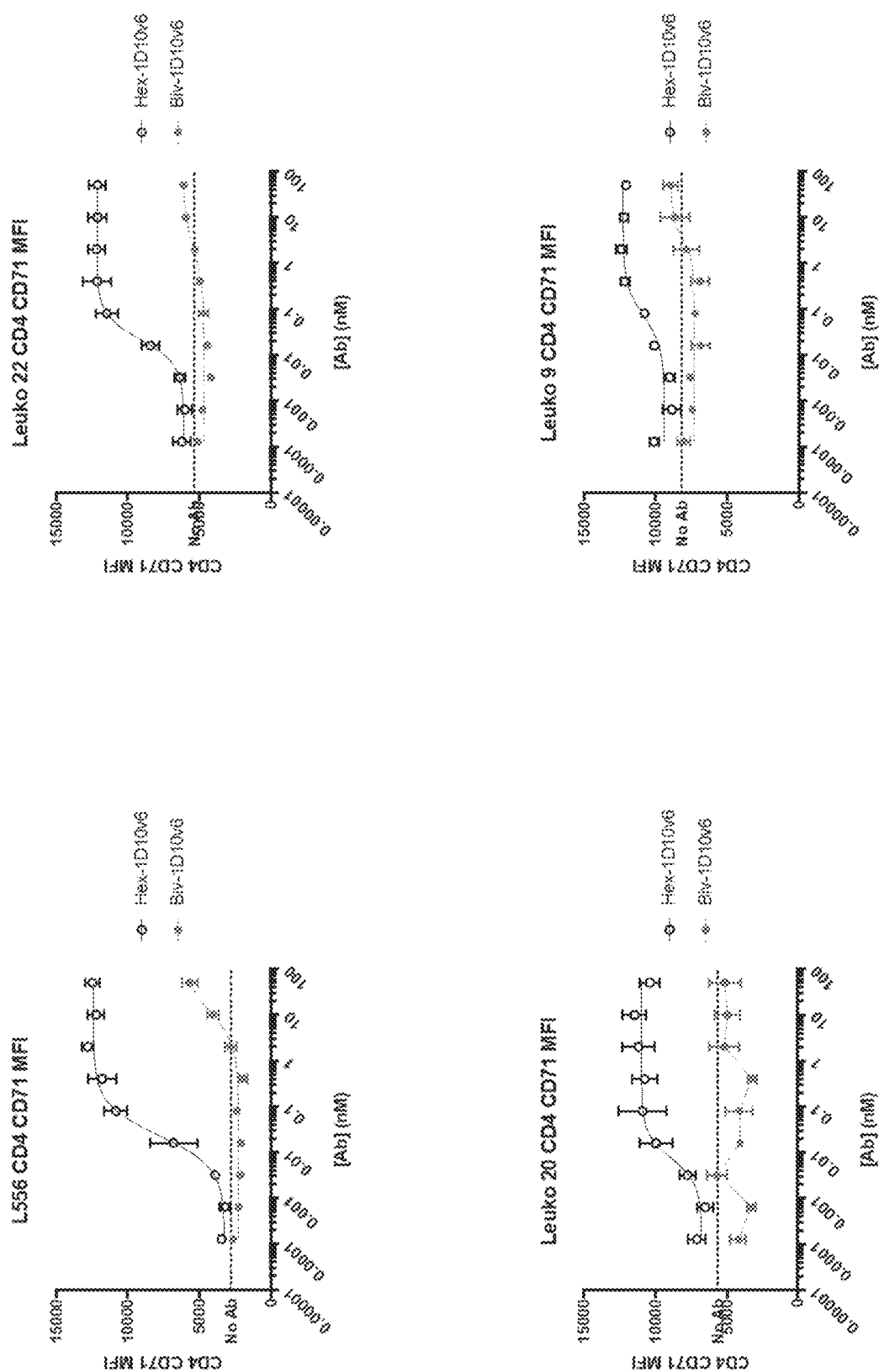
FIG. 8 shows dose-dependent increase of $CD71^+$ expression on $CD4^+$ T cells from four different donors (L556, Leuko 20, Leuko 22, and Leuko 9) co-stimulated with hexavalent 3x1D10v6-Fc and bivalent 1D10v6-Fc.
Figure 9:
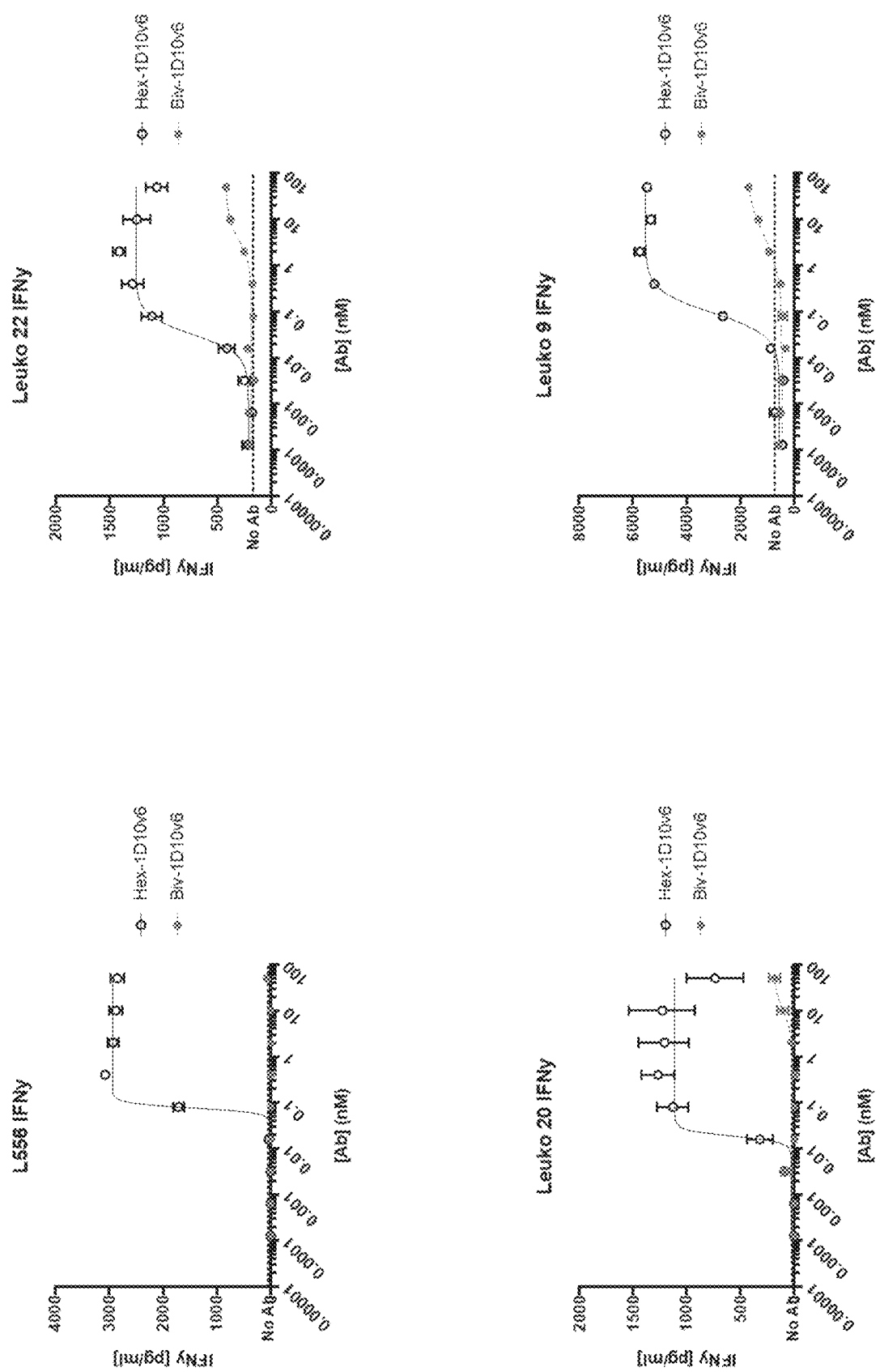
FIG. 9 shows dose-dependent increase of secreted IFNγ from $CD4^+$ T cells from four different donors (L556, Leuko 20, Leuko 22, and Leuko 9) co-stimulated with hexavalent 3x1D10v6-Fc and bivalent 1D10v6-Fc.

As shown in FIG. 6, treatment with the hexavalent 3x1D10v6-Fc, but not with bivalent 1D10v6-Fc, leads to increased $CD4^+$ T cell proliferation from all four donors. Treatment with hexavalent 3x1D10v6-Fc also resulted in higher levels of the activation markers CD25 and CD71 in all four donors (FIG. 7 and FIG. 8). Secreted IFNγ levels were also higher upon treatment with 3x1D10v6-Fc (FIG. 9). The intensity of the co-stimulation varied by donor, but were generally dose-dependent. The calculated EC50 values are summarized in Table 2 below.

TABLE 2

| EC50 values for 3x1D10v6-Fc: | | | | |
|---|---|---|---|---|
| EC50 [nM] | L556 | Leuko 22 | Leuko 20 | Leuko 9 |
| IFNγ | 0.077 | 0.032 | 0.019 | 0.094 |
| CD4 Proliferation | 0.024 | 0.016 | 0.008 | 0.004 |

TABLE 2-continued

EC50 values for 3x1D10v6-Fc:

| EC50 [nM] | L556 | Leuko 22 | Leuko 20 | Leuko 9 |
|---|---|---|---|---|
| CD4+ CD25 MFI | 0.026 | 0.026 | 0.008 | 0.04 |
| CD4+ CD71 MFI | 0.032 | 0.022 | 0.007 | 0.069 |

In summary, 3x1D10v6-Fc improved anti-CD3 antibody-mediated stimulation of T cells in vitro. Without intending to be bound by any particular theory, it appeared that effective co-stimulation in this assay required clustering of OX40, for example, with hexavalent 3x1D10v6-Fc.

Example 6: Hexavalent 3x1D10v6-Fc Enhances T Cell Costimulation and IFNγ Production Enriched T cells from 10 healthy human donors were stimulated with suboptimal anti-CD3 antibody in the presence or absence of 3x1D10v6-Fc.

PBMCs were isolated from 10 healthy human donors, and T cell populations were enriched substantially as described in Example 5.

T cell stimulation: Enriched T cells from 10 healthy donors were thawed and washed twice using CTL anti-aggregate media. T cells were labeled with the proliferative dye CellTrace Violet (CTV) (ThermoFisher) for 10 minutes at 37° C. After washing, T cells were resuspended to $1.5 \times 10^6$ cells/ml in RPMI supplemented with 10% FBS and 1× antibiotic/antimycotic and 150,000 T cells were added per well in 100 µl in a flat-bottom 96-well plate. M-450 Tosy-lactivated Dynabeads (ThermoFisher) were coated overnight with 200 µg of anti-CD3 antibody (clone OKT3, eBioscience) following the manufacturer's instructions. Anti-CD3 antibody coated beads were added in 50 µl per well to the labeled T cells at a 1:2 ratio to provide a primary T cell stimulus. 3x1D10v6-Fc was added in 50 µl at a final concentration of 10 nM. Plates were incubated at 37° C./5% $CO_2$ for 3 days and analyzed by flow cytometry.

Flow Cytometry: After 3 days. T cells were spun down and labeled in FACS buffer (PBS/2% FBS/0.05% sodium azide) with the viability marker propidium iodide (PI) along with the following fluorescently labeled antibodies: CD4-PE, CD8-APC, CD25-FITC, and CD71-PE/Cy7 (Biolegend) for 20 minutes at room temperature. T cells were washed and resuspended in 70 µl of FACS buffer and analyzed using the Sony SA3800 spectral analyzer. Flowjo software was used to gate on live (PI-) CD4 and CD8 populations and the percentage of cells that underwent proliferation was determined by gating on T cells that underwent a minimum of one division as determined by CTV dilution. The percentage of CD4 and CD8 T cells expressing the activation markers CD25 and CD71 was determined by comparing to non-stimulated T cell populations. The data was exported into Microsoft Excel and graphed using Prism.

Intracellular Cytokine Staining: Cells were spun down and surface labeled with PE-conjugated anti-CD4 antibody and APC-conjugated anti-CD8 antibody along with the Zombie Red viability stain (BioLegend) for 20 minutes at room temperature in FACS buffer (2% FBS/0.1% Sodium Azide in PBS). After washing, the cells were fixed for 30 minutes with BD Fix/Perm buffer. Cells were washed with 1× BD Perm/Wash buffer and labeled with PE/Cy7 anti-IFNγ antibody in Perm/Wash buffer for 45 minutes at room temperature. After washing, cells were resuspended in FACS buffer and read on the Sony SA3800 spectral analyzer. Data analysis of CD4+ and CD8+ T cell populations was performed using Flowjo software and graphed using Prism.

Figure 10:
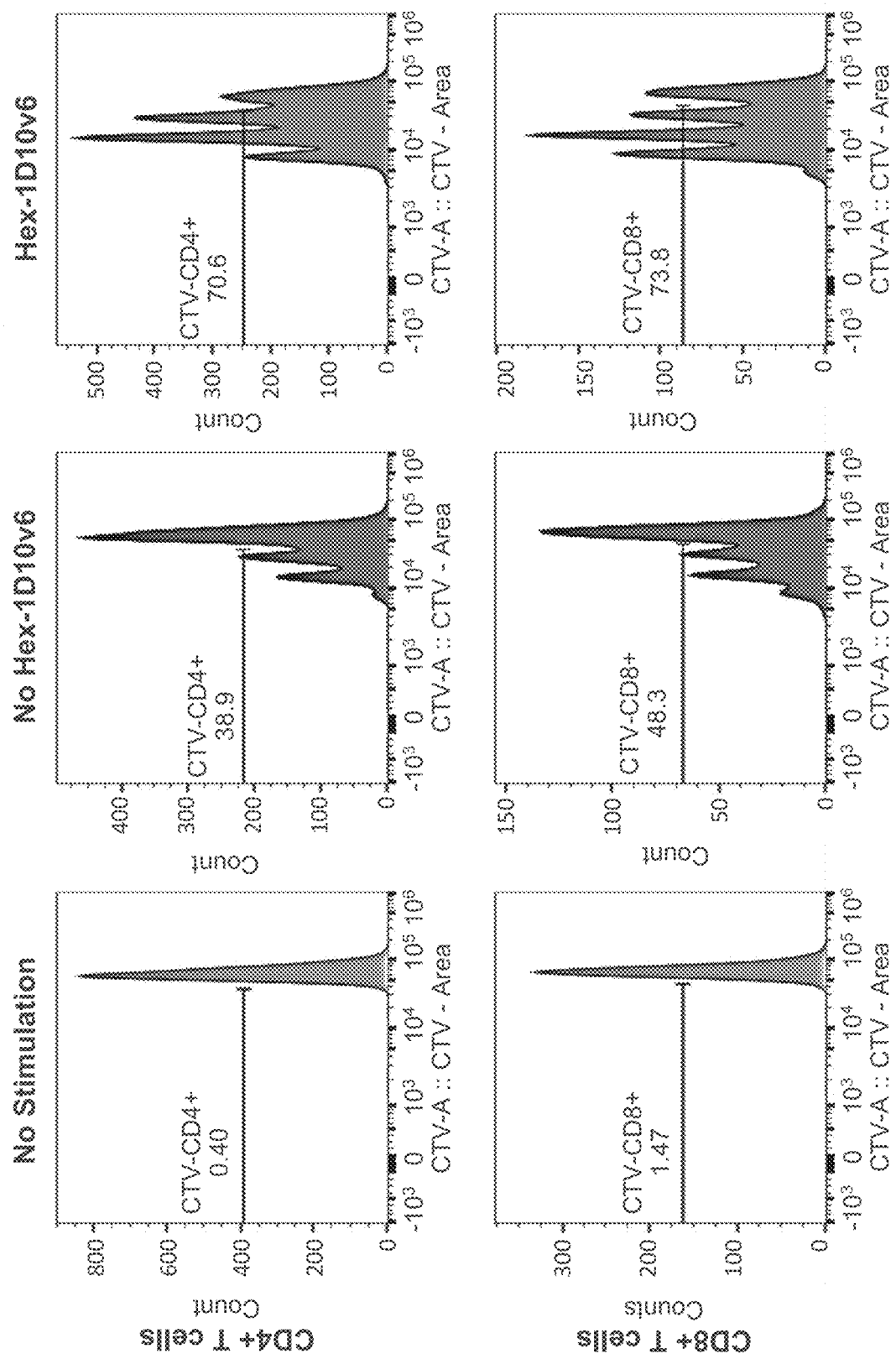
FIG. 10 shows an increase in $CD4^+$ T cells and $CD8^+$ T cells following co-stimulation of human T cells with anti-CD3 antibody and hexavalent 3x1D10v6-Fc ("No Antibody" indicates anti-CD3 antibody stimulation without hexavalent 3x1D10v1-Fc).
Figure 11:
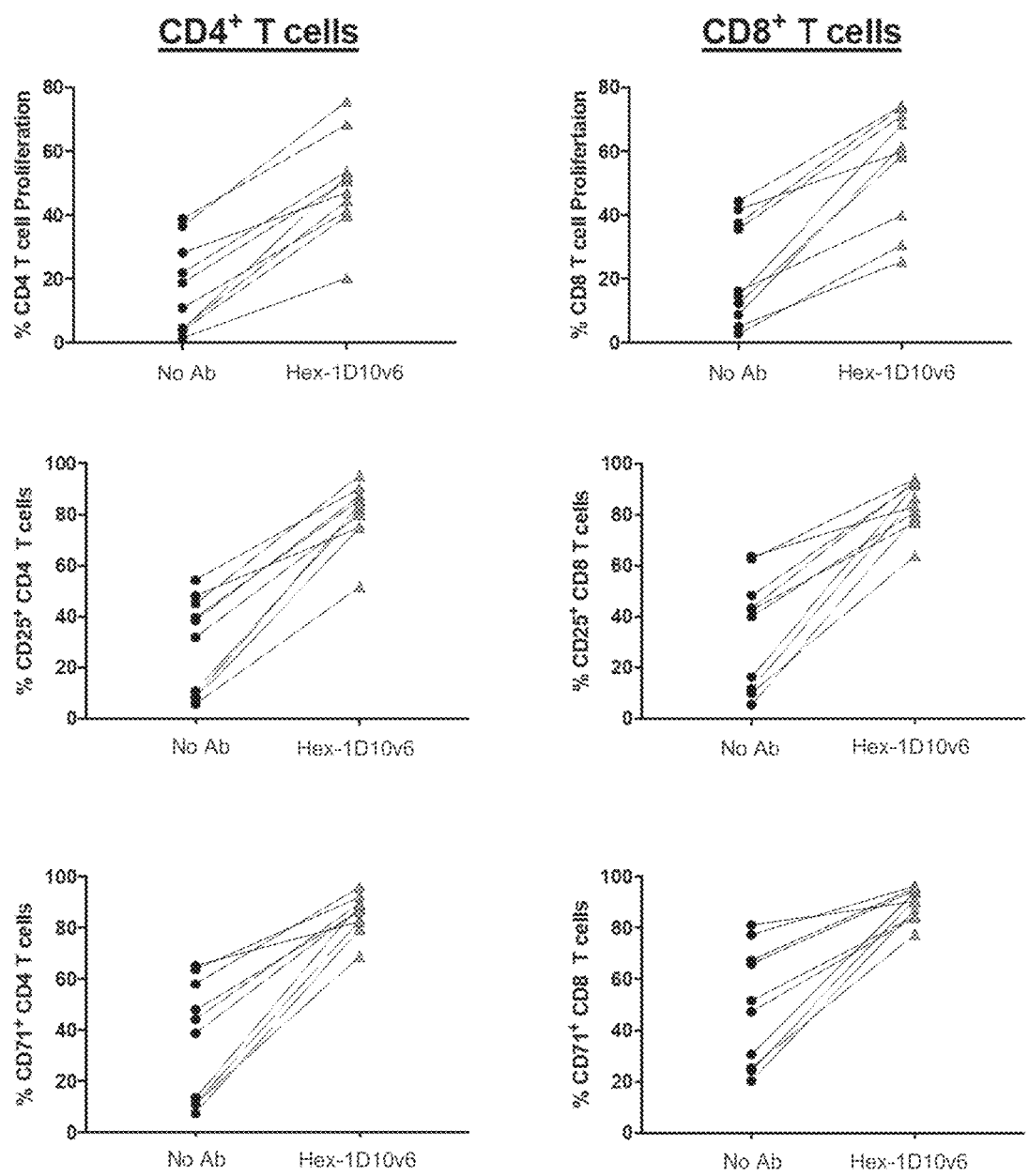
FIG. 11 shows increased $CD4^+$ and $CD8^+$ T cell proliferation (top two panels), increased percentages of $CD25^+$ $CD4^+$ and $CD25^+$ $CD8^+$ T cells (middle two panels), and increased percentages of $CD71^+$ $CD4^+$ and $CD71^+$ $CD8^+$ T cells (bottom two panels), following co-stimulation of T cells from 10 healthy donors with hexavalent 3x1D10v6-Fc.
Figure 12:
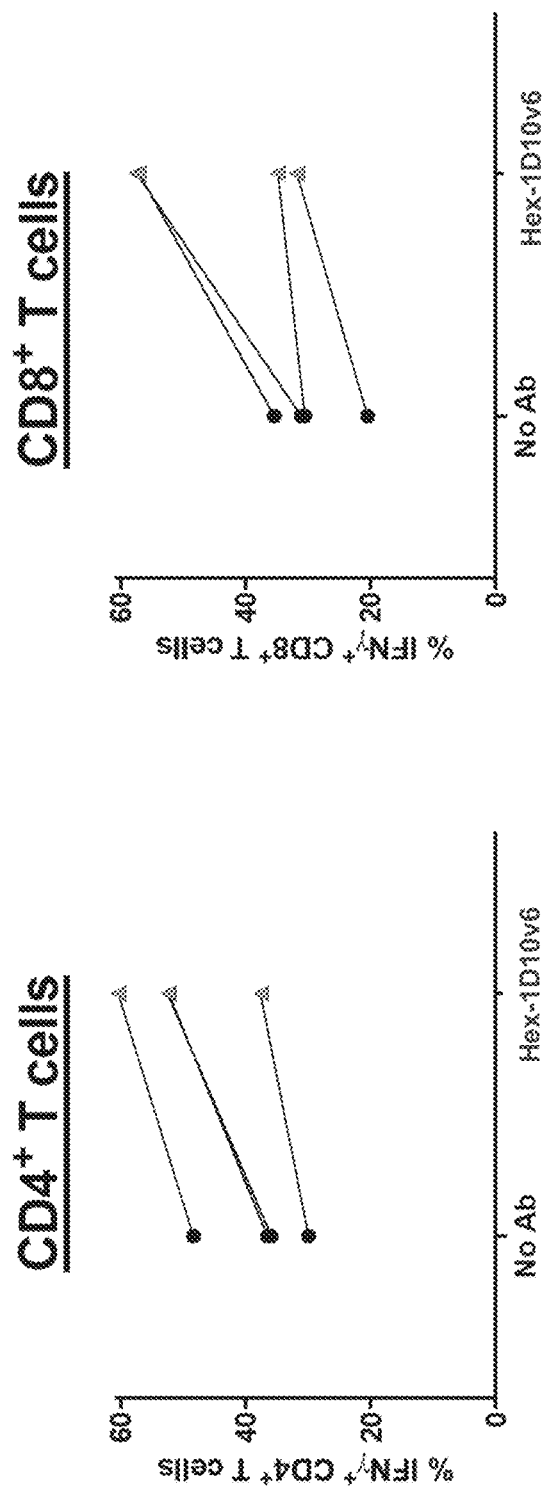
FIG. 12 shows increased percentages of intracellular IFNγ$^+$ $CD4^+$ and intracellular IFNγ$^+$ $CD8^+$ T cells following co-stimulation of T cells from 4 healthy donors with hexavalent 3x1D10v6-Fc.

In T cells from all 10 of the donors tested, 3x1D10v6-Fc treatment led to a significant increase in the percentage of CD4+ and CD8+ T cells that underwent proliferation in response to anti-CD3 antibody stimulation (FIG. 10. FIG. 11). Moreover, the percentage of CD4 and CD8 T cells that expressed the activation markers CD25 and CD71 was increased with 3x1D10v6-Fc treatment (FIG. 11). In a separate experiment, a smaller subset of 4 donors showed an increase in intracellular IFNγ levels in both T cell subsets following treatment with 3x1D10v6-Fc (FIG. 12). Thus, 3x1D10v6-Fc provides a potent costimulatory signal to T cells, leading to enhanced activation, proliferation and effector function.

Example 7: Hexavalent 3x1D10v6-Fc Reverses Treg-Mediated Suppression of CD4+ T Cell Proliferation T cell Enrichment: Tregs and conventional CD4+ T cells were enriched from fresh, healthy donor PBMCs by using an Easy Sep Human CD4+CD127$^{low}$CD25+ regulatory T cell isolation kit (Stemcell) following the manufacturer's instructions.

T cell Suppression Assay: In order to distinguish the two populations of cells, enriched Tregs and CD4+ responder T cells were labeled with the proliferative dyes CellTrace Violet (CTV) and CFSE, respectively, for 10 minutes at 37° C. After washing, Tregs and CD4+ T cells were resuspended to $1.5 \times 10^6$ cells/ml in RPMI supplemented with 10% FBS and 1× antibiotic/antimycotic. Tregs were seeded in 50 µl volume yielding 75,000 Tregs/well in a 96-well round-bottom plate. Tregs were incubated overnight at 37° C. in the presence of 10 nM of anti-OX40 hexavalent 3x1D10v6-Fc, 10 nM of a conventional (HC/LC) bivalent anti-OX40 antibody, or in the absence of an antibody. In parallel, labeled CD4+ responder T cells were activated overnight at 37° C. with anti-CD3 coated dynabeads at a 1:2 bead to T cell ratio. The next day, the Treg plate was washed 2× with media to remove the antibodies. Stimulated responder CD4+ T cells were added in 100 µl of media delivering 150,000 CD4+ T cells/well to the plate containing Tregs at a ratio of 1 Treg for every 2 CD4+ responder T cells. Hexavalent 3x1D10v6-Fc or conventional bivalent anti-OX40 antibody were added back in 100 µl of media at a final concentration of 10 nM in duplicate to a subset of the cells. In addition, a group of CD4+ responder T cells was included that was not co-incubated with Tregs. The plate was incubated at 37° C./5% $CO_2$ for 3 days and analyzed by flow cytometry.

Flow Cytometry: After 3 days. T cells were spun down and labeled in FACS buffer (PBS/2% FBS/0.05% sodium azide) with the viability marker propidium iodide (PI) along with the following fluorescently labeled antibodies: CD4-PE, CD25-APC, and CD71-PE/Cy7 (Biolegend) for 20 minutes at room temperature. T cells were washed and resuspended in 70 µl of FACS buffer and analyzed using the Sony SA3800 spectral analyzer. Flowjo software was used to gate on live (PI-) CFSE+ responder CD4+ or CTV+ Treg populations and the percentage of cells that underwent proliferation was determined by gating on responder T cells that underwent a minimum of one division as determined by CFSE dilution. The percentage of responder CD4+ T cells expressing the activation markers CD25 and CD71 was determined by comparing to non-stimulated T cell populations. The data was exported into Microsoft Excel and graphed using Prism.

Figure 13:
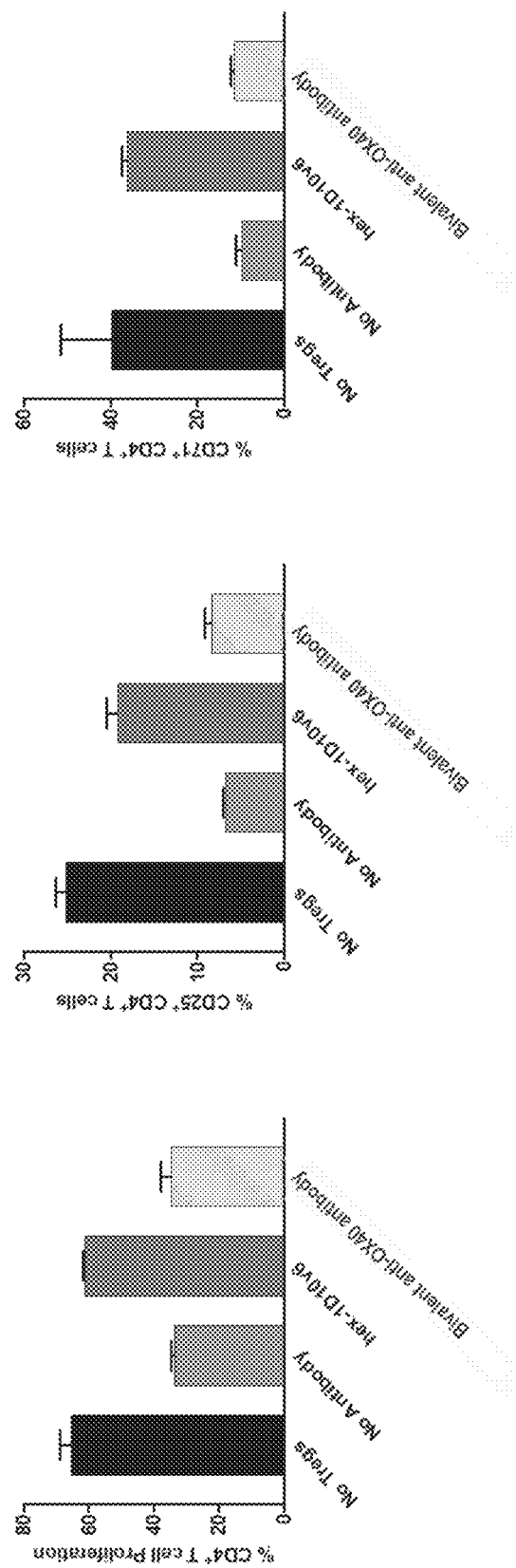
FIG. 13 shows that treatment with hexavalent 3x1D10v6-Fc reversed Treg-mediated suppression of responder $CD4^+$ T cell proliferation and increased the percentage of $CD4^+$ T cells expressing the activation markers CD25 and CD71.

Stimulation with anti-CD3 coated beads for a total of 4 days led to the proliferation of 66% of responder CD4+ T cells (FIG. 13). The addition of enriched Tregs to the culture led to a dramatic reduction in responder CD4+ T cell proliferation (34% proliferated). Treatment with 10 nM of hexavalent 3x1D10v6-Fc led to near complete recovery of responder CD4+ T cell proliferation (62% proliferated). Moreover, the expression of the T cell activation markers CD25 and CD71 were restored to similar levels to the CD4+ T cell responders without Treg experimental group. In contrast, treatment with the conventional bivalent anti-OX40 antibody failed to restore CD4+ T cell proliferation or increase the expression of CD25 or CD71 relative to the no antibody group.

Example 8: Hexavalent 3x1D10v6-Fc in Combination with Pembrolizumab Potentiates T Cell Activation Following TCR engagement, costimulatory molecules like OX40 are upregulated alongside negative regulatory molecules, which oppose T cell activation by dampening TCR signaling. Clinically, blockade of one such pathway, the PD-1/PD-L1 axis, has been shown to successfully restore the function of unresponsive tumor-specific T cells, by relieving this inhibitory signal. OX40 achieves a similar outcome, the enhancement of T cells responses, via a different mechanism: providing exogenous costimulatory signals that synergize with TCR signals. These non-overlapping but complementary mechanisms suggest that combining OX40 agonism with checkpoint blockade will achieve greater clinical benefit.

The allogeneic mixed lymphocyte reaction (MLR) is an in vitro assay used to demonstrate functional modulation of T cells; it utilizes a mixture of in vitro-derived immature dendritic cells (iDCs) and HLA mismatched T cells to induce TCR-dependent T cell activation. Hexavalent 3x1D10v6-Fc has been shown to have modest activity in this assay. (Data not shown.) The activity of hexavalent 3x1D10v6-Fc was tested in combination with anti-PD-1 antibody pembrolizumab to determine whether the combination exhibits increased T cell activation.

CD4+ T cell isolation: PBMCs were isolated from human donor blood leukopak using density gradient centrifugation, substantially as follows. Blood samples were diluted with PBS/2% FBS (1:2) and 30 mL of diluted sample was layered onto 15 mL Lymphoprep™ density gradient medium. After centrifugation at 800×g for 30 minutes, the PBMC layer at the interphase of the plasma and Lymphoprep™ was collected and remaining red blood cells were lysed using red blood cell lysis buffer for 7 minutes at room temperature. The PBMCs were then enriched for monocytes as described below, or frozen at $100 \times 10^6$ cells/ml in CryoStor® cryopreservation media and stored in liquid nitrogen. CD4+ T cells were enriched from fresh, healthy donor PBMCs with the EasySep™ Human CD4+ T cell isolation kit (Stemcell Technologies) following the manufacturer's instructions. PBMCs were re-suspended at $50 \times 10^6$ cells/mL in PBS containing 2% FBS and 1 mM EDTA. CD4+ T cells were negatively enriched using a CD4+ T cell isolation cocktail followed by incubation with Dextran RapidSpheres™ in an Easy Sep™ magnet. After two rounds of enrichment on the magnet, CD4+ T cells were counted and washed with PBS/0.1% BSA (CTV buffer). Cells were labeled with CellTrace™ Violet dye (1:1000) at $10 \times 10^6$ cells/mL in CTV buffer for 10 minutes at 37° C. Labeled cells were washed once with PBS/2% FBS and re-suspended at $3.5 \times 10^6$ cells/mL in assay media (RPMI+10% FBS plus penicillin, streptomycin, and amphotericin).

Monocyte enrichment and generation of immature dendritic cells (iDC): Monocytes were enriched from PBMC isolated from leukopak donors using a negative enrichment kit without CD16 depletion according to the manufacturer's protocol (Easy Sep™ human monocyte enrichment kit without CD16 depletion: Stemcell Technologies). In brief, non-monocyte populations were labeled with tetrameric antibody complexes recognizing anti-lineage markers and depleted using magnetic particles. The unbound cell supernatant contained the monocytes. Monocytes were cultured at $1 \times 10^6$ cells/mL in RPMI supplemented with 10% FBS plus penicillin, streptomycin, and amphotericin, 500 U/mL GM-CSF, and 250 U/mL IL-4. Half of the media was replenished every 2 days until immature dendritic cells (iDC) were harvested on day 7 by collecting loosely adherent and suspended cells. Cells were washed in PBS and then frozen fresh in CryoStor® at $3 \times 10^6$ cells per mL. iDC phenotype induction following this regimen was confirmed by flow cytometry using FSC/SSC size exclusion and detecting CD14-CD11c+ HLA-DR+ staining in at least 60% of the population.

Mixed lymphocyte reaction (MLR): Monocyte-derived immature dendritic cells (iDCs) were re-suspended at $0.8 \times 10^6$ cells/mL in assay media. $1.75 \times 10^5$ CD4+ T cells from a different donor were suspended in 50 µL, and mixed with $4 \times 10^4$ iDCs in 50 µl in 96-well U-bottom plates.

Hexavalent 3x1D10v6-Fc was added at an initial assay concentration of 10 nM and titrated across the plate 1:4 in triplicate in either the presence or absence of a constant assay concentration of 10 nM pembrolizumab. In a separate experiment, pembrolizumab was added at an initial assay concentration of 50 nM and titrated across the plate 1:4 in triplicate either the presence or absence of a constant assay concentration of 1 nM hexavalent 3x1D10v6-Fc. The fixed concentration of hexavalent 3x1D10v6Fc (1 nM) was selected based on saturating antibody concentrations that showed maximal activity in the T cell co-stimulation assay, and for pembrolizumab (10 nM), the saturating antibody concentration that gave maximal reporter activity in the PD1/PD-L1 blockade assay. All assay plates were incubated at 37° C. for 7 days.

Human IL-2 ELISA: Aliquots of assay supernatant were collected on day 3 to determine human IL-2 concentration by ELISA using the Human IL-2 ELISA MAX™ Deluxe kit (Biolegend) following the manufacturer's instructions. ELISA MaxiSorp plates were coated overnight with human IL-2 capture antibody, washed then blocked with diluent buffer for an hour. Standard curves were prepared in duplicate from an initial concentration of 1000 pg/mL IL-2, and assay supernatant samples were diluted 1:5 or 1:10 in diluent buffer. Samples and standards were incubated on ELISA plates for two hours, followed by washes and incubation with detection antibody for an hour. Assay plates were washed and incubated with horseradish peroxidase (HRP)-conjugated streptavidin for 30 minutes. After a final wash step, captured human IL-2 was detected on the ELISA plates with the provided substrate solution. The detection reaction was stopped after 10-30 minutes with an equal volume of 1M HCl. The absorbance values at 450 nm were read on an EMaxR plate reader (Molecular Devices), and the concentrations of human IL-2 in the MLR assay supernatants calculated from the standard curves.

Figure 14A:
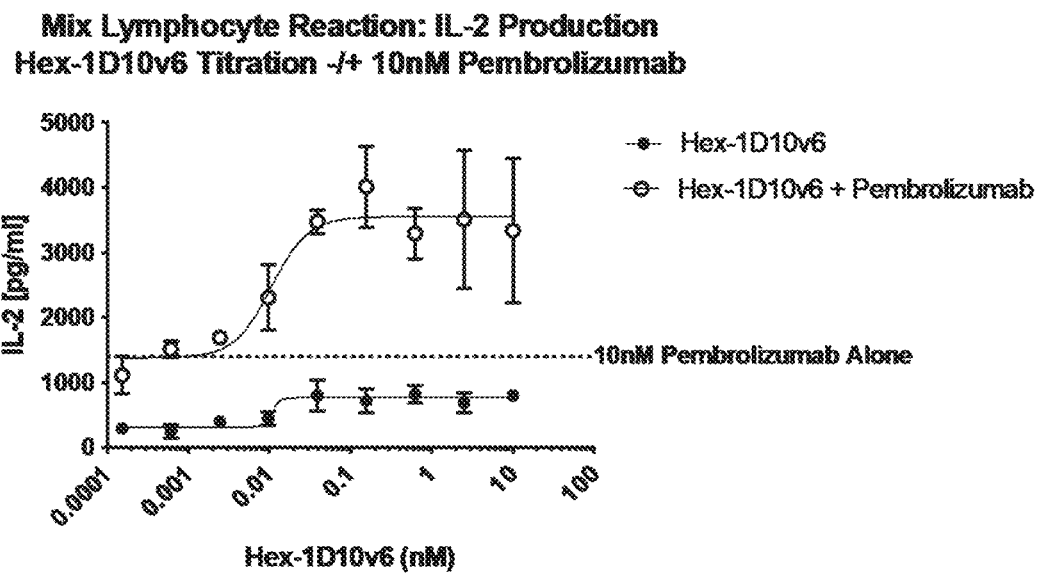
FIG. 14A-14B show that the combination of pembrolizumab, an antibody targeting PD-1, and hexavalent 3x1D10v6-Fc (Hex-1D10v6) enhanced IL-2 production in a mixed lymphocyte reaction (MLR).
Figure 14B:
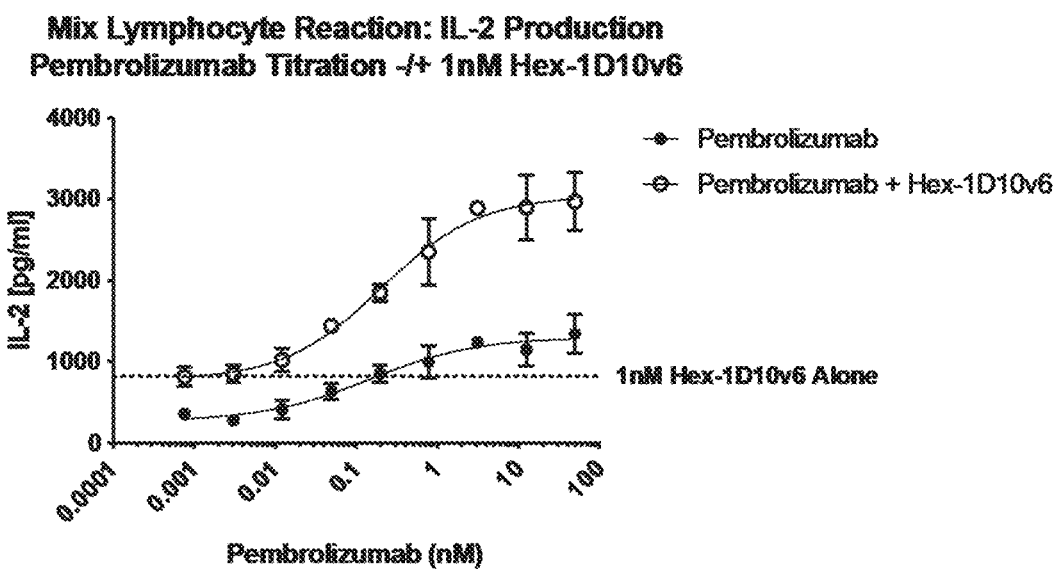

As shown in FIG. 14A-14B, the combination of pembrolizumab and hexavalent 3x1D10v6-Fc enhanced the IL-2 production from CD4+ T cells in a mixed lymphocyte reaction (MLR). These results demonstrate the benefit of combining PD-1/PD-L1 axis blockade with OX40 agonism.

Example 9: Assessment of Pharmacokinetic Properties of Hexavalent 3x1D10v6-Fc

The pharmacokinetic (PK) properties and the toxicokinetic profile of a therapeutic agent is important for understanding dose/exposure relationships, rate of clearance, and the safety profile. Attenuated exposure and or an accelerated clearance profile can reveal liabilities in the agent itself due to non-specific interactions, poor stability, or immunogenicity: or in the target as evidenced by toxicity or changes in drug disposition. Typically, the PK properties of therapeutic antibodies is assessed in rodents and/or in non-human primates. A poor PK in these models may be indicative of non-specific binding and rapid clearance of the antibody.

Hexavalent 3x1D10v6Fc was administered via intravenous injection to cynomolgus monkeys (5 males and 5 females per group) at 5 mg/kg, 20 mg/kg and 60 mg/kg. A quantitative ELISA method was used to determine serum concentrations of hexavalent 3x1D10v6-Fc, substantially as follows. Microplate wells were pre-coated with a recombinant form of the extracellular domain of human OX40 fused to a mouse Fc domain (OX40-mFc). After blocking and washing, a titration of hexavalent 3x1D10v6-Fc (for a standard curve), control samples containing pre-determined concentrations of hexavalent 3x1D10v6-Fc, and test samples were added to the wells and incubated to allow hexavalent 3x1D10v6Fc contained in the samples to bind the immobilized OX40-mFc. Plates were washed, and an Fcγ fragment-specific, horseradish peroxidase (HRP) conjugated anti-human IgG secondary antibody was added to detect plate-bound hexavalent 3x1D10v6Fc. A solution containing the HRP substrate tetramethylbenzidine (TMB) was added to wells, which results in a colorimetric signal that is proportional to the concentration of HRP-conjugated anti-human IgG antibody bound to hexavalent 3x1D10v6-Fc. The reaction was stopped by addition of an acidic solution and absorbance at 450 nm was determined. For control and test samples, the conversion of spectrophotometric absorbance (quantitated by optical density [OD450]) values into concentration was performed by comparison to a concurrently analyzed calibration curve regressed according to a 4-PL/logistic model. The lower limit of quantitation (LLOQ) of hexavalent 3x1D10v6Fc in serum by this method was 100 ng/mL.

Figure 15:
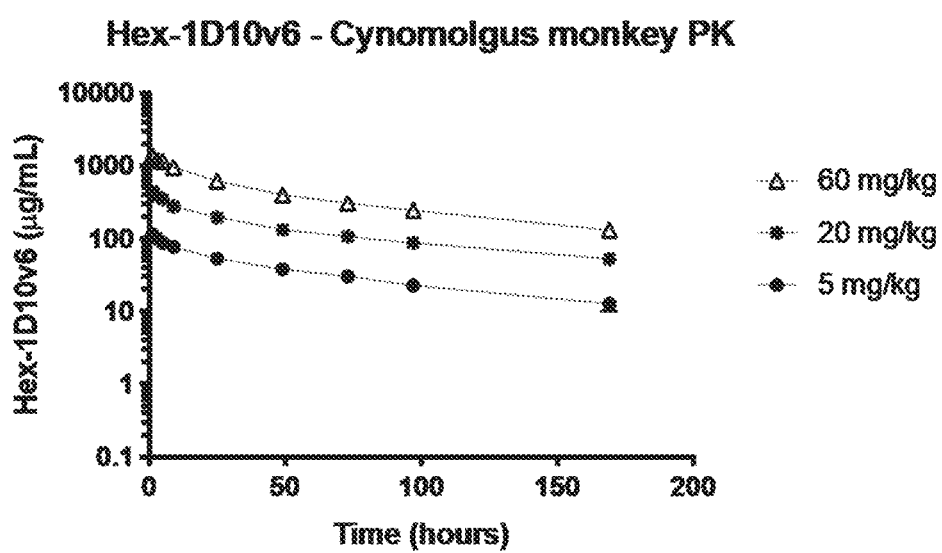
FIG. 15 shows the pharmacokinetic (PK) profile of 5 mg/kg, 20 mg/kg, or 60 mg/kg hexavalent 3x1D10v6-Fc (Hex-1D10v6) administered to cynomolgus monkeys. Systemic exposure was achieved and increased proportionally with the dose.

Across the dose range, systemic exposure (Cmax and $AUC_{0-168h}$) was achieved and increased dose-proportionally, without gender differences. Across the dose range from 5 to 60 mg/kg, using a non-compartmental analysis, the average $T_{1/2}$ across groups was 55-89.7 hours, clearance rate (CL) was 0.683-0.832 mL/h/kg, and volume of distribution at steady state (Vdss) was 55.9-86.2 mL/kg. The PK profile of hexavalent 3x1D10v6-Fc is shown in FIG. 15.

These results demonstrate that hexavalent 3x1D10v6-Fc has a good PK profile, suitable for therapeutic applications, and suggests the non-specific binding observed with 1D10v1 has been mitigated.

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

Table of Certain Sequences

| SEQ ID NO | Description | Sequence |
|---|---|---|
| 1 | Human OX40 | MCVGARRLGR GPCAALLLLG LGLSTVTGLH CVGDTYPSND RCCHECRPGN GMVSRCSRSQ NTVCRPCGPG FYNDVVSSKP CKPCTWCNLR SGSERKQLCT ATQDTVCRCR AGTQPLDSYK PGVDCAPCPP GHFSPGDNQA CKPWTNCTLA GKHTLQPASN SSDAICEDRD PPATQPQETQ GPPARPITVQ PTEAWPRTSQ GPSTRPVEVP GGRAVAAILG LGLVLGLLGP LAILLALYLL RRDQRLPPDA HKPPGGGSFR TPIQEEQADA HSTLAKI |
| 2 | Cynomolgus monkey OX40 | MCVGARRLGR GPCAALLLLG LGLSTTAKLH CVGDTYPSND RCCQECRPGN GMVSRCNRSQ NTVCRPCGPG FYNDVVSAKP CKACTWCNLR SGSERKQPCT ATQDTVCRCR AGTQPLDSYK PGVDCAPCPP GHFSPGDNQA CKPWTNCTLA GKHTLQPASN SSDAICEDRD PPPTQPQETQ GPPARPTTVQ PTEAWPRTSQ RPSTRPVEVP RGPAVAAILG LGLALGLLGP LAMLLALLLL RRDQRLPPDA PKAPGGGSFR TPIQEEQADA HSALAKI |
| 3 | 1D10v1 | EVQLLESGGG EVQPGGSLRL SCAASGFTFS DAFMYWVRQA PGKGLEWVSS ISNRGLKTAY AESVKGRFTI SRDNAKNTLY LQMSSLRAED TAVYYCSRDV DGDFRGQGTL VTVKP |
| 4 | 1D10v1 CDR1 | GFTFSDAF |
| 5 | 1D10v1 CDR2 | ISNRGLKT |
| 6 | 1D10v1 CDR3 | SRDVDGDF |
| 17 | 1D10v1 FR1 | EVQLLESGGG EVQPGGSLRL SCAAS |
| 18 | 1D10v1 FR2 | MYWVRQA PGKGLEWVSS |

Table of Certain Sequences

| SEQ ID NO | Description | Sequence |
|---|---|---|
| 19 | 1D10v1 FR3 | AY AESVKGRFTI SRDNAKNTLY LQMSSLRAED TAVYYC |
| 20 | 1D10v1 FR4 | RGQGTL VTVKP |
| 7 | 1D10v1-Fc (bivalent) | EVQLLESGGG EVQPGGSLRL SCAASGFTFS DAFMYWVRQA PGKGLEWVSS ISNRGLKTAY AESVKGRFTI SRDNAKNTLY LQMSSLRAED TAVYYCSRDV DGDFRGQGTL VTVKPGGGGD KTHTCPPCPA PELLGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSRDELTKN QVSLTCLVKG FYPSDIAVEW ESNGQPENNY KTTPPVLDSD GSFFLYSKLT VDKSRWQQGN VFSCSVMHEA LHNHYTQKSL SLSPGK |
| 8 | 3x1D10v1-Fc (hexavalent; also referred to as Hex-1D10v1) | EVQLLESGGG EVQPGGSLRL SCAASGFTFS DAFMYWVRQA PGKGLEWVSS ISNRGLKTAY AESVKGRFTI SRDNAKNTLY LQMSSLRAED TAVYYCSRDV DGDFRGQGTL VTVKPGGSGG SEVQLLESGG GEVQPGGSLR LSCAASGFTF SDAFMYWVRQ APGKGLEWVS SISNRGLKTA YAESVKGRFT ISRDNAKNTL YLQMSSLRAE DTAVYYCSRD VDGDFRGQGT LVTVKPGGSG GSEVQLLESG GGEVQPGGSL RLSCAASGFT FSDAFMYWVR QAPGKGLEWV SSISNRGLKT AYAESVKGRF TISRDNAKNT LYLQMSSLRA EDTAVYYCSR DVDGDFRGQG TLVTVKPGGG GDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVMH EALHNHYTQK SLSLSPGK |
| 9 | 1D10v6 | EVQLLESGGG EVQPGGSLRL SCAASGFTFS DAFMYWVRQA PGKEREWVSS ISNRGLKTAY AESVKGRFTI SRDNAKNTLY LQMSSLRAED TAVYYCSRDV DADFRGQGTL VTVKP |
| 10 | 1D10v6 CDR1 | GFTFSDAF |
| 11 | 1D10v6 CDR2 | ISNRGLKT |
| 12 | 1D10v6 CDR3 | SRDVDADF |
| 21 | 1D10v6 FR1 | EVQLLESGGG EVQPGGSLRL SCAAS |
| 22 | 1D10v6 FR2 | MYWVRQA PGKEREWVSS |
| 23 | 1D10v6 FR3 | AY AESVKGRFTI SRDNAKNTLY LQMSSLRAED TAVYYC |
| 24 | 1D10v6 FR4 | RGQGTL VTVKP |
| 13 | 1D10v6-Fc (bivalent) | EVQLLESGGG EVQPGGSLRL SCAASGFTFS DAFMYWVRQA PGKEREWVSS ISNRGLKTAY AESVKGRFTI SRDNAKNTLY LQMSSLRAED TAVYYCSRDV DADFRGQGTL VTVKPGGGGD KTHTCPPCPA PELLGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSRDELTKN QVSLTCLVKG FYPSDIAVEW ESNGQPENNY KTTPPVLDSD GSFFLYSKLT VDKSRWQQGN VFSCSVMHEA LHNHYTQKSL SLSPGK |
| 14 | 3x1D10v6 | EVQLLESGGG EVQPGGSLRL SCAASGFTFS DAFMYWVRQA PGKEREWVSS ISNRGLKTAY AESVKGRFTI SRDNAKNTLY LQMSSLRAED TAVYYCSRDV DADFRGQGTL VTVKPGGSGG SEVQLLESGG GEVQPGGSLR LSCAASGFTF SDAFMYWVRQ APGKEREWVS SISNRGLKTA YAESVKGRFT ISRDNAKNTL YLQMSSLRAE DTAVYYCSRD VDADFRGQGT LVTVKPGGSS GSEVQLLESG GGEVQPGGSL RLSCAASGFT FSDAFMYWVR QAPGKEREWV SSISNRGLKT AYAESVKGRF TISRDNAKNT LYLQMSSLRA EDTAVYYCSR DVDADFRGQG TLVTVKP |
| 15 | 3x1D10v6-Fc (hexavalent; also referred to as Hex-1D10v6) | EVQLLESGGG EVQPGGSLRL SCAASGFTFS DAFMYWVRQA PGKEREWVSS ISNRGLKTAY AESVKGRFTI SRDNAKNTLY LQMSSLRAED TAVYYCSRDV DADFRGQGTL VTVKPGGSGG SEVQLLESGG GEVQPGGSLR LSCAASGFTF SDAFMYWVRQ |

| SEQ ID NO | Description | Sequence |
|---|---|---|
| | | APGKEREWVS SISNRGLKTA YAESVKGRFT ISRDNAKNTL YLQMSSLRAE DTAVYYCSRD VDADFRGQGT LVTVKPGGSS GSEVQLLESG GGEVQPGGSL RLSCAASGFT FSDAFMYWVR QAPGKEREWV SSISNRGLKT AYAESVKGRF TISRDNAKNT LYLQMSSLRA EDTAVYYCSR DVDADFRGQG TLVTVKPGGG GDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVMH EALHNHYTQK SLSLSPGK |
| 16 | 2x1D10v6-Fc (tetravalent) | EVQLLESGGG EVQPGGSLRL SCAASGFTFS DAFMYWVRQA PGKEREWVSS ISNRGLKTAY AESVKGRFTI SRDNAKNTLY LQMSSLRAED TAVYYCSRDV DADFRGQGTL VTVKPGGSSG SEVQLLESGG GEVQPGGSLR LSCAASGFTF SDAFMYWVRQ APGKEREWVS SISNRGLKTA YAESVKGRFT ISRDNAKNTL YLQMSSLRAE DTAVYYCSRD VDADFRGQGT LVTVKPGGGG DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 25 | Fc domain 1 (human IgG1) | DKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVMH EALHNHYTQK SLSLSPGK |
| 26 | Fc domain 2 (human IgG1 xELL) | DKTHTCPPCP APGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SRDELTKNQV SLTCLVKGFY PSDIAVEWES NGQPENNYKT TPPVLDSDGS FFLYSKLTVD KSRWQQGNVF SCSVMHEALH NHYTQKSLSL SPGK |
| 27 | CD3-zeta signaling domain | RVKFSRSADA PAYQQGQNQL YNELNLGRRE EYDVLDKRRG RDPEMGGKPR RKNPQEGLYN ELQKDKMAEA YSEIGMKGER RRGKGHDGLY QGLSTATKDT YDALHMQALP PR |
| 28 | signaling domain is a derived from CD28 or 4-1BB | KRGRKKLLYI FKQPFMRPVQ TTQEEDGCSC RFPEEEEGGC EL |
| 29 | signaling domain is a derived from CD28 or 4-1BB | SKRSRLLHSD YMNMTPRRPG PTRKHYQPYA PPRDFAAYRS |
| 30 | signaling domain is a derived from CD28 or 4-1BB | RSKRSRLLHS DYMNMTPRRP GPTRKHYQPY APPRDFAAYR S |
| 31 | signaling domain is a derived from CD28 or 4-1BB | FWVRSKRSRL LHSDYMNMTP RRPGPTRKHY QPYAPPRDFA AYRS |
| 32 | hinge or transmembrane domain derived from CD8 | KPTTTPAPRP PTPAPTIASQ PLSLRPEASR PAAGGAVHTR GLDFASDIYI WAPLAGTCGV LLLSLVITLY C |
| 33 | hinge or transmembrane domain derived from CD8 | AKPTTTPAPR PPTPAPTIAS QPLSLRPEAC RPAAGGAVHT RGLDFACDIY IWAPLAGTCG |

| Table of Certain Sequences | | |
|---|---|---|
| SEQ ID NO | Description | Sequence |
| 34 | hinge or transmembrane domain derived from CD8 | VLLLSLVIT |

SEQUENCE LISTING

```
Sequence total quantity: 34
SEQ ID NO: 1                moltype = AA   length = 277
FEATURE                     Location/Qualifiers
source                      1..277
                            mol_type = protein
                            organism = Homo sapiens
SEQUENCE: 1
MCVGARRLGR GPCAALLLLG LGLSTVTGLH CVGDTYPSND RCCHECRPGN GMVSRCSRSQ    60
NTVCRPCGPG FYNDVVSSKP CKPCTWCNLR SGSERKQLCT ATQDTVCRCR AGTQPLDSYK   120
PGVDCAPCPP GHFSPGDNQA CKPWTNCTLA GKHTLQPASN SSDAICEDRD PPATQPQETQ   180
GPPARPITVQ PTEAWPRTSQ GPSTRPVEVP GGRAVAAILG LGLVLGLLGP LAILLALYLL   240
RRDQRLPPDA HKPPGGGSFR TPIQEEQADA HSTLAKI                           277

SEQ ID NO: 2                moltype = AA   length = 277
FEATURE                     Location/Qualifiers
source                      1..277
                            mol_type = protein
                            organism = Macaca fascicularis
SEQUENCE: 2
MCVGARRLGR GPCAALLLLG LGLSTTAKLH CVGDTYPSND RCCQECRPGN GMVSRCNRSQ    60
NTVCRPCGPG FYNDVVSAKP CKACTWCNLR SGSERKQPCT ATQDTVCRCR AGTQPLDSYK   120
PGVDCAPCPP GHFSPGDNQA CKPWTNCTLA GKHTLQPASN SSDAICEDRD PPPTQPQETQ   180
GPPARPTTVQ PTEAWPRTSQ RPSTRPVEVP RGPAVAAILG LGLALGLLGP LAMLLALLLL   240
RRDQRLPPDA PKAPGGGSFR TPIQEEQADA HSALAKI                           277

SEQ ID NO: 3                moltype = AA   length = 115
FEATURE                     Location/Qualifiers
REGION                      1..115
                            note = 1D10v1
source                      1..115
                            mol_type = protein
                            organism = synthetic construct
SEQUENCE: 3
EVQLLESGGG EVQPGGSLRL SCAASGFTFS DAFMYWVRQA PGKGLEWVSS ISNRGLKTAY    60
AESVKGRFTI SRDNAKNTLY LQMSSLRAED TAVYYCSRDV DGDFRGQGTL VTVKP        115

SEQ ID NO: 4                moltype = AA   length = 8
FEATURE                     Location/Qualifiers
REGION                      1..8
                            note = 1D10v1 CDR1
source                      1..8
                            mol_type = protein
                            organism = synthetic construct
SEQUENCE: 4
GFTFSDAF                                                             8

SEQ ID NO: 5                moltype = AA   length = 8
FEATURE                     Location/Qualifiers
REGION                      1..8
                            note = 1D10v1 CDR2
source                      1..8
                            mol_type = protein
                            organism = synthetic construct
SEQUENCE: 5
ISNRGLKT                                                             8

SEQ ID NO: 6                moltype = AA   length = 8
FEATURE                     Location/Qualifiers
REGION                      1..8
                            note = 1D10v1 CDR3
source                      1..8
```

```
                        mol_type = protein
                        organism = synthetic construct
SEQUENCE: 6
SRDVDGDF                                                              8

SEQ ID NO: 7            moltype = AA   length = 346
FEATURE                 Location/Qualifiers
REGION                  1..346
                        note = 1D10v1-Fc (bivalent)
source                  1..346
                        mol_type = protein
                        organism = synthetic construct
SEQUENCE: 7
EVQLLESGGG EVQPGGSLRL SCAASGFTFS DAFMYWVRQA PGKGLEWVSS ISNRGLKTAY   60
AESVKGRFTI SRDNAKNTLY LQMSSLRAED TAVYYCSRDV DGDFRGQGTL VTVKPGGGGD  120
KTHTCPPCPA PELLGGPSVF LFPPKPKDTL MISRTPEVTC VVVDVSHEDP EVKFNWYVDG  180
VEVHNAKTKP REEQYNSTYR VVSVLTVLHQ DWLNGKEYKC KVSNKALPAP IEKTISKAKG  240
QPREPQVYTL PPSRDELTKN QVSLTCLVKG FYPSDIAVEW ESNGQPENNY KTTPPVLDSD  300
GSFFLYSKLT VDKSRWQQGN VFSCSVMHEA LHNHYTQKSL SLSPGK                 346

SEQ ID NO: 8            moltype = AA   length = 588
FEATURE                 Location/Qualifiers
REGION                  1..588
                        note = 3x1D10v1-Fc (hexavalent; also referred to as
                         Hex-1D10v1)
source                  1..588
                        mol_type = protein
                        organism = synthetic construct
SEQUENCE: 8
EVQLLESGGG EVQPGGSLRL SCAASGFTFS DAFMYWVRQA PGKGLEWVSS ISNRGLKTAY   60
AESVKGRFTI SRDNAKNTLY LQMSSLRAED TAVYYCSRDV DGDFRGQGTL VTVKPGGSGG  120
SEVQLLESGG GEVQPGGSLR LSCAASGFTF SDAFMYWVRQ APGKGLEWVS SISNRGLKTA  180
YAESVKGRFT ISRDNAKNTL YLQMSSLRAE DTAVYYCSRD VDGDFRGQGT LVTVKPGGSG  240
GSEVQLLESG GGEVQPGGSL RLSCAASGFT FSDAFMYWVR QAPGKGLEWV SSISNRGLKT  300
AYAESVKGRF TISRDNAKNT LYLQMSSLRA EDTAVYYCSR DVDGDFRGQG TLVTVKPGGG  360
GDKTHTCPPC PAPELLGGPS VFLFPPKPKD TLMISRTPEV TCVVVDVSHE DPEVKFNWYV  420
DGVEVHNAKT KPREEQYNST YRVVSVLTVL HQDWLNGKEY KCKVSNKALP APIEKTISKA  480
KGQPREPQVY TLPPSRDELT KNQVSLTCLV KGFYPSDIAV EWESNGQPEN NYKTTPPVLD  540
SDGSFFLYSK LTVDKSRWQQ GNVFSCSVMH EALHNHYTQK SLSLSPGK               588

SEQ ID NO: 9            moltype = AA   length = 115
FEATURE                 Location/Qualifiers
REGION                  1..115
                        note = 1D10v6
source                  1..115
                        mol_type = protein
                        organism = synthetic construct
SEQUENCE: 9
EVQLLESGGG EVQPGGSLRL SCAASGFTFS DAFMYWVRQA PGKEREWVSS ISNRGLKTAY   60
AESVKGRFTI SRDNAKNTLY LQMSSLRAED TAVYYCSRDV DADFRGQGTL VTVKP       115

SEQ ID NO: 10           moltype = AA   length = 8
FEATURE                 Location/Qualifiers
REGION                  1..8
                        note = 1D10v6 CDR1
source                  1..8
                        mol_type = protein
                        organism = synthetic construct
SEQUENCE: 10
GFTFSDAF                                                              8

SEQ ID NO: 11           moltype = AA   length = 8
FEATURE                 Location/Qualifiers
REGION                  1..8
                        note = 1D10v6 CDR2
source                  1..8
                        mol_type = protein
                        organism = synthetic construct
SEQUENCE: 11
ISNRGLKT                                                              8

SEQ ID NO: 12           moltype = AA   length = 8
FEATURE                 Location/Qualifiers
REGION                  1..8
                        note = 1D10v6 CDR3
source                  1..8
                        mol_type = protein
                        organism = synthetic construct
SEQUENCE: 12
```

```
SRDVDADF                                                                             8

SEQ ID NO: 13           moltype = AA  length = 346
FEATURE                 Location/Qualifiers
REGION                  1..346
                        note = 1D10v6-Fc (bivalent)
source                  1..346
                        mol_type = protein
                        organism = synthetic construct
SEQUENCE: 13
EVQLLESGGG EVQPGGSLRL SCAASGFTFS DAFMYWVRQA PGKEREWVSS ISNRGLKTAY    60
AESVKGRFTI SRDNAKNTLY LQMSSLRAED TAVYYCSRDV DADFRGQGTL VTVKPGGGGD   120
KTHTCPPCPA PELLGGPSVF LFPPKPKDTL MISRTPEVTC VVVDVSHEDP EVKFNWYVDG   180
VEVHNAKTKP REEQYNSTYR VVSVLTVLHQ DWLNGKEYKC KVSNKALPAP IEKTISKAKG   240
QPREPQVYTL PPSRDELTKN QVSLTCLVKG FYPSDIAVEW ESNGQPENNY KTTPPVLDSD   300
GSFFLYSKLT VDKSRWQQGN VFSCSVMHEA LHNHYTQKSL SLSPGK                  346

SEQ ID NO: 14           moltype = AA  length = 357
FEATURE                 Location/Qualifiers
REGION                  1..357
                        note = 3x1D10v6
source                  1..357
                        mol_type = protein
                        organism = synthetic construct
SEQUENCE: 14
EVQLLESGGG EVQPGGSLRL SCAASGFTFS DAFMYWVRQA PGKEREWVSS ISNRGLKTAY    60
AESVKGRFTI SRDNAKNTLY LQMSSLRAED TAVYYCSRDV DADFRGQGTL VTVKPGGSGG   120
SEVQLLESGG GEVQPGGSLR LSCAASGFTF SDAFMYWVRQ APGKEREWVS SISNRGLKTA   180
YAESVKGRFT ISRDNAKNTL YLQMSSLRAE DTAVYYCSRD VDADFRGQGT LVTVKPGGSS   240
GSEVQLLESG GGEVQPGGSL RLSCAASGFT FSDAFMYWVR QAPGKEREWV SSISNRGLKT   300
AYAESVKGRF TISRDNAKNT LYLQMSSLRA EDTAVYYCSR DVDADFRGQG TLVTVKP      357

SEQ ID NO: 15           moltype = AA  length = 588
FEATURE                 Location/Qualifiers
REGION                  1..588
                        note = 3x1D10v6-Fc (hexavalent; also referred to as
                         Hex-1D10v6)
source                  1..588
                        mol_type = protein
                        organism = synthetic construct
SEQUENCE: 15
EVQLLESGGG EVQPGGSLRL SCAASGFTFS DAFMYWVRQA PGKEREWVSS ISNRGLKTAY    60
AESVKGRFTI SRDNAKNTLY LQMSSLRAED TAVYYCSRDV DADFRGQGTL VTVKPGGSGG   120
SEVQLLESGG GEVQPGGSLR LSCAASGFTF SDAFMYWVRQ APGKEREWVS SISNRGLKTA   180
YAESVKGRFT ISRDNAKNTL YLQMSSLRAE DTAVYYCSRD VDADFRGQGT LVTVKPGGSS   240
GSEVQLLESG GGEVQPGGSL RLSCAASGFT FSDAFMYWVR QAPGKEREWV SSISNRGLKT   300
AYAESVKGRF TISRDNAKNT LYLQMSSLRA EDTAVYYCSR DVDADFRGQG TLVTVKPGGS   360
GDKTHTCPPC PAPELLGGPS VFLFPPKPKD TLMISRTPEV TCVVVDVSHE DPEVKFNWYV   420
DGVEVHNAKT KPREEQYNST YRVVSVLTVL HQDWLNGKEY KCKVSNKALP APIEKTISKA   480
KGQPREPQVY TLPPSRDELT KNQVSLTCLV KGFYPSDIAV EWESNGQPEN NYKTTPPVLD   540
SDGSFFLYSK LTVDKSRWQQ GNVFSCSVMH EALHNHYTQK SLSLSPGK                588

SEQ ID NO: 16           moltype = AA  length = 467
FEATURE                 Location/Qualifiers
REGION                  1..467
                        note = 2x1D10v6-Fc (tetravalent)
source                  1..467
                        mol_type = protein
                        organism = synthetic construct
SEQUENCE: 16
EVQLLESGGG EVQPGGSLRL SCAASGFTFS DAFMYWVRQA PGKEREWVSS ISNRGLKTAY    60
AESVKGRFTI SRDNAKNTLY LQMSSLRAED TAVYYCSRDV DADFRGQGTL VTVKPGGSSG   120
SEVQLLESGG GEVQPGGSLR LSCAASGFTF SDAFMYWVRQ APGKEREWVS SISNRGLKTA   180
YAESVKGRFT ISRDNAKNTL YLQMSSLRAE DTAVYYCSRD VDADFRGQGT LVTVKPGGGG   240
DKTHTCPPCP APELLGGPSV FLFPPKPKDT LMISRTPEVT CVVVDVSHED PEVKFNWYVD   300
GVEVHNAKTK PREEQYNSTY RVVSVLTVLH QDWLNGKEYK CKVSNKALPA PIEKTISKAK   360
GQPREPQVYT LPPSRDELTK NQVSLTCLVK GFYPSDIAVE WESNGQPENN YKTTPPVLDS   420
DGSFFLYSKL TVDKSRWQQG NVFSCSVMHE ALHNHYTQKS LSLSPGK                 467

SEQ ID NO: 17           moltype = AA  length = 25
FEATURE                 Location/Qualifiers
REGION                  1..25
                        note = 1D10v1 FR1
source                  1..25
                        mol_type = protein
                        organism = synthetic construct
SEQUENCE: 17
EVQLLESGGG EVQPGGSLRL SCAAS                                          25
```

```
SEQ ID NO: 18             moltype = AA  length = 17
FEATURE                   Location/Qualifiers
REGION                    1..17
                          note = 1D10v1 FR2
source                    1..17
                          mol_type = protein
                          organism = synthetic construct
SEQUENCE: 18
MYWVRQAPGK GLEWVSS                                                        17

SEQ ID NO: 19             moltype = AA  length = 38
FEATURE                   Location/Qualifiers
REGION                    1..38
                          note = 1D10v1 FR3
source                    1..38
                          mol_type = protein
                          organism = synthetic construct
SEQUENCE: 19
AYAESVKGRF TISRDNAKNT LYLQMSSLRA EDTAVYYC                                  38

SEQ ID NO: 20             moltype = AA  length = 11
FEATURE                   Location/Qualifiers
REGION                    1..11
                          note = 1D10v1 FR4
source                    1..11
                          mol_type = protein
                          organism = synthetic construct
SEQUENCE: 20
RGQGTLVTVK P                                                              11

SEQ ID NO: 21             moltype = AA  length = 25
FEATURE                   Location/Qualifiers
REGION                    1..25
                          note = 1D10v6 FR1
source                    1..25
                          mol_type = protein
                          organism = synthetic construct
SEQUENCE: 21
EVQLLESGGG EVQPGGSLRL SCAAS                                                25

SEQ ID NO: 22             moltype = AA  length = 17
FEATURE                   Location/Qualifiers
REGION                    1..17
                          note = 1D10v6 FR2
source                    1..17
                          mol_type = protein
                          organism = synthetic construct
SEQUENCE: 22
MYWVRQAPGK EREWVSS                                                        17

SEQ ID NO: 23             moltype = AA  length = 38
FEATURE                   Location/Qualifiers
REGION                    1..38
                          note = 1D10v6 FR3
source                    1..38
                          mol_type = protein
                          organism = synthetic construct
SEQUENCE: 23
AYAESVKGRF TISRDNAKNT LYLQMSSLRA EDTAVYYC                                  38

SEQ ID NO: 24             moltype = AA  length = 11
FEATURE                   Location/Qualifiers
REGION                    1..11
                          note = 1D10v6 FR4
source                    1..11
                          mol_type = protein
                          organism = synthetic construct
SEQUENCE: 24
RGQGTLVTVK P                                                              11

SEQ ID NO: 25             moltype = AA  length = 227
FEATURE                   Location/Qualifiers
source                    1..227
                          mol_type = protein
                          organism = Homo sapiens
SEQUENCE: 25
DKTHTCPPCP APELLGGPSV FLFPPKPKDT LMISRTPEVT CVVVDVSHED PEVKFNWYVD          60
GVEVHNAKTK PREEQYNSTY RVVSVLTVLH QDWLNGKEYK CKVSNKALPA PIEKTISKAK         120
GQPREPQVYT LPPSRDELTK NQVSLTCLVK GFYPSDIAVE WESNGQPENN YKTTPPVLDS         180
```

```
DGSFFLYSKL TVDKSRWQQG NVFSCSVMHE ALHNHYTQKS LSLSPGK            227

SEQ ID NO: 26           moltype = AA  length = 224
FEATURE                 Location/Qualifiers
source                  1..224
                        mol_type = protein
                        organism = Homo sapiens
SEQUENCE: 26
DKTHTCPPCP APGGPSVFLF PPKPKDTLMI SRTPEVTCVV VDVSHEDPEV KFNWYVDGVE  60
VHNAKTKPRE EQYNSTYRVV SVLTVLHQDW LNGKEYKCKV SNKALPAPIE KTISKAKGQP 120
REPQVYTLPP SRDELTKNQV SLTCLVKGFY PSDIAVEWES NGQPENNYKT TPPVLDSDGS 180
FFLYSKLTVD KSRWQQGNVF SCSVMHEALH NHYTQKSLSL SPGK                 224

SEQ ID NO: 27           moltype = AA  length = 112
FEATURE                 Location/Qualifiers
REGION                  1..112
                        note = Synthetic: CD3-zeta signaling domain
source                  1..112
                        mol_type = protein
                        organism = synthetic construct
SEQUENCE: 27
RVKFSRSADA PAYQQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR        112

SEQ ID NO: 28           moltype = AA  length = 42
FEATURE                 Location/Qualifiers
REGION                  1..42
                        note = Synthetic: signaling domain is a derived from CD28
                         or 4-1BB
source                  1..42
                        mol_type = protein
                        organism = synthetic construct
SEQUENCE: 28
KRGRKKLLYI FKQPFMRPVQ TTQEEDGCSC RFPEEEEGGC EL                    42

SEQ ID NO: 29           moltype = AA  length = 40
FEATURE                 Location/Qualifiers
REGION                  1..40
                        note = Synthetic: signaling domain is a derived from CD28
                         or 4-1BB
source                  1..40
                        mol_type = protein
                        organism = synthetic construct
SEQUENCE: 29
SKRSRLLHSD YMNMTPRRPG PTRKHYQPYA PPRDFAAYRS                       40

SEQ ID NO: 30           moltype = AA  length = 41
FEATURE                 Location/Qualifiers
REGION                  1..41
                        note = Synthetic: signaling domain is a derived from CD28
                         or 4-1BB
source                  1..41
                        mol_type = protein
                        organism = synthetic construct
SEQUENCE: 30
RSKRSRLLHS DYMNMTPRRP GPTRKHYQPY APPRDFAAYR S                     41

SEQ ID NO: 31           moltype = AA  length = 44
FEATURE                 Location/Qualifiers
REGION                  1..44
                        note = Synthetic: signaling domain is a derived from CD28
                         or 4-1BB
source                  1..44
                        mol_type = protein
                        organism = synthetic construct
SEQUENCE: 31
FWVRSKRSRL LHSDYMNMTP RRPGPTRKHY QPYAPPRDFA AYRS                  44

SEQ ID NO: 32           moltype = AA  length = 71
FEATURE                 Location/Qualifiers
REGION                  1..71
                        note = Synthetic: hinge or transmembrane domain derived
                         from CD8
source                  1..71
                        mol_type = protein
                        organism = synthetic construct
SEQUENCE: 32
KPTTTPAPRP PTPAPTIASQ PLSLRPEASR PAAGGAVHTR GLDFASDIYI WAPLAGTCGV  60
LLLSLVITLY C                                                      71
```

```
SEQ ID NO: 33          moltype = AA  length = 60
FEATURE                Location/Qualifiers
REGION                 1..60
                       note = Synthetic: hinge or transmembrane domain derived
                        from CD8
source                 1..60
                       mol_type = protein
                       organism = synthetic construct
SEQUENCE: 33
AKPTTTPAPR PPTPAPTIAS QPLSLRPEAC RPAAGGAVHT RGLDFACDIY IWAPLAGTCG   60

SEQ ID NO: 34          moltype = AA  length = 9
FEATURE                Location/Qualifiers
REGION                 1..9
                       note = Synthetic: hinge or transmembrane domain derived
                        from CD8
source                 1..9
                       mol_type = protein
                       organism = synthetic construct
SEQUENCE: 34
VLLLSLVIT                                                            9
```

What is claimed is:

1. An isolated nucleic acid that encodes a polypeptide comprising at least one VHH domain that binds OX40, wherein the VHH domain comprises a CDR1 comprising the amino acid sequence of SEQ ID NO: 10, a CDR2 comprising the amino acid sequence of SEQ ID NO: 11, and a CDR3 comprising the amino acid sequence of SEQ ID NO: 12, and wherein the VHH domain comprises a FR2 comprising the amino acid sequence of SEQ ID NO: 22.

2. The isolated nucleic acid of claim 1, wherein the VHH domain comprises a FR3 comprising the amino acid sequence of SEQ ID NO: 23.

3. The isolated nucleic acid of claim 1, wherein the VHH domain comprises the amino acid sequence of SEQ ID NO: 9.

4. The isolated nucleic acid of claim 1, wherein the polypeptide comprises two, three, or four VHH domains.

5. The isolated nucleic acid of claim 4, wherein each VHH domain binds OX40.

6. The isolated nucleic acid of claim 5, wherein each VHH domain comprises a CDR1 comprising the amino acid sequence of SEQ ID NO: 10, a CDR2 comprising the amino acid sequence of SEQ ID NO: 11, and a CDR3 comprising the amino acid sequence of SEQ ID NO: 12, and wherein each VHH domain comprises a FR2 comprising the amino acid sequence of SEQ ID NO: 22.

7. The isolated nucleic acid of claim 6, wherein each VHH domain comprises a FR3 comprising the amino acid sequence of SEQ ID NO: 23.

8. The isolated nucleic acid of claim 5, wherein each VHH domain comprises the amino acid sequence of SEQ ID NO: 9.

9. The isolated nucleic acid of claim 4, wherein the polypeptide comprises an Fc domain.

10. The isolated nucleic acid of claim 9, wherein the Fc domain comprises an amino acid sequence selected from SEQ ID NOs: 25 and 26.

11. The isolated nucleic acid of claim 1, wherein the polypeptide comprises an Fc domain.

12. The isolated nucleic acid of claim 11, wherein the polypeptide comprising an Fc domain comprises an amino acid sequence selected from SEQ ID NOs: 25 and 26.

13. The isolated nucleic acid of claim 1, wherein polypeptide comprises the amino acid sequence of SEQ ID NO: 14.

14. The isolated nucleic acid of claim 13, wherein the polypeptide comprises an Fc domain.

15. A vector comprising the isolated nucleic acid of claim 14.

16. A host cell comprising the vector of claim 15.

17. A host cell comprising the isolated nucleic acid of claim 14.

18. A vector comprising the isolated nucleic acid of claim 13.

19. A host cell comprising the vector of claim 18.

20. A host cell comprising the isolated nucleic acid of claim 13.

21. The isolated nucleic acid of claim 1, wherein the polypeptide comprises the amino acid sequence of SEQ ID NO: 15.

22. A vector comprising the isolated nucleic acid of claim 21.

23. A host cell comprising the vector of claim 22.

24. A host cell comprising the isolated nucleic acid of claim 21.

25. A vector comprising the isolated nucleic acid of claim 1.

26. A host cell comprising the vector of claim 25.

27. A host cell comprising the isolated nucleic acid of claim 1.

28. An isolated nucleic acid that encodes a polypeptide that binds OX40 consisting of the amino acid sequence of SEQ ID NO: 15.

29. A host cell that expresses a polypeptide comprising at least one VHH domain that binds OX40, wherein the VHH domain comprises a CDR1 comprising the amino acid sequence of SEQ ID NO: 10, a CDR2 comprising the amino acid sequence of SEQ ID NO: 11, and a CDR3 comprising the amino acid sequence of SEQ ID NO: 12, and wherein each VHH domain comprises a FR2 comprising the amino acid sequence of SEQ ID NO: 22.

30. The host cell of claim 29, wherein the VHH domain comprises a FR3 comprising the amino acid sequence of SEQ ID NO: 23.

31. The host cell of claim 29, wherein the VHH domain comprises the amino acid sequence of SEQ ID NO: 9.

32. The host cell of claim 29, wherein the polypeptide comprises two, three, or four VHH domains.

33. The host cell of claim 32, wherein each VHH domain binds OX40.

34. The host cell of claim 33, wherein each VHH domain comprises a CDR1 comprising the amino acid sequence of SEQ ID NO: 10, a CDR2 comprising the amino acid sequence of SEQ ID NO: 11, and a CDR3 comprising the amino acid sequence of SEQ ID NO: 12, and wherein each VHH domain comprises a FR2 comprising the amino acid sequence of SEQ ID NO: 22.

35. The host cell of claim 34, wherein each VHH domain comprises a FR3 comprising the amino acid sequence of SEQ ID NO: 23.

36. The host cell of claim 33, wherein each VHH domain comprises the amino acid sequence of SEQ ID NO: 9.

37. The host cell of claim 32, wherein the polypeptide comprises an Fc domain.

38. The host cell of claim 37, wherein the Fc domain comprises an amino acid sequence selected from SEQ ID NOs: 25 and 26.

39. The host cell of claim 29, wherein the polypeptide comprises an Fc domain.

40. The host cell of claim 39, wherein the polypeptide comprising an Fc domain comprises an amino acid sequence selected from SEQ ID NOs: 25 and 26.

41. The host cell of claim 29, wherein polypeptide comprises the amino acid sequence of SEQ ID NO: 14.

42. The host cell of claim 41, wherein the polypeptide comprises an Fc domain.

43. The host cell of claim 29, wherein the polypeptide comprises the amino acid sequence of SEQ ID NO: 15.

44. The host cell of claim 29, which secretes the polypeptide.

45. The host cell of claim 29, which is a primary human cell.

46. The host cell of claim 45, which is a primary human T cell.

47. The host cell of claim 46, which is a chimeric antigen receptor (CAR)-T cell.

* * * * *